United States Patent [19]
Esteves et al.

[11] Patent Number: 6,012,216
[45] Date of Patent: Jan. 11, 2000

[54] STAND ALONE SWAGE APPARATUS

[75] Inventors: Anthony Esteves, Somerville; John F. Blanch, Tinton Falls; Robert A. Daniele, Flemington; David D. Demarest, Parsippany, all of N.J.

[73] Assignee: Ethicon, Inc., Somerville, N.J.

[21] Appl. No.: 08/848,927

[22] Filed: Apr. 30, 1997

[51] Int. Cl.⁷ ................................................. B23Q 15/00
[52] U.S. Cl. ........................... 29/564.7; 29/705; 29/712; 29/715; 29/788
[58] Field of Search ................................ 29/564.6, 564.7, 29/705, 712, 711, 788, 517, 715, 786, 564.8; 53/118, 138.1; 198/391, 803.7; 901/7

[56] References Cited

U.S. PATENT DOCUMENTS

| | | |
|---|---|---|
| 2,736,194 | 2/1956 | Dilts . |
| 4,187,051 | 2/1980 | Kirsch et al. . |
| 4,358,976 | 11/1982 | Alviti . |
| 4,437,114 | 3/1984 | LaRussa . |
| 4,672,871 | 6/1987 | Gudmestad . |
| 4,674,869 | 6/1987 | Pryor et al. . |
| 4,744,035 | 5/1988 | Hashim . |
| 4,832,025 | 5/1989 | Coates . |
| 4,835,450 | 5/1989 | Suzuki . |
| 4,942,796 | 7/1990 | Dom et al. . |
| 5,065,237 | 11/1991 | Tsikos et al. . |
| 5,131,533 | 7/1992 | Alpern . |
| 5,150,307 | 9/1992 | McCourt et al. . |
| 5,195,234 | 3/1993 | Pine et al. . |
| 5,253,765 | 10/1993 | Moorehead et al. . |
| 5,394,971 | 3/1995 | Colligan et al. .......................... 198/391 |
| 5,438,746 | 8/1995 | Demarest et al. ...................... 29/564.6 |
| 5,473,810 | 12/1995 | Demarest et al. ......................... 29/712 |
| 5,477,609 | 12/1995 | Demarest et al. ......................... 29/788 |
| 5,487,216 | 1/1996 | Demarest et al. ......................... 29/705 |
| 5,511,670 | 4/1996 | Demarest et al. ................ 198/803.7 X |
| 5,568,593 | 10/1996 | Demarest et al. ....................... 901/7 X |
| 5,793,634 | 8/1998 | Demarest et al. .................... 29/705 X |

FOREIGN PATENT DOCUMENTS

| | | |
|---|---|---|
| 428 253 | 5/1991 | European Pat. Off. . |
| 63-299834 | 12/1988 | Japan . |
| 3-82458 | 4/1991 | Japan . |

*Primary Examiner*—William Briggs
*Attorney, Agent, or Firm*—Scully, Scott, Murphy & Presser

[57] ABSTRACT

A semi-automated machine for singulating individual surgical needles from an bulk supply and attaching a suture to the surgical needle is described. Each of the surgical needles has a suture receiving opening formed therein for receiving a suture. The machine includes a singulation station having a sliding surface that assists an operator in singulating needles and depositing them in a pair of drop locations for subsequent automatic handling. Indexing conveyors, an articulated robot and a precision conveyor are used with a precise positioning station for orienting each needle for automatic handling. A universal gripper mounted on a rotary indexing device automatically receives each individual needle in a predetermined orientation and conveys the needle for sequential processing from station to station to form the needle-suture assembly. A suture feeding and cutting station automatically cuts an indefinite length of suture material to a definite length suture strand and automatically inserts an end of the definite length suture strand into the suture receiving opening formed in the needle. A swage station is provided for swaging the needle to close the suture receiving opening about the suture to secure said suture thereto and form therefrom a needle and suture assembly. A suture pull-test station test each needle suture bond, and selectively and destructively tests the bond for adjusting the swage dies and for statistical quality control. A final off-load station provides an apparatus for assembling a predetermined number of need-suture assemblies in a bundle for subsequent packaging.

98 Claims, 36 Drawing Sheets

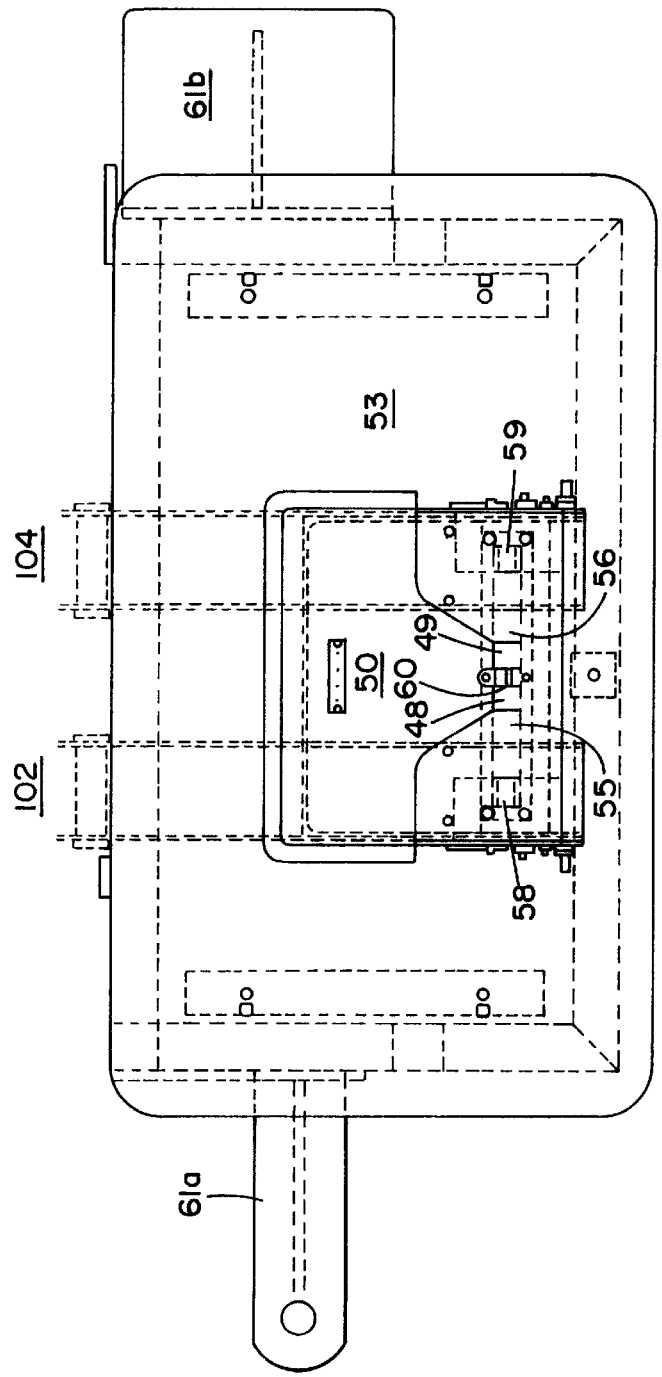
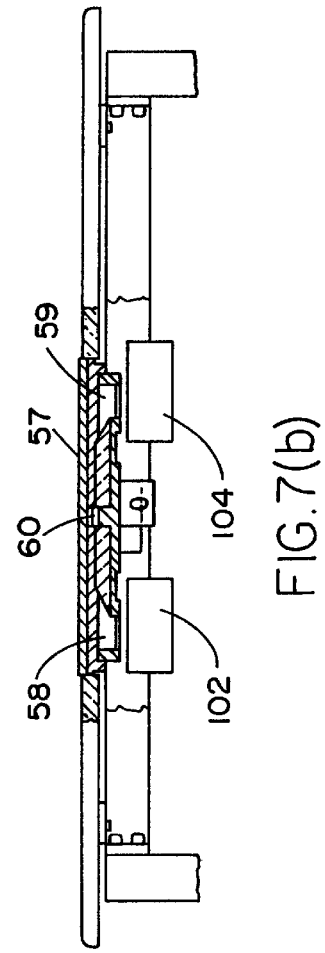
FIG.7(a)
FIG.7(b)

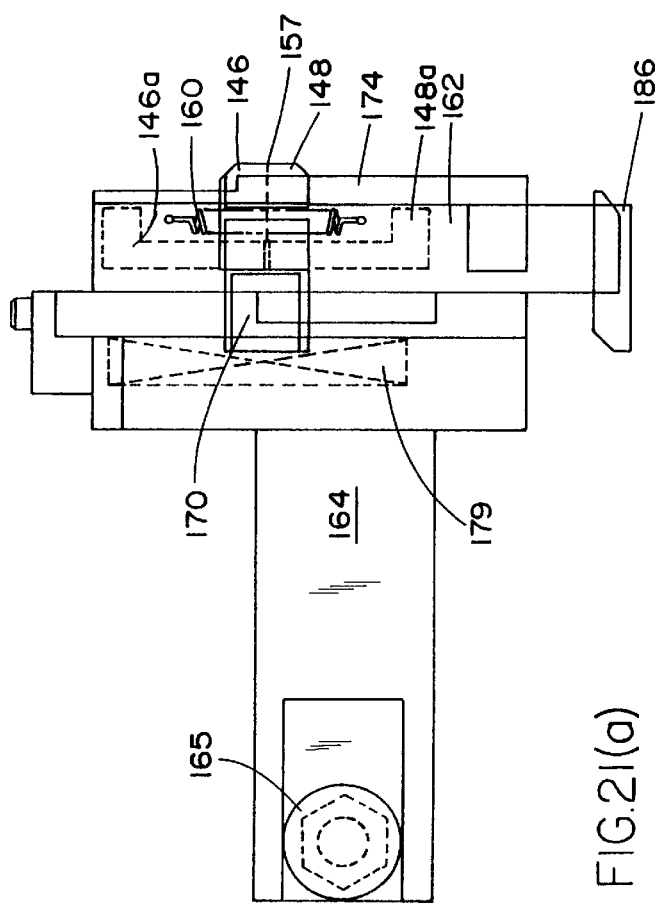
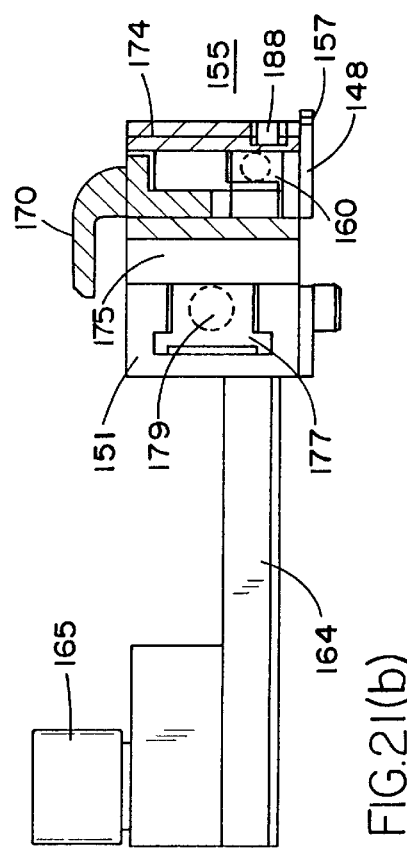
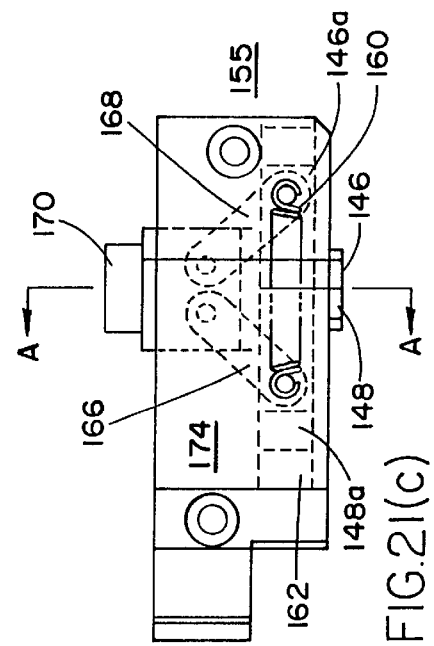
FIG.21(a)
FIG.21(b)
FIG.21(c)

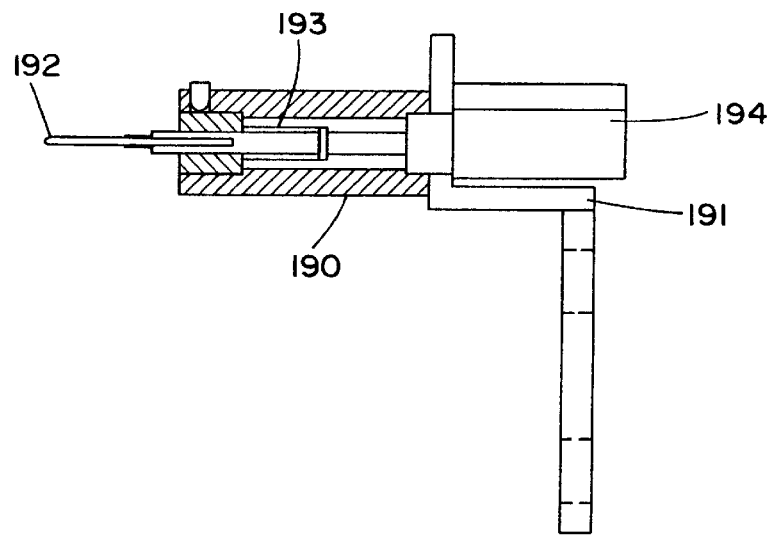
FIG.24
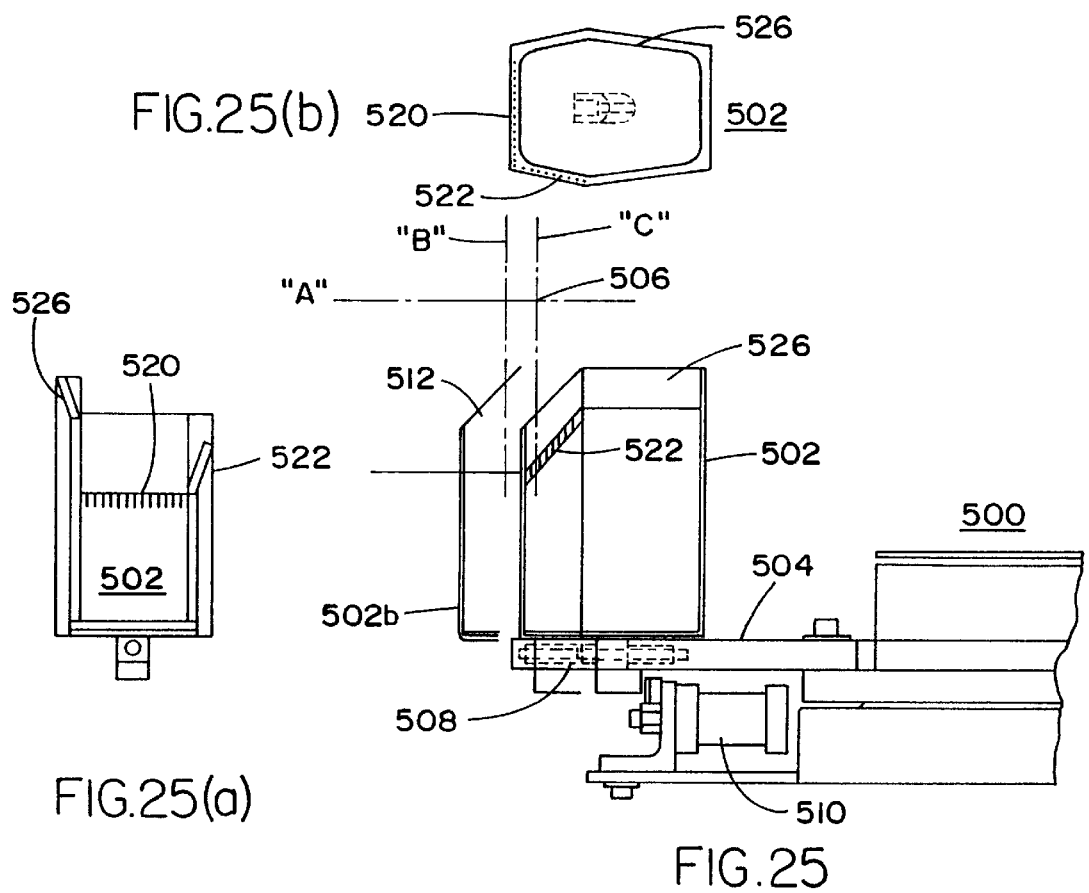
FIG.25(b)
FIG.25(a)
FIG.25

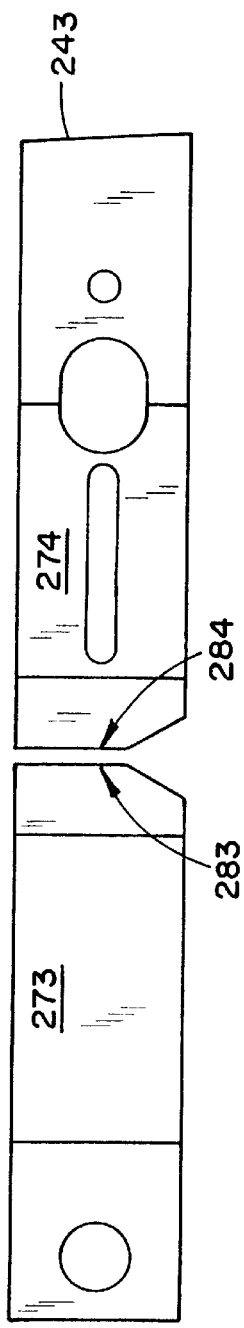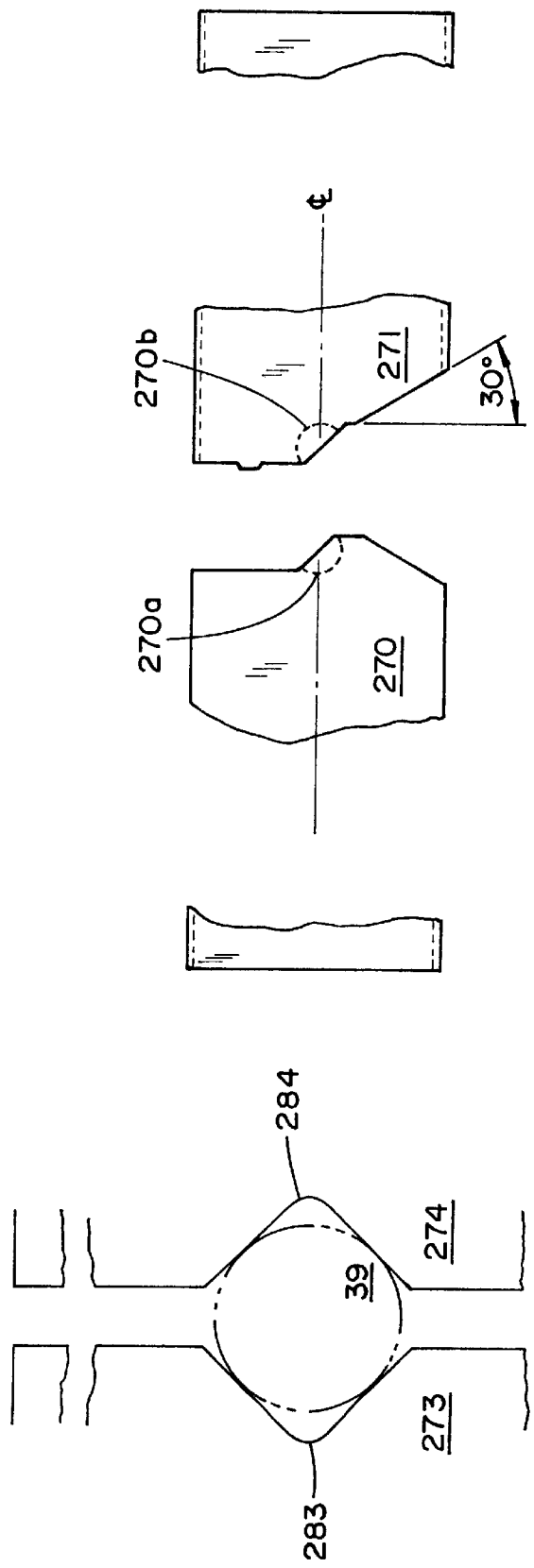

STAND ALONE SWAGE APPARATUS

FIELD OF THE INVENTION

The present invention relates generally to machines for automatically swaging needles, such as surgical needles to a suture, and more specifically, to an apparatus that semi-automatically singulates unsorted needles and automatically swages them to a suture, tests the needle-suture bond, and and then bundles the needle suture assembly for subsequent packaging.

DESCRIPTION OF THE PRIOR ART

This application describes in detail an improvement to a portion of the apparatus disclosed in a series of U.S. Patents, of which U.S. Pat. No. 5,438,746 entitled "Needle Threading and Swaging System"; and U.S. Pat. No. 5,473,810 entitled "Needle-Suture Assembly and Packaging System" are typical. All of these patents are assigned to the assignee of the present invention.

The automatic needle and suture threading machine described in the above referenced U.S. Patents is a highly automated machine intended for high volume production and packaging of needles and sutures wherein 20,000 to 40,000 needles and sutures are to be produced in a single run.

SUMMARY OF THE INVENTION

The present application describes an improved semi-automatic needle singulation and swage dial assembly for the swaging of needles to sutures fed and cut to length by the apparatus, together with improvements in the operation of the apparatus The present invention is directed to improvements for a stand alone swage machine that is particularly adapted to assist in the semi-automated singulation of surgical needles to enable subsequent automated handling of the needle, automatic swaging, automatic pull testing of the combined needle and suture (armed sutures), and bundling of the armed sutures for future packaging.

It is an object of the present invention to provide a machine which will efficiently handle small batches or production runs on needles and to efficiently handle premium needles and super sharp cutting edge needles in an efficient manner without blunting the cutting edge of the needle, while bundling the same for future packaging.

It is another object of the present invention to provide a machine which is flexible in operation and enables quick changeovers between production lots and which minimizes the number of change parts required to migrate from one size needle or suture to another.

It is another object of the present invention to provide a machine which will handle odd runs or "doctors' specials" as they are referred to in the trade, where a particular surgeon expresses a preference for an unusual combination of needle type or size and suture material.

It is an objection of the present invention to provide a needle singulating apparatus for assisting an operator in singulating needles for an automatic swaging machine, wherein the apparatus includes a a needle sliding surface, a pair of drop openings for receiving the singulated needles, and means to position the singulated needles in a spaced apart relationship on an indexing conveyor for transport to a precise positioning apparatus. The precise positioning apparatus then positions the needle at a first predetermined position for hand-off to an automatic swaging apparatus.

It is another object of the present invention provides a method and means for precise positioning of the needle during the hand-off to a precision universal gripper than will grip the needle and hold it during suture insertion. High precision is necessary in the later stages of the present invention, or the sutures can not be automatically inserted into the needle barrel in the subsequent swage operation.

The position and orientation data must be determined for a wide size range of needles, since the curved portion of the needles varies by more than 100% in one dimension, and over a half inch in the other dimension. These variances must be reduced to an accuracy of 0.001 before hand-off of the needle to the swage operation.

In addition to the accuracy of positioning, a correct orientation must be determined. To a convention vision systems the needles appear as arcs with similar ends. However, it is vitally important to determine with the vision system, which end is the barrel end and which end is the sharp end, or the subsequent swage operation will fail.

It is another object of the present invention to provide a plurality of universal grippers mounted on a rotating swage dial for successively receiving an individual one of a plurality of precisely positioned needles at a first predetermined location and indexing each of said individual successive needles in a predetermined orientation from said first predetermined location through successive locations for sequential processing at subsequent predetermined locations, each of said universal grippers having a cam follower which cooperates with a cam dial to provide radial reciprocation of the universal grippers with respect to said swage dial in response to rotation of said cam dial. The machine includes a swage dial and a cam dial mounted for rotation about a common first axis of rotation, with the swage dial supported by and mounted for rotation on a first drive shaft which rotates about this single first axis of rotation. This first drive shaft is driven by said first intermittent drive to provide intermittent advancement of the swage dial.

It is another object of the present invention to provide an automatic stand alone swage apparatus with an improved swage dial having an off set motion for the universal grippers that enables the universal grippers to place and retrieve needles held in a swage device having a swage die opening formed in a fixed swage die and to provide universal grippers which are rotated by said swage dial to each of said predetermined locations and reciprocated in and out of an operative position by said cam dial at each of said plurality of predetermined locations while simultaneously being offset so as to be able to place and retrieve needles held in a swage device having a swage die opening formed in a fixed swage die.

It is an also an object of the instant invention to provide a stand alone swage apparatus with an automatic pull-test system that can automatically perform minimum pull-testing of the needle-suture assembly in a cost-effective manner and without manual intervention.

Furthermore, it is an object of the present invention to provide an automatic swage apparatus in combination with an automatic pull-test system, wherein the needle-suture assembly is automatically indexed to an automatic pull-test station after the suture has been cut and swaged to the surgical needle wherein the pull-test apparatus includes a first gripping means for use in non-destructive testing and a second gripping means for use in destructive testing of the needle-suture assembly.

Still another object of the instant invention is to provide an automatic pull-test system that can perform a destructive pull-test of a needle-suture assembly and retain the maximum pull-test values thereof for statistical analysis thereof and for statistical process control and that can provide automatic adjustment of the upstream swaging dies used to produce the armed needle in accordance with statistical process control values.

Finally, it is an object of this invention to provide a rotating array of needle collection buckets that enables collection of a predetermined number of needle and suture assemblies (armed sutures) that are bundled by the present machine for subsequent packaging in machines such as that typified by U.S. Pat. No. 5,487,212 or the machine described in U.S. Pat. No. 5,664,404 entitled "Single Suture Automated Packaging Machine", both of which are assigned to the assignee of the present invention.

BRIEF DESCRIPTION OF THE DRAWINGS

FIG. 7(a) is a top plan view of the needle singulating station of the present invention.

FIG. 7(b) is a partially cross-sectioned elevation view of a portion of the needle singulating station illustrated in FIG. 7(a).

FIG. 9(a) is a partially cross sectioned elevation view of one of the conveyor "boats" used by the precision conveyor of the present invention, with the jaws thereof in an open position.

FIG. 18(a) is detailed top view of the cam dial assembly 120 having cam dial plate 125 with cam follower 165a in a retracted position within cam track 160a.

FIG. 18(b) is top view of the cam dial plate 125 showing cam follower 165a in an extended position within cam track 160a.

FIG. 21(a) is top plan view of the universal gripper and slide assembly used in the present invention, illustrating in dotted lines the various operating components thereof.

FIG. 21(b) is partially cross-sectioned side view of the universal gripper and slide assembly illustrated in FIG. 21(a).

FIG. 21(c) is a partially hidden front view of the universal gripper illustrated in FIG. 21(a) illustrating in dotted lines the actuating mechanism used to open the jaws of the universal gripper.

FIG. 24 is a partially cross section top view of the needle stripper assembly used in the present invention.

FIG. 25 is an elevation view of a needle bucket for the needle bundling station, illustrating radial reciprocation of the needle bucket used in the present invention.

FIG. 25(a) is a front view of the needle bucket for the apparatus illustrated in the elevation view of FIG. 25.

FIG. 25(b) is a top view of the needle bucket for the apparatus illustrated in the elevation view of FIG. 25.

FIG. 26(a) is a top plan view of the fixed and moveable swage dies of the present invention.

FIG. 26(b) is an enlarged view of a portion of the apparatus illustrated in FIG. 26(a) with a needle positioned therein before swaging.

FIG. 26(c) is a top plan view of portions of the suture guides of the present invention.

FIG. 29(a) is an elevation view of the load cell assembly of the present invention, illustrating the v-plate needle arm.

DETAILED DESCRIPTION OF THE PREFERRED EMBODIMENT

The present invention is directed to improvements in a stand alone swage machine that is particularly adapted to assist in the semi-automated singulation of surgical needles to enable subsequent automated handling of the needle, automatic swaging, automatic pull testing of the combined needle and suture, and bundling for future packaging.

The present application describes improvements in the swaging assembly that swages needles to sutures, together with improvements in the operation of the apparatus. The present invention enables the swaging of needles in symmetric dies, even when one of the dies is fixed in position.

This application describes in detail an improvement of a portion of the apparatus disclosed in U.S. Pat. No. 5,473,810 entitled "Needle-Suture Assembly and Packaging System" and U.S. Pat. No. 5,473,854 entitled "Machine for the Automated Packaging of Needles and Attached Sutures and Method of Utilizing the Packaging Machine," both assigned to the assignee of the present invention. The present invention includes an improved drive train for the swage dial which is similar to the swage dial used in the machine described in the aforesaid patents.

The automatic needle and suture threading machine described in U.S. Pat. No. 5,473,810 is a highly automated machine intended for high volume production and packaging of needles and sutures wherein 20,000 to 40,000 needles and sutures are to be produced in a single run.

The machine described in this application is designed to efficiently handle small batches or production runs on needles and to efficiently handle premium needles and super sharp cutting edge needles in an efficient manner. It is intended to provide flexibility in operation and a quick changeover between production lots and to minimize the number of change parts required to migrate from one size needle or suture to another.

The present invention is also intended to handle odd runs or "doctors' specials" as referred to in the trade, where a particular surgeon expresses a preference for an unusual combination of needle type or size and suture material.

Needle and suture assemblies (armed sutures) are swaged by the present machine for subsequent packaging in machines such as that typified by U.S. Pat. No. 5,487,212 or the machine described in U.S. Ser. No. 521,831, entitled Single Suture Automated Packaging Machine, both of which are assigned to the assignee of the present invention.

Figure 2:
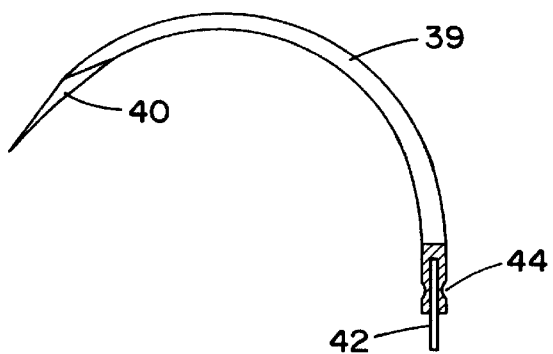
FIG. 2 is a diagrammatic view of an edged needle that is typical of the needles to be singulated and swaged according to the present invention.

The present invention minimizes the handling of the needle and is therefore particularly adapted for the automated handling of premium needles and cutting edge needles such as the needle illustrated in FIG. 2.

As illustrated in FIG. 2, the needle 39 includes a ground or cutting edge portion 40 and is illustrated with an attached suture 42 which has been attached by swaging as indicated at 44. The suture 42 may be of any predefined length, but is commonly provided in lengths that are multiples of nine inches (18, 27 and 36 inch suture sizes are particularly common).

Figure 1:
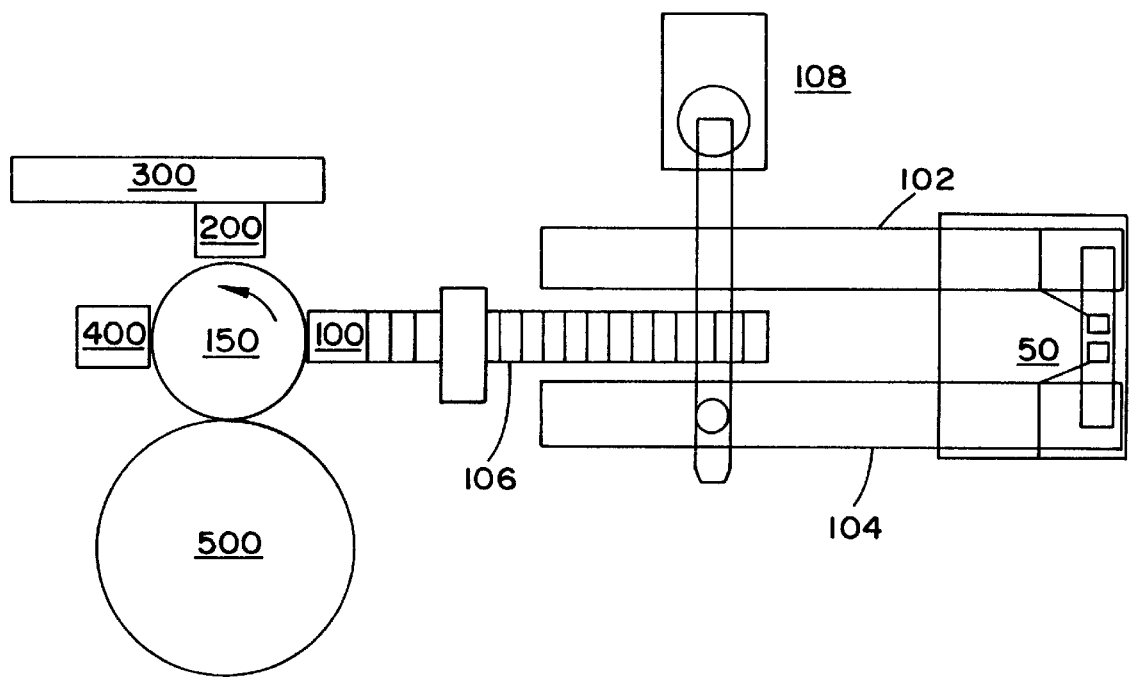
FIG. 1 is a diagrammatic top view of the needle threading and swaging system incorporating a semi-automatic needle sorting and singulating table for feeding individual needles to a universal gripper mounted on a rotary swage dial, an automatic swaging station, an automatic pull-test station, and an armed suture off-load and bundling station.

Generally, in the needle threading and swaging system of the present invention, parallel operations take place simultaneously at a plurality of different stations to ensure that approximately forty to sixty (40–60) armed surgical needles are assembled and discharged per minute. For instance, as shown in FIG. 1, a semi-automatic needle sorting and singulating station 50 assists an operator in sorting and singulating individual needles to a pair of translucent indexing conveyors 102,104 where the singulated needles are imaged by a vision system, selected by a computer, and transferred from the translucent indexing conveyors 102,104 to a precision indexing conveyor 106 by a robotic gripper 108. The precision indexing conveyor conveys precisely oriented surgical needles to a precise positioning station 100 to be sequentially received by a plurality of grippers mounted on the rotary swage dial 150. The rotary swage dial then rotates counter-clockwise as shown by the arrow in FIG. 1, to index each needle to the automatic swaging station 200 where the suture material is cut, inserted into the needle, and automatically swaged thereto. A suture drawing and cutting station 300 pulls, tips, cuts and inserts the suture into the needle to be swaged. The needle is swaged and then, the rotary swage dial 150 rotates to index the armed suture to the automatic pull-test station 400 where each armed needle is pull-tested to ensure that the minimum and/or destructive pull-test requirements of the medical profession, are met. Finally, the rotary swage dial indexes the pull-tested armed needle to the off-load station 500 where the surgical needle and suture assemblies are handed off for suture bundling for subsequent packaging at another location.

Figure 3A:
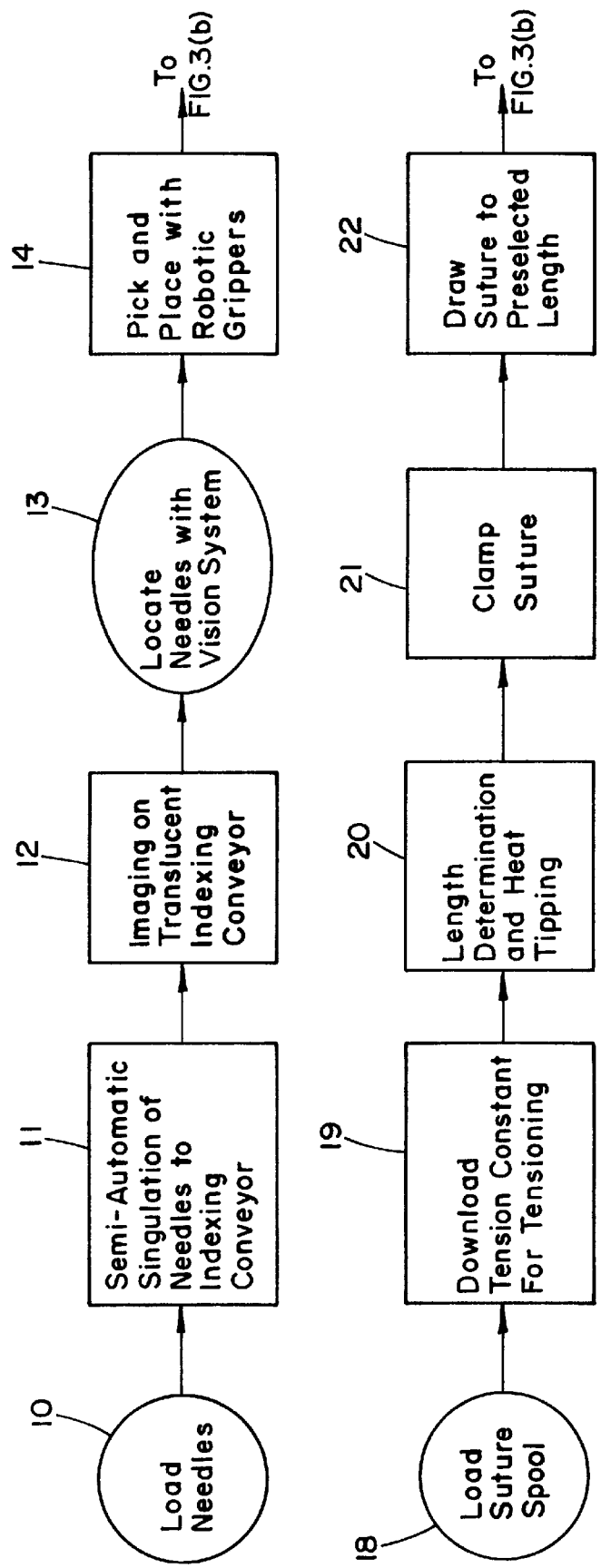
FIGS. 3(a) through 3(c) form a flow diagram illustrating the process for the needle threading and swaging system of the present invention.
Figure 3B:
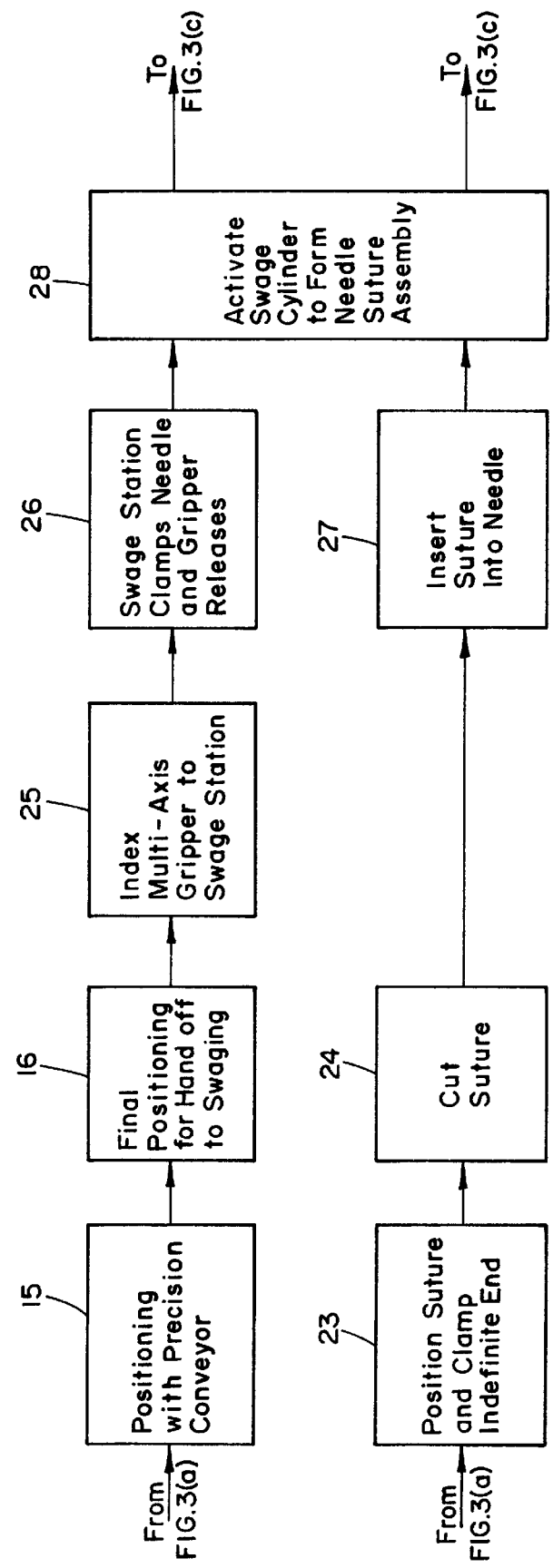

FIGS. 3(a) and 3(b) are block diagrams which illustrate the automatic needle threading and swaging process of the instant invention. For instance, at the needle singulating station 50, needles are first loaded onto a flat operator work surface at 10, singulated by the operator, and then automatically and individually fed at step 11 to one of the translucent indexing conveyors 102,104. The needles are imaged at step 12 and then evaluated with respect to orientation and position by a vision tracking system at step 13, picked up by a robot apparatus at step 14, transferred to a precision conveyor 106 for positioning by the robot apparatus 108 at step 15, and finally conveyed to a load station 100 where the needles are precisely positioned at step 16 and transferred to a universal gripper located on a rotary swage dial 150 for subsequent transfer to the swaging station 200 indicated at step 25. A detailed explanation of the apparatus used to carry out each step will be explained in further detail hereinbelow.

Figure 3C:
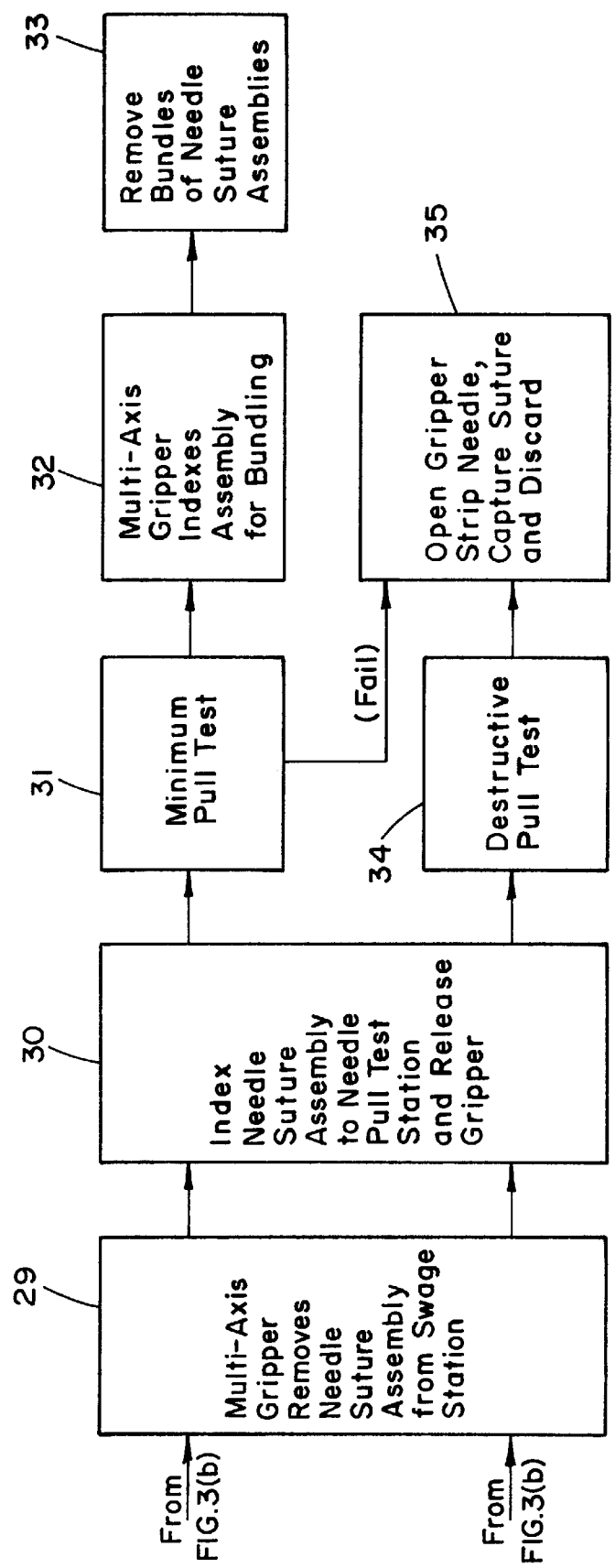

Simultaneous with the needle sorting process described above with respect to steps 10 through 25, an automatic suture cutting process takes place at the suture station 300 as shown in FIGS. 3(*a*) through 3(*c*) with respect to steps 18 through 28. Indefinite length suture material is supplied in various spools and configurations that may carry up to 5000 yards of material. This is indicated at step 18 in FIG. 3(*a*), where the suture material is loaded into a payoff assembly. A tension constant for the suture to be drawn is downloaded as indicated at step 19. A drawing tower apparatus includes grippers that alternately draw lengths of the suture material from the spool to enable cutting thereof which lengths are predetermined at step 20.

While the material is being drawn, it may require extra treatment or processing. For instance, as described in detail below, it may be desirable to heat the suture material under tension at the area which will become the suture tip in order to stiffen the material to facilitate the positioning thereof within the suture receiving opening of a surgical needle. Thus, at step 20, heat may be applied to a portion of suture material. In the preferred embodiment of the invention the heating step is performed upstream of the drawing and cutting apparatus to enable the suture to partially cool and harden before cutting. At step 21 of the block diagram of FIG. 3(*a*), the suture material is clamped and gripped by the servo grippers, and at step 22, the suture strand is drawn to a predetermined length and positioned for insertion within the suture receiving opening of the needle for swaging as illustrated in FIG. 3(*b*). As the suture is positioned for insertion, a second suture clamps the suture at a position which will hold the indefinite length end at step 23, and the suture is cut at step 24 to separate the suture of predetermined length from the indefinite length suture.

After a surgical needle is indexed to the swaging station 200 as described above, the universal gripper positions the needle in a precisely oriented position at the swage die opening formed at the ends of two swaging dies of a swage assembly as indicated as step 26 in FIG. 3(*b*). Simultaneously, the suture strand is drawn along a suture axis to register a tip thereof for insertion within the suture receiving end of the needle. Next, at step 27, the gripper assembly at the drawing tower inserts the tip of the suture strand within a lower funnel guide for accurate positioning within the suture receiving opening of the needle that is aligned with the suture drawing axis. At step 28, the swage cylinder is activated to automatically swage the suture to the needle. The universal gripper is actuated to grip the needle, and then retracted on the rotary swage dial as shown in FIG. 3(*c*) as step 29 and indexed to a pull-test station 400 at step 30 so that minimum pull-testing at step 32 or destructive pull-testing at step 34 may be performed.

Depending upon the results of the minimum pull-test, the needle and suture assembly will either be indexed by the rotary swage dial to the off-load station 500 where the armed needle will be bundled if the pull-test requirements are met (as shown as step 32 in FIG. 3(*c*)), or, will be discharged at the pull-test station if the needle fails the minimum pull-test (as shown as step 35 in FIG. 3(*c*)). The destructive pull-test always renders the needle incapable of further processing so the needle is automatically discharged at the pull-test station 400 as indicated at step 35 in FIG. 3(*c*). Finally, as shown as step 33 in FIG. 3(*c*), needle and suture assemblies passing the minimum pull test are conveyed to an off-load station 500 where the individual armed sutures are bundled for subsequent packaging and sterilization.

A detailed explanation of the apparatus used to carry out each step in the suture cutting process will be explained in further detail hereinbelow.

Overview of the Apparatus

Figure 4:
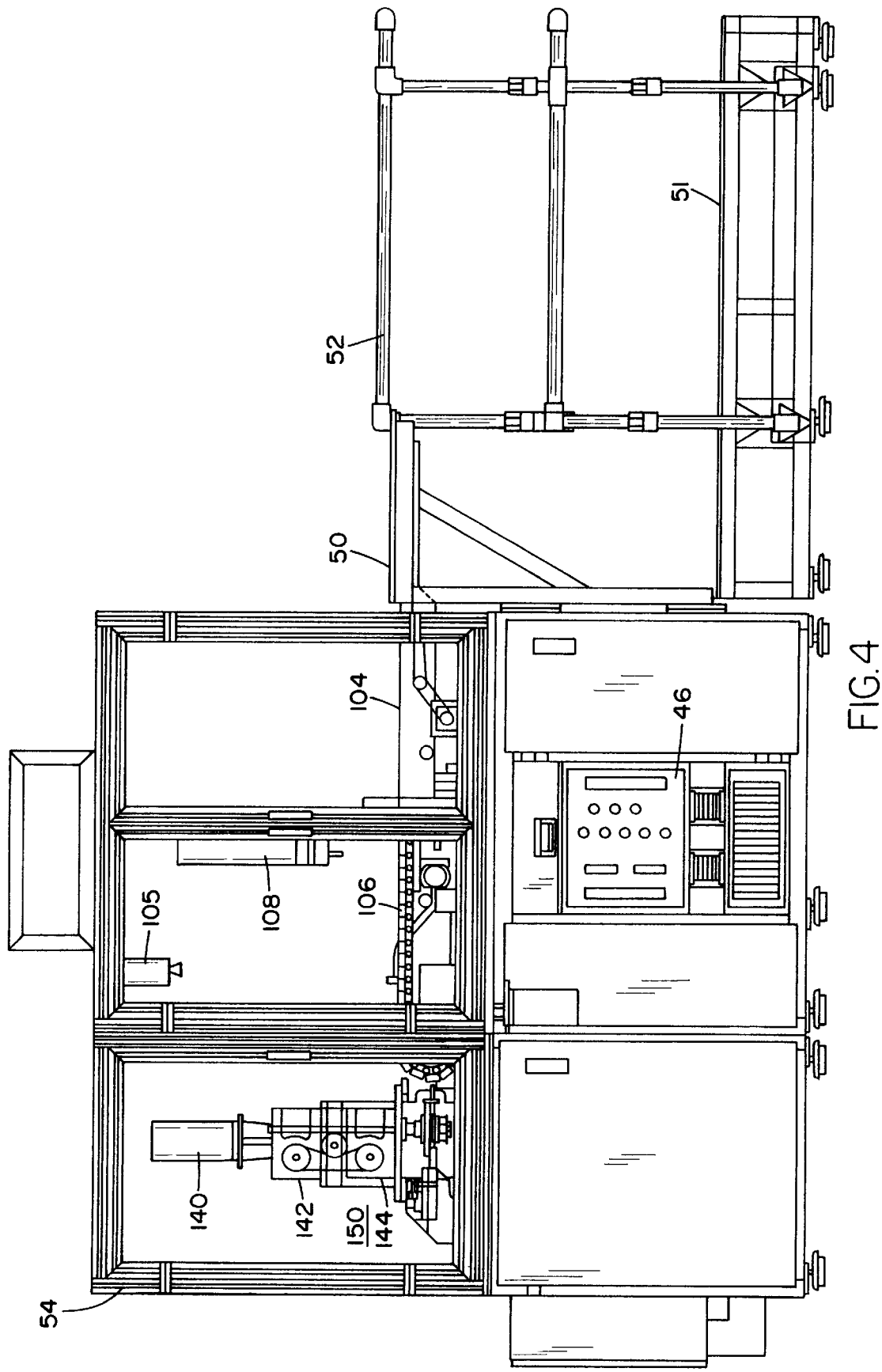
FIG. 4 is an elevation side view of the present invention illustrating an operator station, a control computer, portions of the robotic handling device, and the swage drive of the present invention.
Figure 5:
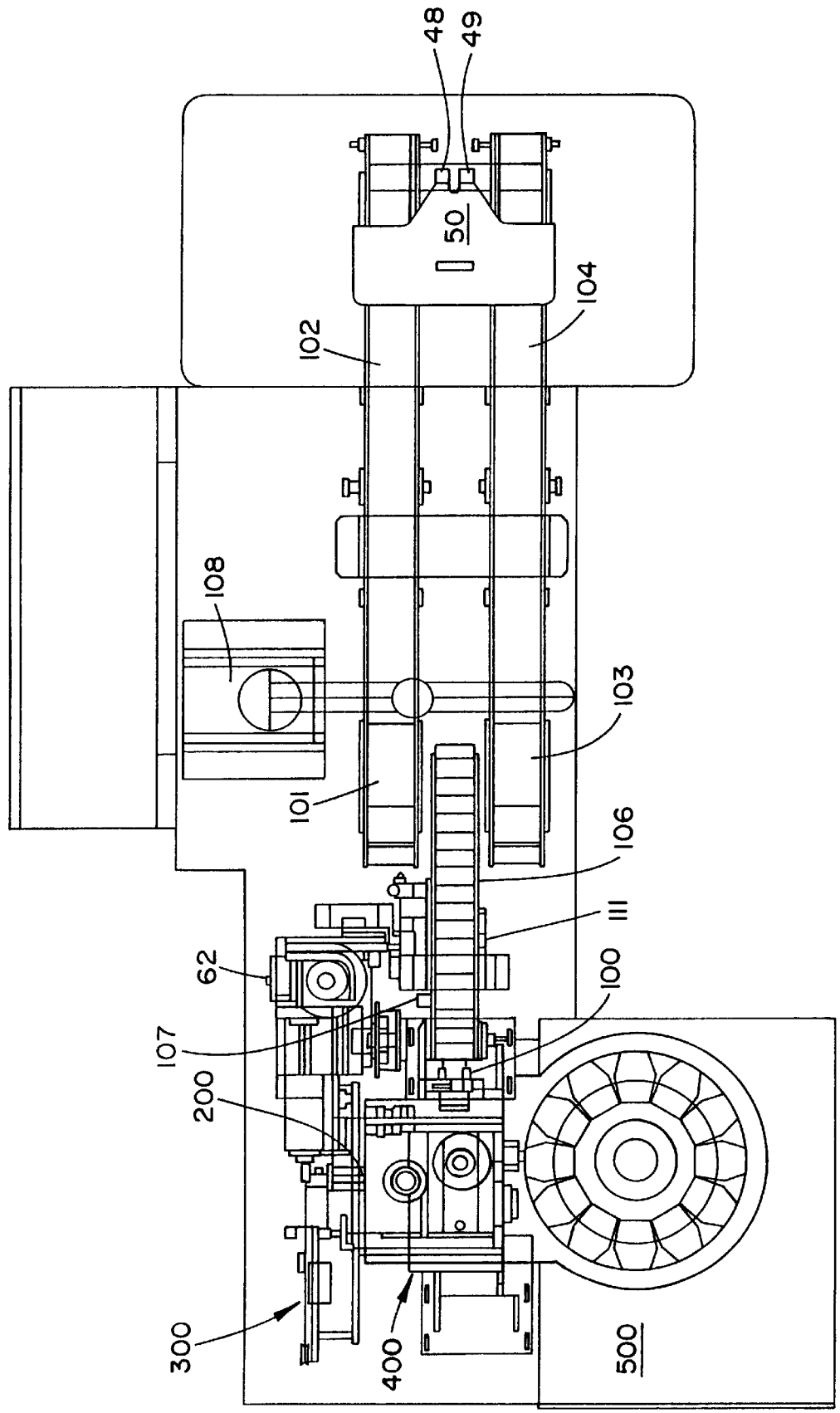
FIG. 5 is a top plan view of the present invention with the operator safety guards illustrated in FIG. 4 removed.
Figure 6:
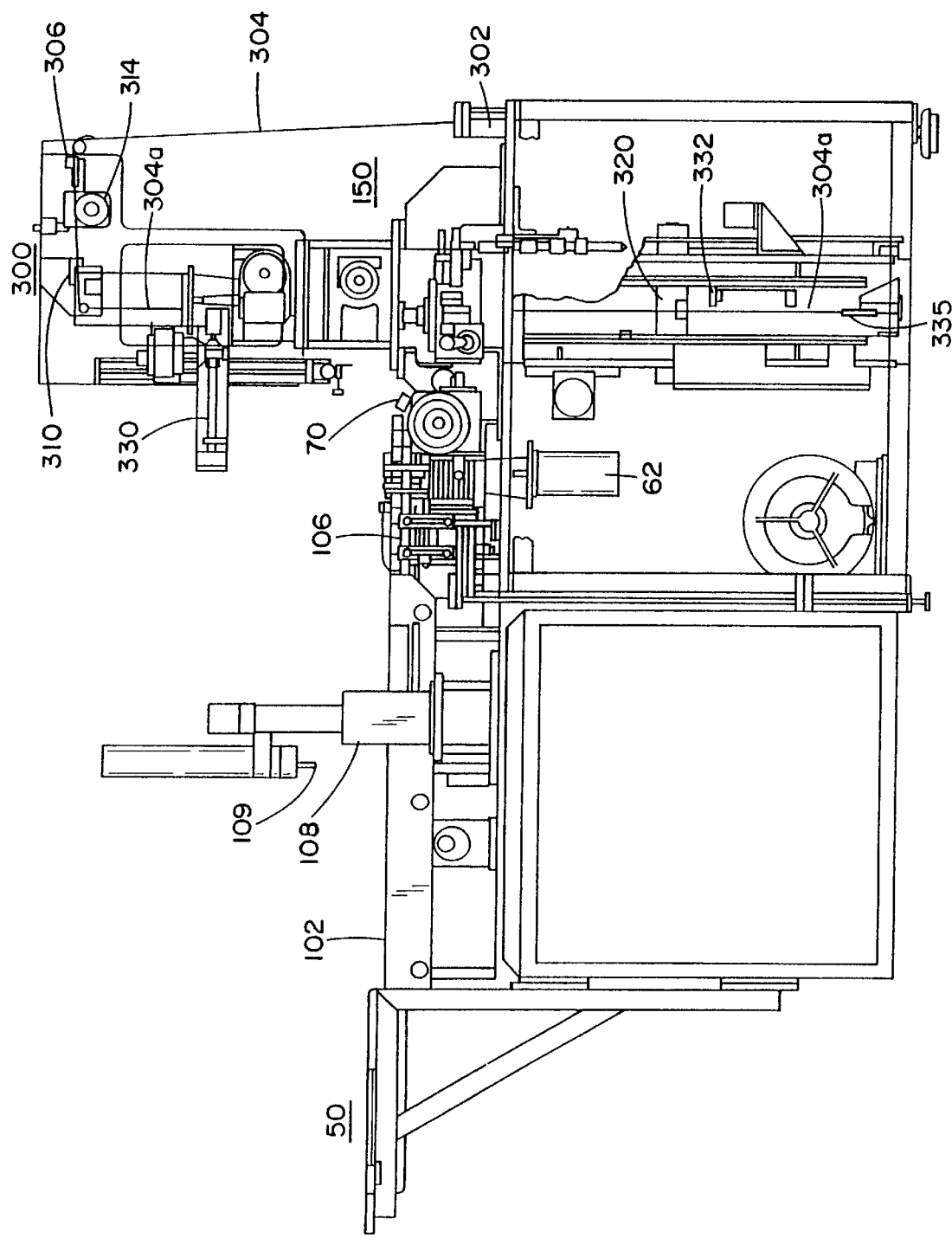
FIG. 6 is a detailed elevation side view of the present invention from the opposite side as illustrated in FIG. 4, with the operator safety guards removed.

FIG. 4 is an elevation view of one side of an apparatus constructed according to the teachings of the present invention, and FIG. 5 is a top plan view of the apparatus with the safety guards removed. FIG. 6 illustrates the apparatus from the opposite side as FIG. 4. FIGS. 4–6 are used in the following descriptive overview of the apparatus. This apparatus includes a singulation surface 50 on table 53 to assist an operator in singulating needles that are deposited to the translucent conveyors 102,104, one of the conveyors 104, being depicted in FIG. 4. The operator work station includes a platform 51 for operator seating and guard rails 52 for operator safety. Safety guards 54 are also provided around the machine for safety purposes.

Each of the needles singulated by the operator are dropped through openings 48,49 by sliding the needle along the singulation surface 50. This step avoids the needle to needle contact inherent in the vibratory feed bowls illustrated in U.S. Pat. No. 5,473,810 and thus substantially reduces the risk that premium needles or cutting edge needles will be blunted by needle contact. As each needle is dropped, it lands at an intermediate staging location, and at an appropriate interval, after each index of the indexing conveyor, the needles is blown by a puff of air to the translucent indexing conveyor, with needles dropped through opening 48 being transferred to translucent indexing conveyor 102 and needles being dropped through opening 49 being transferred to translucent indexing conveyor 104.

The needles thus transferred are indexed forward to imaging stations 101,103 wherein a back light provides a high contrast image of the needle against a white background for imaging purposes. The indexing conveyors 102,104 are indexed approximately 2 inches at each index. By limiting the incremental advancement the image processing is step is enhanced, and problems associated with inertial loads on the needles on conveyors 102,104 are minimized. If the indexing conveyors 102,104 are accelerated too quickly, the needle will remain in its drop position and not be advanced forward, and conversely, if the needle is moving on the conveyor, and the conveyor is stopped too quickly, the needle will continue to travel after the conveyor is stopped. The present apparatus seeks to avoid either of these situations by minimizing the amount of index at each incremental step while still providing enough movement to provide an adequate supply of needles to the apparatus.

The needle singulating apparatus illustrated provides a single needle at each drop point which substantially enhances the accuracy of the vision system and minimizes needle returns that might otherwise be necessary for overlapping or nested needles that were either not imaged, or selected by the computer control means 39 for transfer by the robotic apparatus 108.

The needles deposited on the translucent indexing conveyor 104 are imaged by a vision system 105 and these images are processed by a computer control means 46 to identify the orientation and X,Y coordinate location of the needles. Determining the X,Y coordinates alone is not enough in the needle swaging environment inasmuch as the robotic apparatus needs to determine, in the case of a symmetrically formed curved needle, which end is the barrel end and which end is the cutting end in order to properly place the needle for subsequent automated handling. After both the orientation and location have been determined, a robotic apparatus 108 picks the needles from the translucent conveyors 102,104 and places them on a precision indexing conveyor 106. The precision conveyor 106 includes a plurality of "boats" 70 which are particularly adapted to provide precision positioning of the needle. The rotary swage dial 150 includes a drive motor 140 and first and second indexing transmissions 142,144 which are used to drive the swage dial in a manner as will be hereinafter explained in detail.

The needles transferred by the robotic apparatus 108 are transferred so that the butt end of the needle 44 is engaged by gripping jaws on the conveyor boats 70 of the precision conveyor 106. While the butt end is located and gripped by the robotic apparatus 108, at the point of pickup it may be oriented in either direction of curvature. For particularly small needles a fixed post may be provided for the robotic apparatus to use in correcting the orientation of curvature. For larger needles, a needle plow 111 is used so that the direction of curvature for each of the needles is uniform. As illustrated in FIG. 5, the apparatus also includes a prepositioner 107 which is adapted to approximately locate the butt end of the needle and an moveable hard stop assembly at station 100 that precisely registers the butt end of the needle to an accuracy of 0.001 inches.

After the needle has been received at the precise positioning station 100, it is gripped by one of the universal grippers located on the swage dial mechanism 150 to be indexed through a plurality of stations including a swage station 200 wherein a suture of definite length is cut from a suture spool of indefinite length at station 300 and inserted into the needle at swage station 200 for permanent assembly thereto. After swaging, the needle is advanced to the pull-test station 400 for testing of the needle suture bond, and then indexed to a bundling station 500 wherein a plurality of buckets are circumferentially arranged on a rotating turntable to receive a predefined number of needles and sutures in each bundle.

Figure 20:
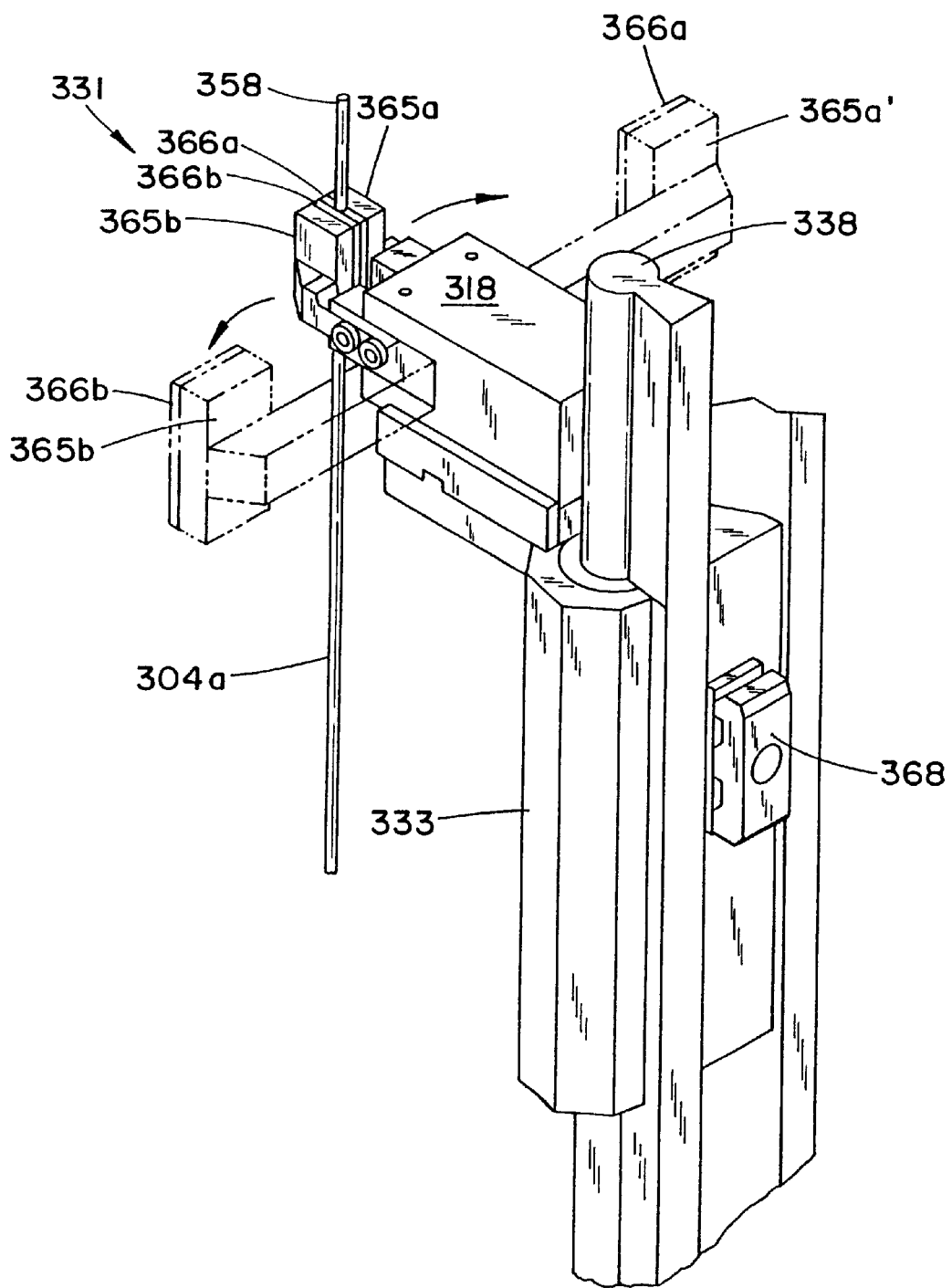
FIG. 20 is an enlarged isometric view of a suture gripper assembly having gripper arms shown in their open (dotted lines) and closed (suture gripping) positions.

FIG. 6 illustrates the apparatus of the present invention from the opposite side of the machine illustrated in FIG. 4 and includes breakaway portions to more particularly illustrate portions of the precision conveyor apparatus and the suture drawing and cutting station 300. As illustrated in FIG. 6, a spool of suture material 302 is mounted on a convenient location and the indefinite length suture material 304 is fed to the suture drawing station through a pretensioning apparatus 306, a tensioning roller 314 having a computer controlled tension constant which may be selectively downloaded from the computer control means 46 to match the suture material 304 being handled, and a knot detector 310 which may be used to provide a knot presence signal to the control computer 46 to reject that length of suture after swaging to a needle. From the knot detector 310 the suture strand 304a is fed through a tipping station 330 which heats the suture strand to a predetermined temperature to assist in tipping and cutting the suture for insertion into the surgical needle. From the heating and tipping station 330, the suture material is passed to the bottom of the machine to a turnaround roller 335 where it is grasped by first and second suture clamps which advance the suture material 304a in a hand over hand manner. As illustrated in FIG. 20, clamp 331 includes a traveling carriage 333 which reciprocates up and down frame member 338 by means of a timing belt which is secured to the carriage at 368. A pneumatic actuator 318 includes first and second clamps 365a,365b and first and second gripping surfaces 366a,366b which clamp the suture material therebetween.

In a first cycle of operation, clamp 331 draws the suture of indefinite length to a suture insertion point immediately adjacent the swage plates of the swaging station and then dwells while a second suture clamp clamps the indefinite suture length below the suture cutter 334 (illustrated in FIG. 15). After the second suture clamp has engaged the suture, the cutter 334 is actuated to cut the suture and the tip end of the suture 358, illustrated in FIG. 20 is inserted into the needle as illustrated in FIG. 22(b). The tip end of the suture 358 is positioned below a funnel dye formed in suture alignment plates 270,271 which reciprocate immediately below swage plates 273,374. After the suture tip end 358 has been inserted into the barrel end 44 of needle 39, the swage station is actuated driving the swage plate 273 against swage plate 274 to swage the suture tip 358 in the surgical needle 39.

Semi-Automatic Needle Singulation

The needle singulation apparatus, the operation of the indexing conveyors 102,104, the robotic apparatus 108, the precision conveyor 106 and the moveable hard stop will be described with respect to FIGS. 7 through 12.

Referring to FIGS. 7(a), (b), the semi-automatic needle singulation apparatus includes a singulation or needle sliding surface 50 on table 53 which assists an operator in singulating needles that are deposited on the table surface in bulk. While it is well known that it is difficult to pick up a needle from a flat surface, it has been found that an operator may singulate and slide a needle quickly to a drop point, such as needle drop points 48 and 49 to provide a singulation function. These drop points are openings in the singulation surface 50, which open to horizontal channels 55,56 formed in needle block 57, illustrated in partial cross section in FIG. 7(b). Channels 55,56 open to drop openings 58,59 above the translucent indexing conveyors 102,104. When the operator slides a needle to the drop opening 48, it falls a distance of 0.5" to 1.0" to the staging surface of channel 55 immediately under the drop opening 48. It is transferred from the staging surface to the second opening 58 in channel 55 by a puff of air from channel 60. Air channel 60 extends upwardly through the needle block 57 and opens in both directions, with a first opening aligned with channel 55, and a second opening aligned with channel 56. As the translucent conveyor is indexed, a solenoid opens the air supply to air channel 60, creating a puff of air in both directions which blows any needles on the intermediate staging surfaces through the channels, and out the lower openings 58,59 to the translucent conveyors 102,104. The needle block is preferably formed of delrin, although other materials would be suitable, provided the material is not soft enough to let the needle points inadvertently dig in. The semi-automatic singulation avoids needle to needle contact inherent in the vibratory feed bowls illustrated in U.S. Pat. No. 5,473,810 and thus substantially reduces the risk that premium needles or cutting edge needles will be blunted by needle to needle contact.

The semi-automatic operator work station includes a platform 51 for operator seating and guard rails 52 for operator safety. Safety guards 54 are also provided around the machine for safety purposes. CRT supports 61a and 61b are also provided to enable the operator to monitor the automatic operation of the apparatus through suitable computer CRT displays.

As will be hereinafter explained in greater detail, the indexing conveyors are alternately indexed a distance of approximately 2" at every index, and this alternate operation and the close spacing of drop openings 48,49 enable an operator to singulate 30 to 60 needles a minute, so that only a single needle is deposited at each incremental advance of the indexing conveyors 102, 104.

The needles are then advance by the indexing conveyors to imaging stations 101,103 (FIG. 5) to be imaged by the vision system. The robotic and vision control system will be hereinafter described in greater detail with respect to FIG. 8. The individual needles are imaged and data representing both their x,y position and their orientation is obtained by the vision control system. The orientation data is needed since the correct end of the needle must be presented when the needle is handed off for automatic swaging.

As described above, and as illustrated in FIGS. 5 and 6, the robotic assembly 108 is located downstream from the needle singulating station and proximate to both of the translucent indexing conveyors 102, 104 and the precision conveyor 106. In the preferred embodiment described herein, the robotic assembly 108 is an Adept® 90604 4 axis robot capable of accomplishing needle transfers at a rate of approximately 40 transfers per minute as controlled by the robot's corresponding Adept® CC controller. Each robot is a four-axis SCARA (Selective Compliance Assembly Robot Arm) robot comprising four Joints capable of a variety of motion. Robotic grippers 109 are attached to the quill of the robot assembly 108 and are enabled to provide gripping action by pressure supplied from an air cylinder (not shown).

Figure 10:
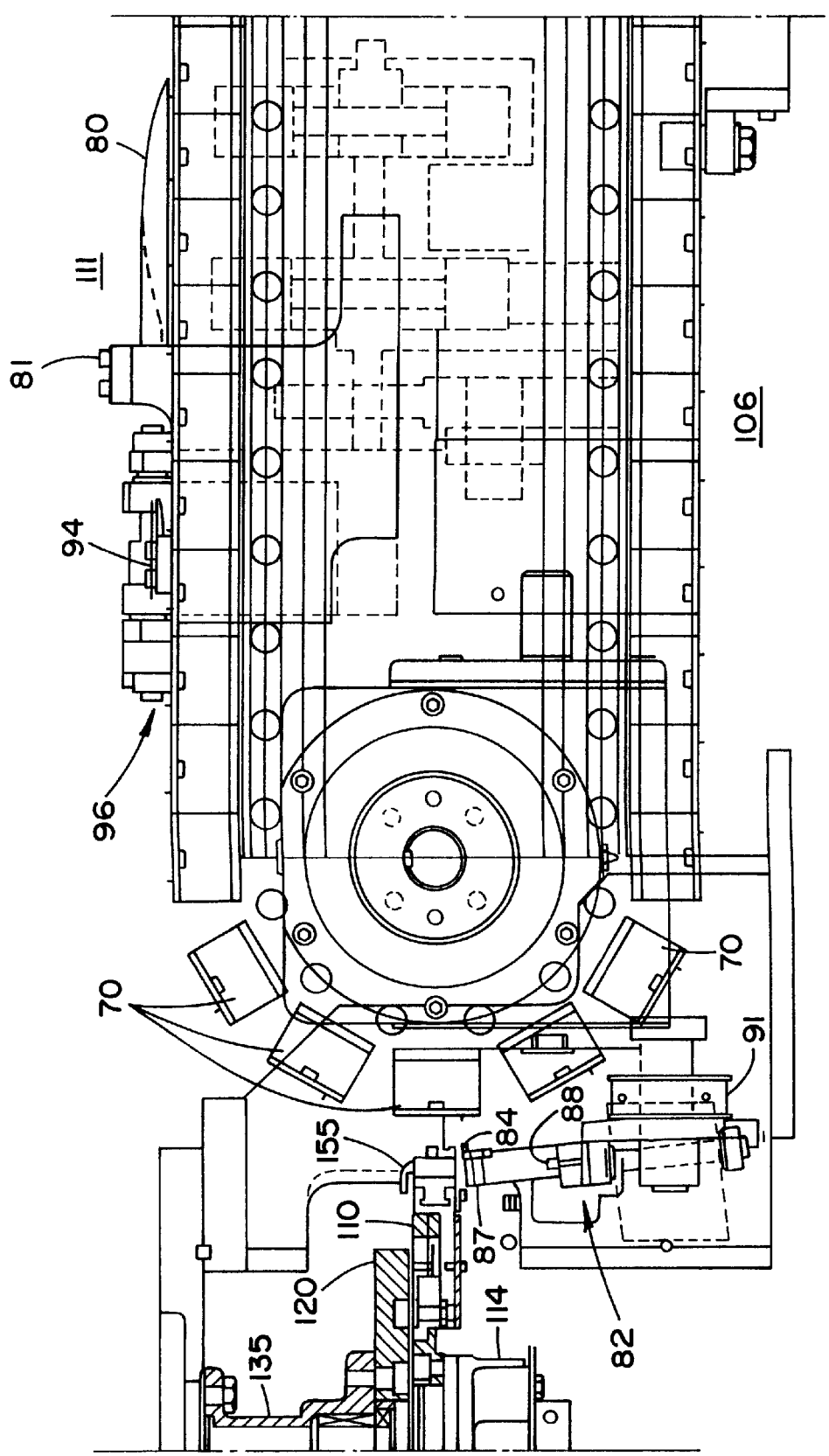
FIG. 10 is a partially cross sectioned elevation view of the precision conveyor of the present invention, illustrating the relative relationships of the precision conveyor, the precision hand off station, the swage dial and the universal gripper used in the present invention.

Referring now to FIGS. 5 and 10, there is illustrated the precision conveyor 106 which is driven by drive motor assembly 62 at a rate sufficient to index and transfer one oriented surgical needle at a rate of up to one per second (1 needle/sec) to the automatic swaging apparatus. A similar drive motor assembly is provided for driving the indexing conveyors 102,104. As will be explained in detail below, each of the drive motor assemblies are interfaced with and operate under the control of the control system 46 to pause the indexing motion to enable the pick-up and transfer of a needle from the indexing conveyor to the precision conveyor.

Figure 9A:
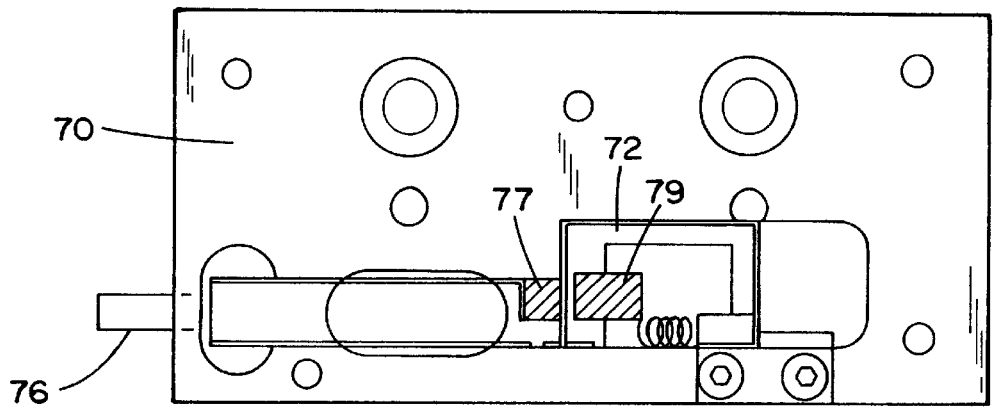
FIG. 9(a) is a partially cross sectioned plan view of one of the conveyor "boats" used by the precision conveyor of the present invention.
Figure 9B:
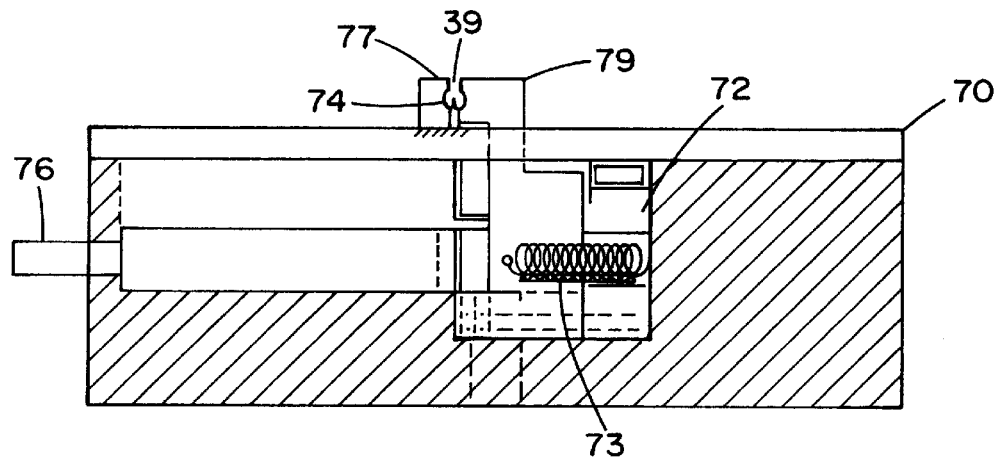
FIG. 9(b) is a partially cross sectioned elevation view of one of the conveyor "boats" used by the precision conveyor of the present invention.
Figure 9C:
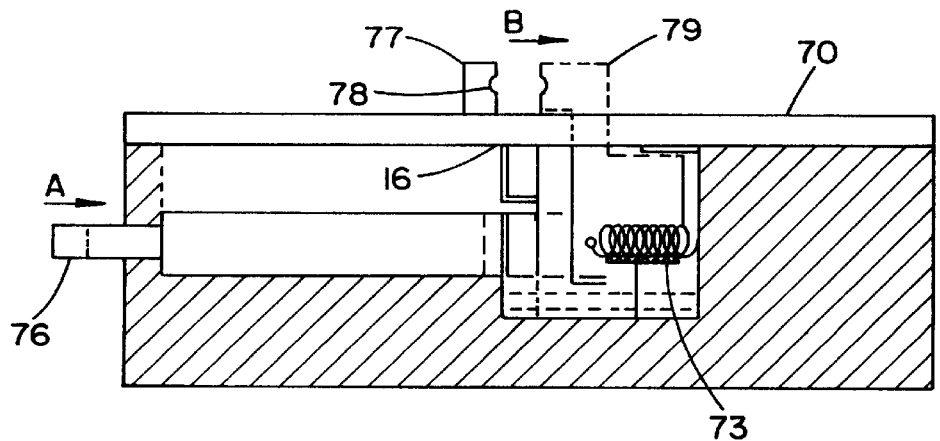

FIGS. 9(*a*), (*b*) and (*c*) illustrate in detail one of the plurality of engagement boats 70 located on precision conveyor 106 for engaging respective individual surgical needles 39. Each boat is preferably provided with a pair of jaws; one jaw 77 being fixedly mounted, and the second jaw 79 being slidable within cavity 72. In operation, a push rod 76 is pressed in the direction of the arrow "A" shown in FIG. 9(*c*) to compress spring 52 which retracts the position of the movable jaw 79 in the direction indicated by the arrow "B" to allow for placement of needle 39 within the notch 78 of both jaws. Normally, spring 73 is biased as shown in FIG. 6(*b*) to maintain movable jaw 79 in its engaged position for retaining a needle 39 in the notch 74. It should be understood that any type of releasable engaging mechanism may be provided for releasably retaining a needle 39 on conveyor boat 70, provided that each needle be correctly oriented on its respective boat for subsequent swaging to take place.

Motion of the precision conveyor 106 is also paused periodically at the desired cycle rate to allow for the transfer of the needles 39 thereto from the robotic assembly 108. In the preferred embodiment, the control system 46 includes a programmable logic controller (PLC) that is in digital communication with the Adept® robot controllers and the vision tracking system components to control the infeed system.

As shown in FIG. 4, the vision tracking system comprises a camera assembly 105 having two video cameras 105*a*, 105*b*, one located overhead each respective illuminated platform portion, 101 and 103, of the indexing conveyors 102,104. As will be explained in detail below, the video images of the needles obtained from each camera 105*a*,105*b* are bit-mapped or suitably digitized and transmitted via suitable transmission or communication lines to the remotely located control system computer 46 where a Vision Control task processes the video images and inputs the data to the robotic assembly 108.

Preferably, the conveyors 102 and 104 are translucent and are backlit at the respective portions 101 and 103 so that a sharp video image may be obtained by the overhead camera assembly for processing. It is understood that for descriptive purposes, only two video cameras 105*a*,105*b* corresponding to the two illuminated platforms 101,103 are shown in FIGS. 4 and 5.

The through-put and redundancy designed into this vision system ensures that there will be no momentary shortage of needles fed to the swaging station and that maximum throughput of oriented needles for input to the swaging station is achieved. Furthermore, a robotic assembly of sufficient speed and precision may, in the future, be able to pick up randomly deposited needles from a moving conveyor and place them directly in an oriented position at the swaging station.

In the preferred embodiment, each camera 105*a*,105*b* is mounted approximately one (1) meter above each backlit indexing conveyor imaging area 101,103 and utilizes an electrically controlled telephoto lens with a focal distance ranging from 10 mm to 140 mm that may be changed with suitable adaptors. Suitable lens controllers are used to establish lighting/iris, focus, and field of view for each camera lens, and, are interfaced with the vision system via an RS-232 link.

A further component of the control system for the needle sorting and infeed apparatus includes an SCADA Node which is used to oversee and direct the infeed system. This node interfaces with each of the Adept® controllers via discrete RS-232 links which are used to download data information, such as needle parameters, error messages, and status messages, to the Adept® controllers. The SCADA node may comprise a personal computer or such suitable device, running commercially available FIXDMACS® software. Serial communication is used to exchange the needle parameters entered at the FIX/DMACS "Adept® Setup" screen during a needle changeover procedure which is used to inform the infeed system of the size and type of needles to be processed. After an operator enters the needle parameters and initiates a changeover, the FIX/DMACS Node will transmit these parameters to the robot controller(s).

The Robotic and Vision Control System

Figure 8:
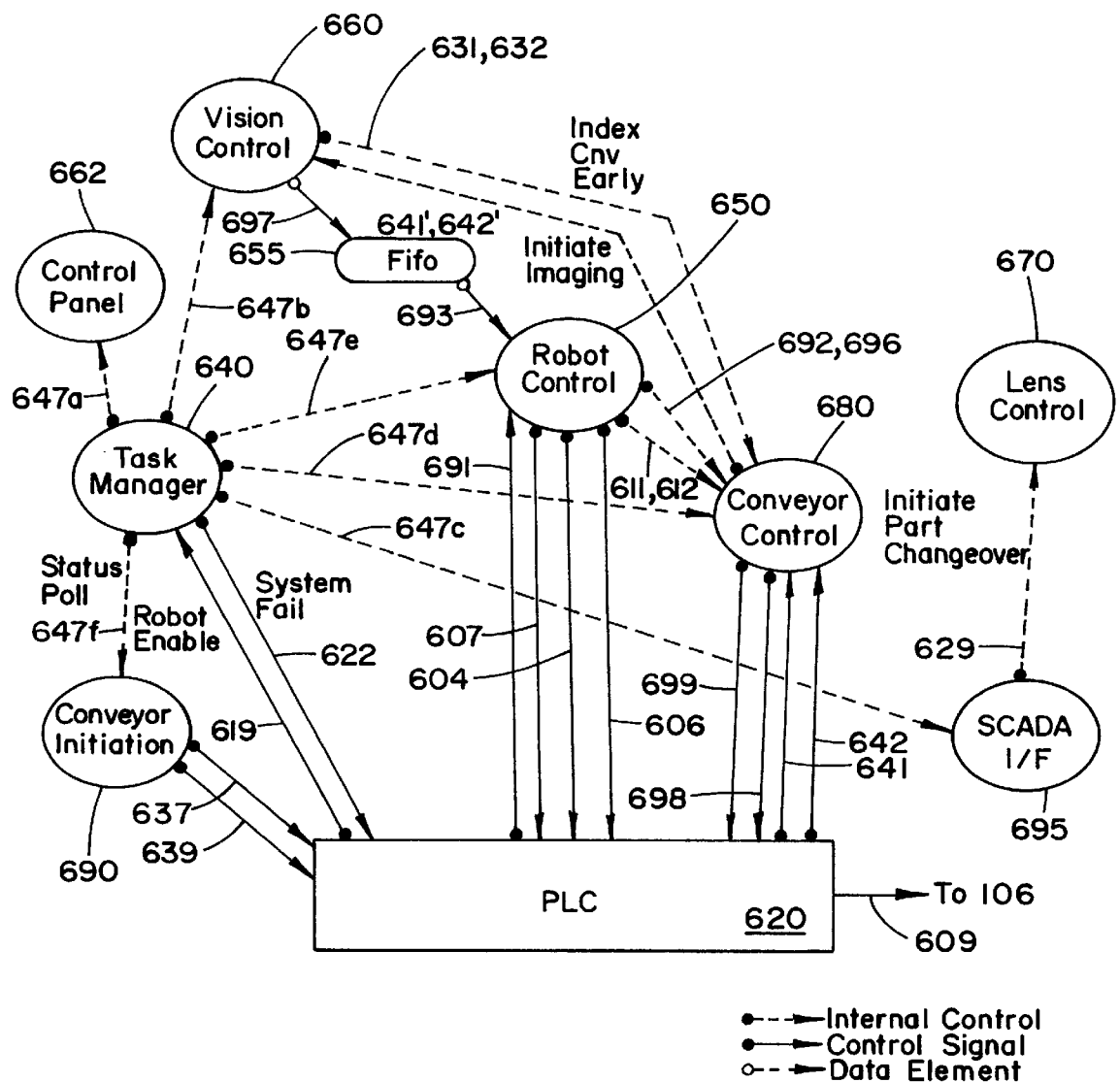
FIG. 8 is a state or task diagram of the imaging system used to obtain position and orientation data of individual needles for the robotic system used by the present invention.

The robotic/vision computer control system of the invention is illustrated in the state or task diagram of FIG. 8. As illustrated, the computer control system comprises individual computer software programs, each associated with a particular task to be performed by various assemblies of the apparatus and executed under the control of the PLC 620. As shown in FIG. 8, the software architecture for controlling the needle sorting apparatus of the instant invention performs eight (8) main tasks: a Robot Control task 650; a Vision Control task 660; a Conveyor Indexing Control task 680; a SCADA Node Interface task 695; A Control Panel task 660; a Task Manager 640; a Conveyor Initiation task 690; and, a Lens Control task 670. Of these eight tasks mentioned above, the first six are active during steady state operation as will be explained below. FIG. 8 additionally shows the data flow among the tasks and the signals which initiate the tasks. It is understood that the software language used in the preferred embodiment, is Adept's V/V+ language, which supports both vision and robotic control in a multitasking environment. A more detailed description of the following tasks can be found in U.S. Pat. No. 5,568,593, also assigned to the assignee of the present application, the disclosure of which is incorporated herein by reference thereto.

It should be understood to those skilled in the art that the robotic assembly, controller, and camera vision tracking system requires calibration and configuration procedures for the system to properly function. For instance, the robotic assembly requires that joint positions be set and joint limits be configured to ensure that the robot avoids structural damage when enabled. Furthermore, a camera-to-robot calibration is required so that the vision system may accurately compute the positional coordinates of the needle so that the robot may move to the pick position. This procedure provides a translation matrix between the camera's field-of-view and the robot base position.

The PLC 620 is responsible for initially powering the robot controller and the robotic assembly. A robot calibration procedure may be initiated after power-up to move the robot joints to known "home" positions to synchronize the digital encoders of the assembly.

The process of starting the PLC 620, robot controllers, indexing conveyors 102, 104 and precision conveyor 106 is time-critical. From the robot controller perspective, when a ROBOT ENABLE signal 619 is raised by PLC 620, it begins its normal cycle by executing the Robot Control Task 650, the Vision Control Task 660, the Conveyor Indexing Control Task 680, and the Conveyor Initiation Task 690; which initiates the movement of indexing conveyor 102, waits approximately up to two (2) seconds, and then initiates the movement of second indexing conveyor 104 as will be described in detail below. Under this scenario, the PLC integrates the startup of the Indexing Conveyors, and swaging machine with the raising of the ROBOT ENABLE signal 619. As will be explained in further detail below, when the ROBOT ENABLE signal goes low, the Adept robot halts its standard processing and responds to requests from the SCADA node.

Robot Control Task

There is a single Robot Control task associated with the Adept® controller for the robotic assembly 108, indicated as element 652 in FIG. 8. The control system software for the Robot Control task 652 manages the robotic assembly 650 as a resource, reads a FIFO buffer 655 of identified needle locations which are produced by and input from the Vision Control Task 660, interfaces with the programmable logic controller (PLC) 620 and control system 46 for needle placement handshaking, and, initiates the indexing of the conveyors 102 and 104.

The steady state operation of the Robot Control task 650 for the robot assembly 108 is as follows. First, the robot controller continuously polls its input FIFO 655 via data line 693 to obtain positional coordinate data for the identified needle locations on a respective translucent indexing conveyor 102 or 104. The data for the needle locations are provided to the FIFO buffer from the Vision Control task 660 via respective data lines 697 as will be explained in further detail below. When an acceptable (recognizable) needle position is entered into the FIFO buffer 655, the robot controller will remove the needle position from the buffer and direct the robot gripper arm 109 to move to that location on the conveyor. Next, for each recognized needle, the Robot Control task 650 will signal the robot gripper 109 to close on the barrel portion 44 of needle 39 and to remove the needle and depart from the conveyor to an approach location proximate the precision conveyor 106. The robot control task then generates a NEEDLE IN GRIPPER signal 607 to the PLC as indicated and waits for a response from the PLC 620. As shown in FIG. 8, when the PLC receives a Robot task generated NEEDLE IN GRIPPER signal 607, the PLC 620 will generate a SAFE TO PLACE signal 691 for receipt by robot 108. The purpose of the SAFE TO PLACE signal 691 is to inform the robotic assembly 108 that a needle may be placed onto a precision conveyor boat 70 of conveyor 106. As a response to the receipt of the SAFE TO PLACE signal 691, the Robot Control task 652 will generate a DON'T INDEX PRECISION CONVEYOR signal 604 for receipt by the PLC 620 immediately before it places the needle on the precision conveyor 106. While this signal remains high, for e.g., at a logic "1" state, the Adept® robot 108 will attempt to place a needle onto a boat 70 of precision conveyor 106. This involves initiating a load solenoid to open the engagement jaws 77,79 of the precision conveyor engagement boat 70 to allow the placement of the needle therebetween, as will be explained below. Once the movement of the robot has settled and a needle is placed, the Robot task 650 will generate a NEEDLE PLACE COMPLETE signal 606 for receipt by the PLC 620 and, the PLC will generate a suitable control signal 609 to enable the engagement jaws of the precision conveyor engagement boat 70 to engage the needle. In the preferred embodiment, the dwell time of the NEEDLE PLACE COMPLETE signal 606 is approximately 48–64 milliseconds. After activating this signal, the robotic assembly 108 will hold the needle in place for the same time period. (48–64 msec.) Immediately thereafter, the robot will open its grippers and move back to its approach location away from the engagement boat 70. Finally, the DON'T INDEX PRECISION CONVEYOR signal 604 is removed indicating that it is now clear for the precision conveyor 106 to index which is performed at the command of the PLC 620.

As a safety interlock for conveyor index initiation, the Robot Control Task 650 will signal the Conveyor Indexing Control Task 680 with an internal control respective LAST PICK signals 692,696 indicating that the robot assembly 108 has picked up the last needle from the current conveyor as indicated in FIG. 8. If the maximum number of needles expected per current camera field-of-view (hereinafter "FOV") is not picked from the respective current infeed conveyor 102, 104, the Robot Control Task 650 will request the Conveyor Control task 680 to index that conveyor belt "early" via the INDEX CONVEYOR 1 EARLY or the INDEX CONVEYOR 2 EARLY signals 611,612 as shown in FIG. 8. Since all signals affecting the motion of the conveyors are routed through the Conveyor Control task 680, this task will generate a corresponding INDEX CONVEYOR 1 EARLY, signal 211 or INDEX CONVEYOR 2 EARLY, signal 212, for receipt by the Adept® robot. If during normal operation the Robot Control Task receives either Index Conveyor 1 Early or the Index Conveyor 2 Early signal, it will flush the contents of its FIFO buffer 655 and continue as if the last needle has been picked from the conveyor.

The control software must take into account the floating 16–32 ms duration of a digital output based on the time slicing of V/V+. This will affect the calculation for minimum time required for placement in conjunction with setting and resetting the Don't Index Precision conveyor signal 604.

The Robot Control Task 650 performs error recovery on two type of errors. These errors are grouped as indexing errors and gross errors. As in all other tasks, gross errors cause the Task Manager 623 error recovery to respond and stop the Robot Control Task immediately. An indexing error occurs if the robot is waiting for a needle to be placed in its parts FIFO and both conveyor belts have not indexed within an appropriate amount of time. This forces the vision/robot control system to flush the contents of its current parts FIFO and index one or both of the conveyor belts 102,104.

Conveyor Indexing Control Task

The Conveyor Indexing Control Task 680 initiates the indexing of each respective translucent indexing conveyor 102, 104 and the task is initiated by the Conveyor Initiation task 690. All signals affecting the motion of the conveyors 102, 104 are routed through the Conveyor Control task 680.

As shown in FIG. 8, the first step of the Conveyor Indexing Control task 680 is to check for the LAST PICK signal 692,696 internally generated from the Robot Control Task 650 and indicating that the last Ineedle pick-up from the respective infeed translucent conveyor 102, 104 has been completed by the Adept® robot 108. Alternatively, the Conveyor Indexing Control task 680 awaits for the INDEX CONVEYOR EARLY (1 and 2) signals 631,632 internally generated from the Vision Control task 660 when no needles are recognized in the current camera FOV. As a result of receiving the LAST PICK signals 692,696 from the robot task, the Conveyor Control task will generate a corresponding INDEX CONVEYOR 1 signal 698, or, an INDEX CONVEYOR 2 signal 699, for receipt by the PLC 620. It is understood that the Adept® robot controller must request the PLC 620 to index a translucent indexing conveyor 102, 104 after picking up the last needle from the respective conveyor. This signal will cause the corresponding conveyor 102, 104 to abort processing and initiate indexing of the belt.

After receipt of both INDEX CONVEYOR 1 or INDEX CONVEYOR 2 signals 698,699 from the robotic assembly, the PLC 620 commands the translucent indexing conveyors 102, 104 to index and generates a corresponding CONVEYOR 1 SETTLED signal 641 or, a CONVEYOR 2 SETTLED signal 642 for receipt by the Conveyor Control Task 680. Note that the CONVEYOR 1 SETTLED signal 641 and the CONVEYOR 2 SETTLED signal 642 are raised approximately 2 seconds after the PLC has been requested by the robot control task 650 to index conveyor 102, 104. The Conveyor Control Task 680 then informs the Vision Control task 660 to begin needle imaging upon receipt of internal control signals 641',642' that correspond to the respective CONVEYOR 1 SETTLED and the CONVEYOR 2 SETTLED signals 631,632. Once the indexing conveyor 102, 104 has been indexed and the corresponding CONVEYOR SETTLED signal 641,642 has been received, the Vision Control Task 660 may begin needle recognition in the corresponding cameras's FOV. Specifically, as will be explained below, the cameras 105, 105a above conveyor 102,104 each take a snapshot of the respective field of views at respective illuminated portions 101,103 of the translucent conveyors and the Vision Control task 660 will control the processing of the image to make a determination of whether a recognizable needle is present each camera's field of view.

At this point, a distinction must be made between the mere presence or detection of a needle in the field of view and the presence of a "recognizable" needle. A needle may be present, but, for a variety of reasons, the Vision Control Task 660 may not be able to determine its positional coordinates until the camera vision parameters are changed by the execution of an auto-imaging algorithm which automatically adjusts the iris and vision system lighting parameters of each camera so that the cameras may subsequently obtain enhanced images that may be processed. During steady state, when the vision task has already "recognized" a needle in its respective field of view, the auto-imaging algorithm is not repeated. Details of the auto-imaging algorithm will be explained in detail below.

Vision Control Task

The Vision Control Task 660 controls and processes the images taken by each of the two camera assemblies 105, 105a. Since the timing of the two translucent conveyors are phased, only one camera is operating at one time.

Specifically, as shown in FIG. 8, the Vision Control task 660 interfaces with each respective camera 105,105a to identify the needle locations of recognizable needles in that camera lens's respective field of view encompassing an area located at respective illuminated platforms 101,103. The Vision Task 660 then processes the positional and orientation information of the identified needle locations and writes those locations to the Robot Task FIFO 655 via data lines 697. As mentioned above, the Vision Control task is additionally responsible for initiating an early conveyor index if no needles were imaged in a camera field of view.

As described briefly above, the Vision Control task runs each time either conveyor 102, 104 completes indexing. It is initiated to begin needle recognition upon receipt of either a CONVEYOR 1 SETTLED signal 631 or CONVEYOR 2 SETTLED signal 632 which is generated by the PLC 620 and routed through the Conveyor Control task 680 each time respective translucent indexing conveyor 102, 104 has ceased indexing. Each CONVEYOR SETTLED signal 631, 632 goes high (logic "1") approximately two (2) seconds after the PLC has been requested by the Adept® robot to index a translucent indexing conveyor. Each of the CONVEYOR SETTLED signals 1 and 2 (631,632) remain high until the PLC 620 receives the next respective INDEX CONVEYOR 1 or 2 signal 698,699 from the Robot Control and Conveyor Control tasks.

The Vision Task 660 activates that camera which is associated with the conveyor settled signal. When activated, the camera 105,105a takes a picture of the backlit areas 101,103 of the conveyor belt 102, 104. Any image obtained is preferably converted to binary image data for subsequent digital processing. The Vision Control task 660 utilizes "vision tools" to detect acceptable needles, and places the coordinates of acceptable needle pick-up points in the FIFO buffer 655 for the Robot task. An "acceptable" needle in the backlit areas is a needle that measures within the tolerances of the needle parameters that have been previously accepted during the needle changeover procedure. The needle changeover procedure is a procedure to inform the infeed system software of the type and size of the needles in the current batch to be processed and must be executed before making needle batch changes as to be discussed below. Specified needle tolerances are for the needle radius, barrel width, angular characteristics of the needle with respect to the robots, and the calculated area as computed from the needle parameters.

Auto-Imaging Algorithm

As mentioned above, if a detected needle is unrecognizable, the auto-imaging algorithm is invoked to change the camera vision parameters. Thus, after the binary image data is processed, a determination is made as to whether the needle image is of the specified radius, whether the needle image is of the specified barrel width, whether the needle image has the specified angular characteristics, and, whether the needle image area is within the specified tolerance. If any of these criteria are out of specification, then an auto-imaging algorithm is executed which functions to take a series of pictures of the same needle image at the respective camera's field of view to thereby enhance the needle image for better needle recognition by improving the vision parameters between pictures. Thus, after each of the series of pictures is taken, the auto-imaging algorithm will automatically adjust the camera's iris and vision system lighting parameters to enable the vision system to image the needles properly within the camera's field of view. For example, when adjusting the lighting of the fields of view, certain camera vision parameters such as the gain, offset, and binary threshold may be modified. The auto-imaging algorithm is executed until a needle is recognized in each camera's field of view and is not repeated until a needle changeover is executed.

Even when the cameras 105,105a controlled by the Vision Control task 660 are adjusted, needle images may still not be imaged properly. This is because each camera's field of view utilizes a backlighting source and needles that overlap, touch with each other, or, are clipped by field of view edge boundaries will not be considered for recognition. Thus, the Vision Control task will make a determination of whether the needles overlap or touch each other, and, will determine whether the needles are too close to the edge of the field of view.

After all of the possible needles are recognized, the Vision Control task will calculate the needle pick-up coordinates of the acceptable needles and place them in the Robot Control task FIFO buffer 656 to enable the robot to pick and place the acceptable needle onto the precision conveyor. In the preferred embodiment, the maximum number of needles that can be recognized during each dwell cycle of each translucent indexing conveyor is three (3). If less than one or if no needles are recognized, a robot may be signaled to index the corresponding conveyor early, causing the vision system to abort its processing as described above.

Vision Control Task 660 is responsible for limiting the number of needle locations written to the FIFO to three, since the Robot Control Task will pick and place a needle for every needle location passed to the FIFO 655. In the preferred embodiment, the Vision Task is limited to operate for five seconds per indexing conveyor cycle.

The Vision Control Task 660 performs error recovery on three types of errors. These errors are grouped as imaging errors, processing errors, and gross errors. The gross errors cause the Task Manager error recovery to respond and stops the Vision Control Task 686 immediately. When an imaging error occurs, the Vision Control Task 660 suspends all execution on the current FOV and requests an early index of the conveyor belt by generating either INDEX CONVEYOR 1 EARLY or INDEX CONVEYOR 2 EARLY signals 631, 632 as discussed above. Receipt of these signals causes no needles to be placed in the parts FIFO and forces both vision/robot systems to pass on the current FOV of needles. If a processing error occurs, the Vision Control Task suspends all processing on the current needle and begins processing a new needle in the same FOV if another needle is available. As a result, the Vision Task does not insert the needle into the parts FIFO.

Conveyor Initiation Task

The Conveyor Initiation Task 690 functions to initiate the Conveyor Indexing Control Task 680 and is started whenever the ROBOT ENABLE signal 619 is raised from the PLC 620. Once started, this task requests an INDEX INFEED CONVEYOR 1 (102, 104), signal 637, then waits approximately two (2) seconds, and requests an INDEX INFEED CONVEYOR 2 (102, 104), signal 639, as shown in FIG. 8. The task 690 is then terminated and is not restarted again until the ROBOT ENABLE signal 619 is lowered and raised again.

Task Manager

The Task Manager 640 initializes the software and hardware I/O signals, the global variables, and the vision/robot system tasks. Once the vision/robot system tasks are running, the task manager monitors the integrity and status of each task currently running and the resources that are controlled by these tasks. The status poll signals 647a–647f are indicated in FIG. 8. The resources are the robot, communication ports, and the I/O signal lines. The Task Manager reports any errors to the PLC, via the SYSTEM FAIL signal 622, and the SCADA node, via the SCADA Node Interface Task 695. The SYSTEM FAIL signal 622 is generated whenever a robot (as detected by the Task Manager) has recognized a gross error which prevents it from continuing operation. This signal is active-low and remains low until the Adept robot is reset. Thus, the PLC must lower the ROBOT ENABLE signal 619 immediately upon receiving this signal.

For gross errors occurring with the vision/robot control software, the Task Manager 640 is utilized to detect and recover from these errors by continuously polling the status and integrity of all steady-state tasks and resources during program execution. If it is determined that a gross error has occurred, the SYSTEM FAIL signal 622 will be raised to the PLC 620 and all tasks except the SCADA Node Interface Task, the Control Panel Task and the Task Manager will be stopped. A code indicating the reason for the last unrecoverable error will be available to the SCADA Node through the SCADA Node Interface Task. In some cases, an error message will be displayed in the Monitor Window of the Adept robot controller. After the SYSTEM FAIL signal is raised, the Task Manager will attempt to correct any problems detected on the robot and notify the operator through the Monitor Window. In most cases, the operator will only need to raise the ROBOT ENABLE signal again to re-set the vision/robot control software.

Control Panel Task

The Control Panel Task 662 presents a mouse controlled panel that allows an operator to access various software "debugging" utilities, to access diagnostics utilities, to control the speed of the robot, and to select new positions that the robot will move to for picking and placing needles. Also, the Control Panel Task allows the operator to stop the vision/robot system tasks from executing.

SCADA Node Interface Task

The SCADA Node Interface task 695 polls the SCADA Node RS-232 interface for messages from the SCADA node and control computer 46. The task will act as slave to SCADA Node requests for Adept and camera set-up procedures necessitated by product changeovers. These requests are valid only when the ROBOT ENABLE signal 619 is deactivated.

Lens Control Task

The Lens Control Task 670 is initiated only when the SCADA node requests a new product to be introduced to the vision system and is executed only as an off-line process. The Lens Control Task 670 accepts the new needle parameters and adjusts the field-of-view size for both cameras to accommodate the new product size. The zoom, focus, and iris lenses are affected by this new product introduction, as well as internal vision system parameters, such as gain, binary threshold, and offset, used for imaging. Once the cameras are adjusted, the task is suspended until another new product is introduced to the vision/robot system.

Product Changeover

Prior to enabling the robots to begin the needle infeed process, a Needle Changeover procedure is invoked to inform the Vision and Robot Control tasks of the control system software of the type and size of the needles to be processed. This needle changeover procedure must be completed before making needle batch changes. If a changeover is not completed before the first needle batch run after power-up, an error message will be displayed at the FIX/DMACS (SCADA Node) screen when the robots are enabled and the robots will not run. If a changeover is not completed between different needle batch runs, the vision tasks will not identify any needle being run.

Essentially, an operator of the system enters the needle parameters in appropriate units, e.g., millimeters and degrees at the FIX/DMACS screen (not shown) of the SCADA task 695 through data lines 635. Such needle parameters for use by the Vision tasks include, the needle radius and the radius tolerance, acceptable needle angles and their tolerances, and, the needle width and the width tolerance.

In addition to inputting needle change parameters for the vision tasks, initial camera set-up parameters associated with the particular batch of needles to be processed are also input through the SCADA Node for use by the system. The software utilizes the information provided by the user via the SCADA Node to automatically adjust the lens for the correct field-of-view size, focus, and zoom parameters prior to enabling the robots.

Precise Positioning

For automatic swaging to take place at the swaging station 200 it is necessary that the needle be precisely oriented within the universal gripper of the rotary swage dial. Thus, the transfer of the needle 39 from the engagement jaws 77,79 of the boat 70 to the universal gripper (indicated as step 26 in FIG. 3 and explained in detail below) necessarily requires that each needle 39 be in a precisely oriented position. Efficient usage of the robotic arms and the algorithm described with respect to FIG. 8 provides that the robotic assembly 108 may load a needle by its barrel in a conveyor boat in one of two possible orientations. Then, to ensure that each needle is uniformly oriented for transference to the universal gripper, a needle orientation device ("plow") 111 is provided as shown in FIGS. 5 and 10 to orient each needle while engaged between jaws 77,79 on conveyor boat 70 to a single needle orientation. The plow comprises an elongated arcuate blade 80 protruding from a mounting bracket 81 as best shown in FIG. 10. In the preferred embodiment shown in FIG. 5, the plow is mounted at a fixed location along the precision conveyor 106 to enable arcuate blade 80 to scoop needle 39 positioned on the conveyor boat 70 while in forward motion. After contact is made, the arcuate portion of the needle 39 is lifted and rolls over the arcuate blade 80 of the plow 111. Provision of the plow 111 ensures that each needle conveyed to the suture swaging station is oriented in the same direction.

Another mechanism is provided for further orienting the needle upon the precision conveyor boat is the needle pre-positioning assembly 95 illustrated in FIGS. 10 and 10(*a*). The pre-positioning assembly 95 comprises a pulley 99 driven by an extended drive shaft from Camco drive motor 62 and timing belt 97 for rotating a cam 98 as shown in FIG. 10(*a*). Cam follower 91 is provided for rotating the pre=positioning assembly about shaft 96, thereby actuating arm stop 93 to reciprocate from a first position above the engagement jaws 77,79 of conveyor boat 70, to a position that enables blade 94 of arm stop 93 to bear upon the barrel end 44 of needle 39 while the precision conveyor boat 70 is conveyed in the forward direction as indicated by the arrow in FIG. 10. Impeding the forward motion of the needle 39 by blade 94 forces the needle to move within engagement jaws 77,79 of the conveyor boat 70 so that the engagement jaws 77,79 engage the needle at a precise location on its barrel portion. Note that the cam 98, as driven by timing belt 97, is designed so that the arm stop 93 reciprocates in a timed relation with the forward motion of the conveyor boat 70 so that each needle upon each boat 70 is further oriented. After the needle is oriented, the arm stop 93 is reciprocated to its position above the conveyor boat 70 to await the next needle for further orientation.

After the precision conveyor boat 70 is equipped with a needle 39 oriented in the proper direction in the manner described above, it is conveyed to the precision transfer assembly for subsequent transfer to the automatic swaging station 200.

Precise positioning and the Moveable Hard Stop Assembly

Figure 10A:
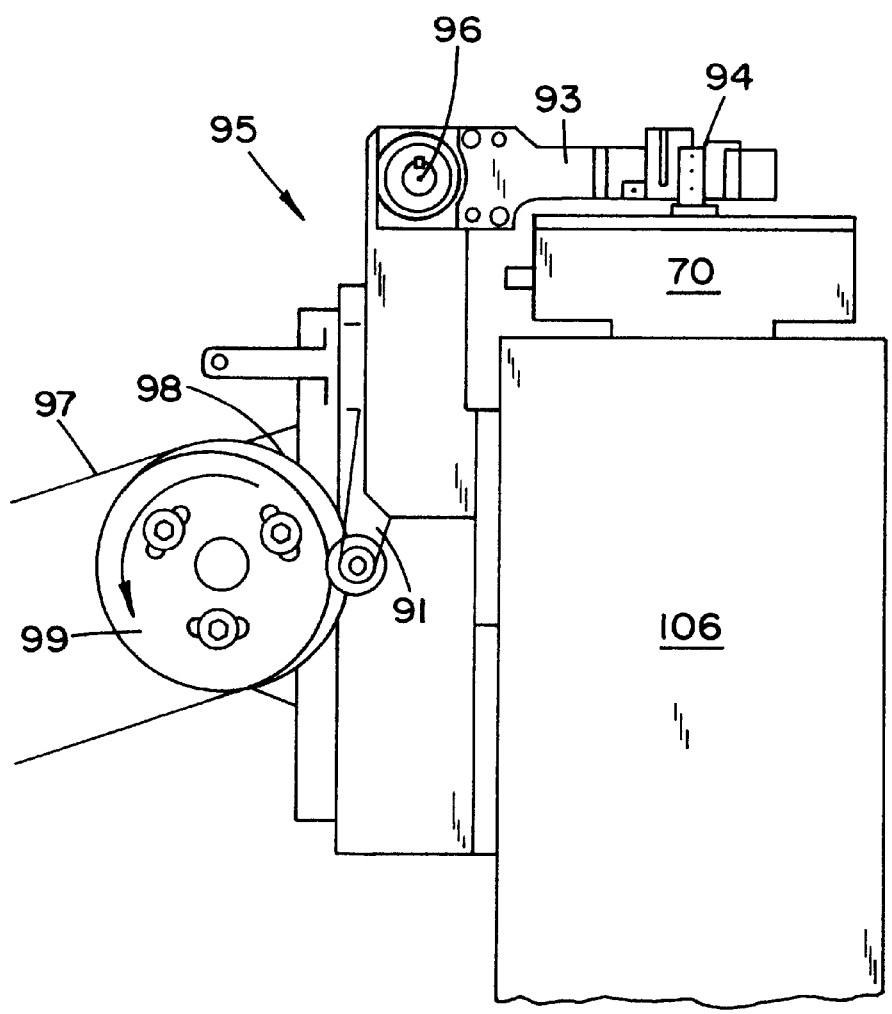
FIG. 10(a) is a diagrammatic elevation view of the pre-positioning stop and the precision conveyor of the present invention.
Figure 11A:
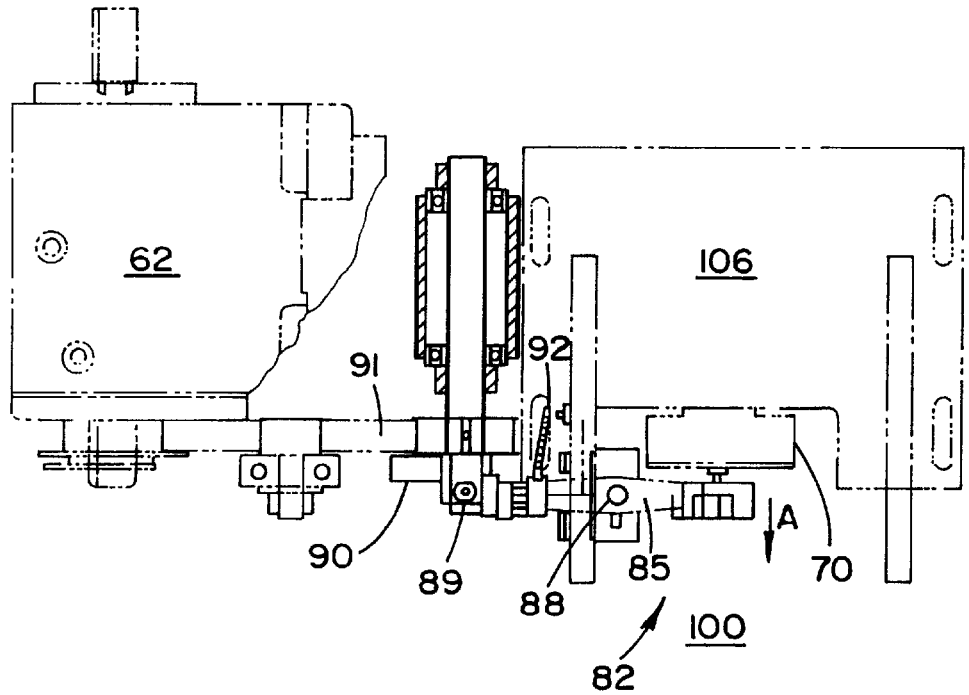
FIG. 11(a) is a partially cross-sectioned plan view of the precision hand off station of the present invention.
Figure 11B:
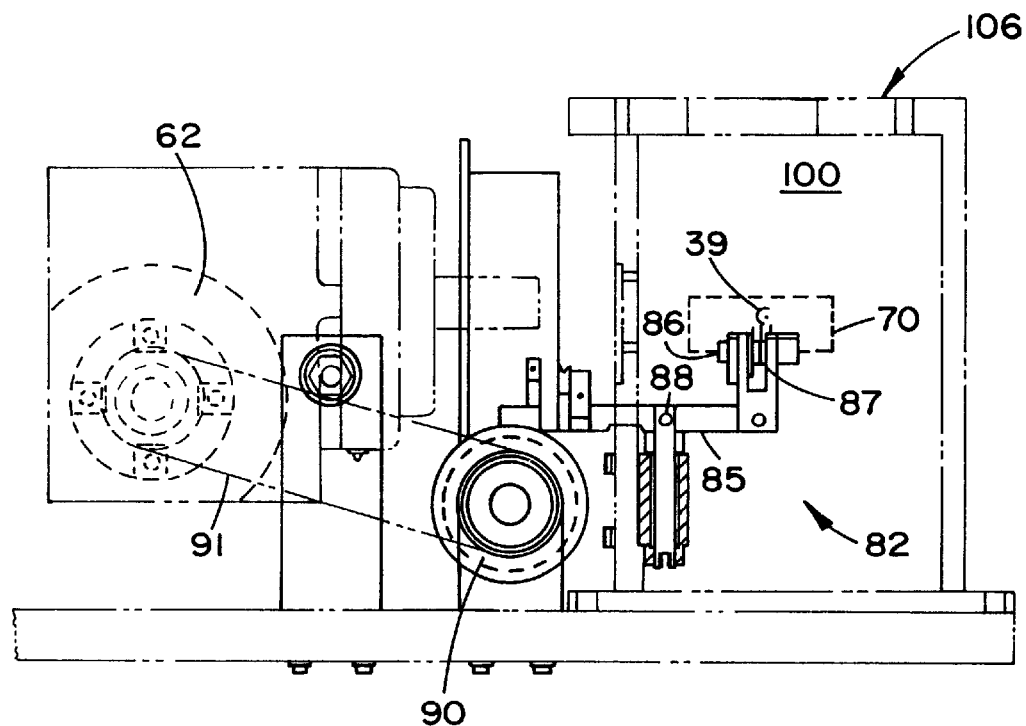
FIG. 11(b) is a partially cross-sectioned elevation view of the precision hand off station illustrated in FIG. 11(a).

After the needle 39 has been plow oriented in the conveyor boat 70 and pre-positioned as previously described with respect to FIGS. 10 and 10*a*, it is conveyed to a precision positioning station for precise placement before hand-off to the automatic swaging system 200. The precise positioning station and a moveable hard stop assembly 82 is illustrated in FIGS. 11(*a*) and 11(*b*) where FIG. 11(*a*) is a top or plan view of the apparatus and FIG. 11(*b*) is an elevation end view of the apparatus. The hard stop assembly 82 illustrated in FIGS. 11*a* and 11*b* is the mechanism used for executing a hard stop of the needle conveyed in conveyor boat 70 when the boat has reached the end of its destination at the hand-off point for the needle swaging station. The hard stop 84 (illustrated in FIGS. 12(*a*) and 12(*b*) provides a precise positioning surface for the needle in boat 70. Typically, the hard stop 84 provides positioning within an accuracy of 0.001 inches of a denoted reference position subsequently used for swaging. The hard stop of the present invention differs from the knife blade stop described with respect to the parent application inasmuch as the knife blade stop in the parent application was a fixed stop mechanism whereas the apparatus illustrated in FIGS. 11*a* and 11*b* is a moveable stop mechanism. The moveable stop assembly 82 is reciprocated out of the way to provide clearance for the conveyor boat 70 as it continues its downward travel to return to the opposite end of the conveyor.

Figure 12A:
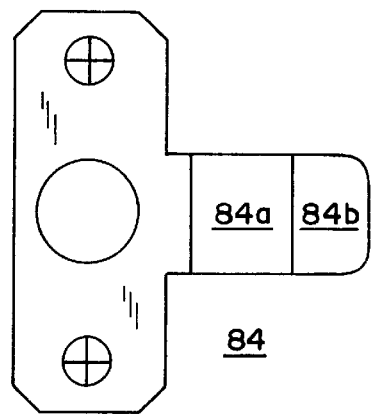
FIG. 12(a) is a plan view of the moveable hard stop used in the precision hand off station of the present invention.
Figure 12C:
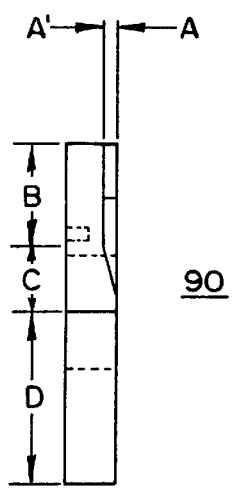
FIG. 12(c) is a side profile of a face cam used in the moveable hard stop assembly.
Figure 12B:
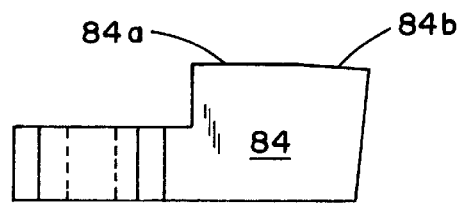
FIG. 12(b) is a side or elevation view of the moveable hard stop illustrated in FIG. 12(a).

As the conveyor boat 70 reaches its final position as illustrated in FIG. 11(*a*) the moveable hard stop 84 is reciprocated inwardly towards the precision conveyor to receive the butt end of the needle 44 on needle face 84*a* as illustrated in FIG. 12(*a*), (*b*). As the boat 70 arrives at its final location, the gripping jaws 146,148 (illustrated in FIGS. 21(*a*)–(*c*)) of the swage device arrive on the opposite side of the needle hard stop 84. The needle is thus restrained during handoff against downward movement by the needle face 84*a* of hard stop 84, from side-to-side movement by the jaws 77, 79 of the conveyor boat 70 against rearward motion by the conveyor boat 70 and against forward motion by the face of universal gripper on the swage machine which is to receive the needle. The universal gripper also has a pair of jaws 146,148 which engage the needle to prevent side-to-side motion after transfer is complete. After the jaws 77, 79 are opened and the jaws 146,148 of the universal gripper are closed, the hard stop 84 is reciprocated in the direction of the arrow A in FIG. 11*a* to provide clearance for movement of jaws 77,79 on boat 70 and for movement of the butt end of the needle as it is moved out of position by the universal gripper. To provide further clearance for the butt end of the needle, and to avoid dislodging it from its precise position, the trailing face of the hard stop 84 is tapered as illustrated at 84*b* in FIG. 12(*b*).

The hard stop 84 is spring mounted in a pivot arm 85 by means of a pivot pin 86 and a coil spring 87 which maintains the position of the stop, but provides breakaway capability for the stop in the event of misalignment of the precision conveyor. The breakaway prevents any damage to the conveyor boat 70 from the hard stop 84 in the event of any malfunction of the device. The pivot arm 85 is pivoted about pivot point 88 by means of a guide roller 89 and a face cam 90 which is rotated by an extended drive shaft from the Camco drive motor 62 through belt drive assembly 91.

The face cam 90 is illustrated in FIG. 12(c) and provides for reciprocal movement of the hard stop mechanism of approximately ⅛ of an inch during each dwell period. The cam surface is illustrated with A–A' being the reciprocal distance, dwell period B, being the retracted dwell period, dwell period D being the engaged dwell period, and C being one of the transition periods. The pivot arm 85 is pulled into engagement with the face cam by means of a tension spring 92. As the face cam 90 is rotated, the hard stop is held in its engagement position for approximately 195° of rotation of the face cam and held in its retracted position for approximately 120° of travel with transition periods therebetween. The ratios of belt drive 91 are chosen to provide one cycle of rotation for the face cam 90 for each step advance of the conveyor boat 70.

Suture Drawing and Cutting

Simultaneously with the positioning and transfer of the surgical needles to the universal gripper on the swage dial, predetermined lengths of suture are being drawn, tipped and cut by the suture drawing and cutting station 300, as indicated in steps 18–24 of FIG. 3(a) and (b).

Figure 15:
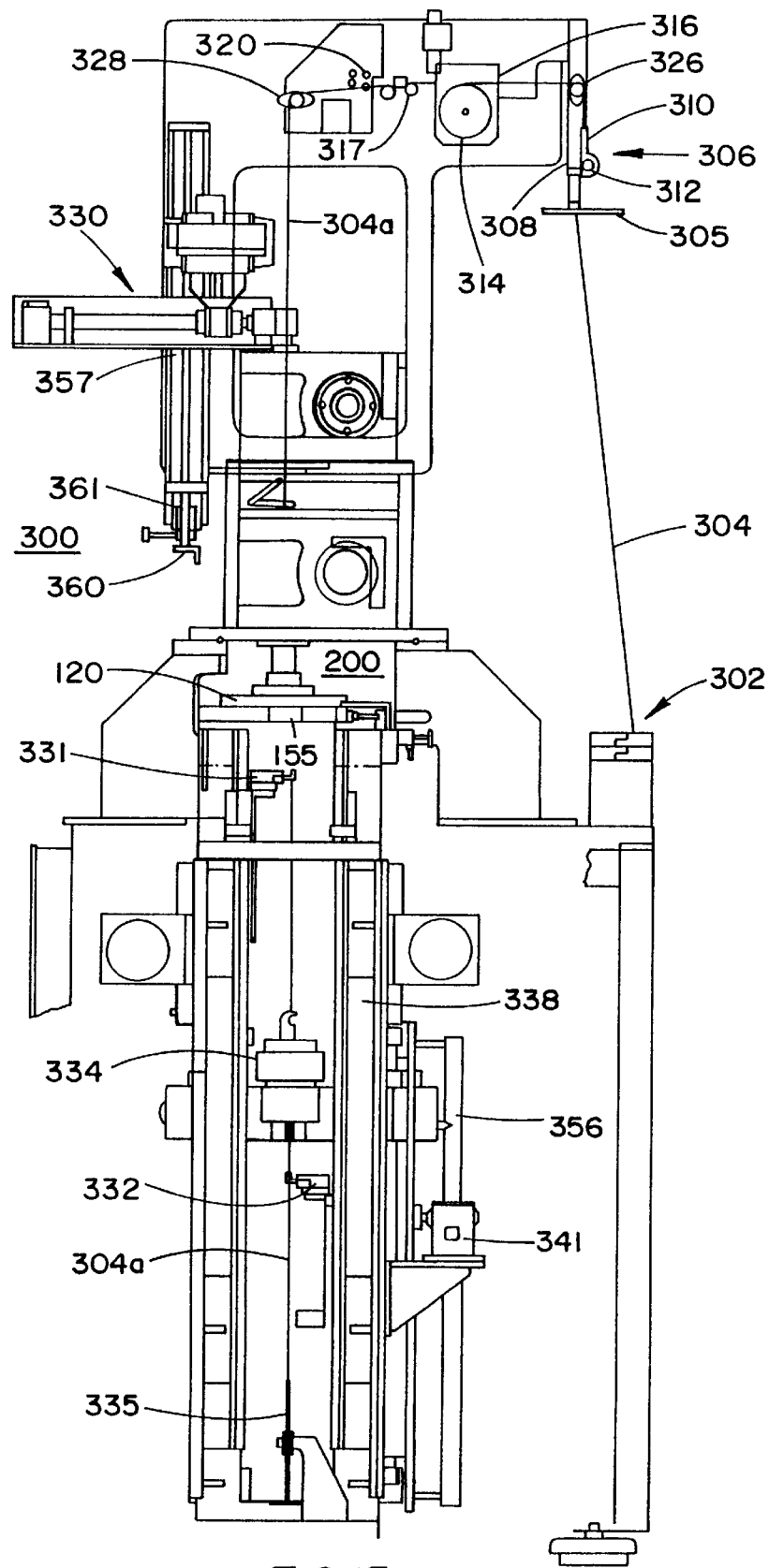
FIG. 15 is front elevation view of the suture drawing and cutting tower assembly used in the present invention.

FIG. 15 illustrates a front elevational view of one designed embodiment of a servo tower 300, similar to that shown in FIGS. 2–6, and shows the suture path therethrough. Suture 304 is pulled off one end of a supply roll 302 mounted to one side of the servo tower, through the center of an annular guide disc 305, and into a mechanical tensioner 306. The mechanical tensioner can comprise a stationary guide frame 308 and a pivotally mounted guide frame 310, pivotally mounted about a pin 312 at the lower end of the stationary guide frame. Each of the stationary guide frame and the pivotally mounted guide frame has a series of spaced guide elements, each with a central guide aperture therein, which are alternately interleaved, such that the spaced guide elements of the pivotally mounted guide frame alternate with the spaced guide elements of the stationary guide frame. The pivotally mounted guide frame 310 is spring biased about the mounting pin 312 to rotate the top thereof away from the top of the stationary guide frame, such that the suture extending between the alternating stationary guide frame elements and the pivoted guide frame elements is placed under tension while being pulled therethrough.

The suture then travels over idler roller 326, and extends to and is wrapped twice around a tension roller 314 which is mounted on one end of a torque motor 316, (illustrated in dotted lines in FIG. 15) which applies a given tension to the suture as it is pulled through the servo tower by the first and second gripper assemblies 331, 332. The gripping assemblies alternate in a hand over hand advancement as previously described in U.S. Ser. No. 08/181,595, entitled "Suture Cutting System," the disclosure of which is incorporated herein by reference thereto. Each different suture size and material should have a different tension applied thereto as it is drawn through the apparatus. The torque motor 316 provides a different tension force for each different suture size and type, and the specific tension force (in grams per volt to be applied by the torque motor) is downloaded from a computer program at each suture batch changeover. The proper tension is important for several operations described herein, and is particularly important for the cutter assembly to operate while providing a clean neat cut without a broom effect.

The suture then extends to an out-of-suture sensor positioned at 317, and then through a knot detector 320. The suture 304 then travels to a second idler roller 328 to change direction again, from which the suture 304 extends vertically downwardly through a heated tipping assembly 330, which heats and ultimately stiffens a small length of the suture, at which small length the suture is subsequently cut and the cut tip is inserted into and swaged to a needle.

The suture 304 then extends downwardly from the tipping assembly to a large idler roller 335 mounted near the bottom of the machine having an appropriately 7 inch diameter, at which the suture reverses direction and travels vertically upwardly to the first and second gripper assemblies 331, 332, to the suture cutter assembly 334 and a suture swaging During the insertion operation, the cut suture end is guided by a funnel shaped aperture 270(a),271(a) in a suture guides 270,271 into the aperture in the end of a needle, after which a moving anvil 273 is moved relative to a stationary anvil 274, of a swage die, to swage and attach the needle to the suture.

In this embodiment, after initialization, one gripper assembly will be in a home position, 2" below the face of the swage die mounting surface, allowing a 2.03" movement from the home position to an insert position. A proximity switch is located on each tower at 2" below the face of the swage die mounting surface to set the home position during an initialization procedure.

Assuming that the machine is being initially set up to cut a desired length of suture, the cutter assembly 334 will be moved to a predetermined vertical position in the swaging machine by operation of the handcrank attached to gearbox 341. This is done by aligning a pointer for the cutter assembly with a vertical scale 356 positioned on the side of the swaging machine, similar to the vertical scale 357 shown above for the tipping assembly.

The cutter assembly includes a proximity switch thereon, and during an initialization procedure, the position of a gripper assembly is detected by the proximity switch, and that position is set in memory to set the servo gripper bottom position 332 during subsequent normal operation of the machine. The tipping assembly is also moved to an appropriate position in the machine as described hereinbelow.

FIG. 9 shows the right gripper 332 positioned slightly below the cutter assembly 334 so that the indefinite length strand will be gripped when the definite length swaged strand is cut. Thus, the upper left gripper 331 now grips the suture material 304 having a tipped end 358 and it now becomes the lead gripper. The next cycle begins with the lower gripper 332 vertically drawing the material 304 along the height of the drawing tower 300 for the long stroke to position the next strand to be cut for insertion within the surgical needle.

During this operation, assume that the upper gripper assembly 331 has just moved to its home position. At the home position, the gripper assembly 331 stops and waits a predetermined time, during which a needle is preclamped in an insertion position in the swaging station 200, and then moves to the insert position. The following operations are then performed substantially simultaneously. The bottom gripper assembly 332 closes, a tipping operation is performed simultaneously at the tipping assembly 330, and the swage station is simultaneously actuated to swage the needle end around the suture, attaching it thereto. Thereafter, the cutting assembly 334 is activated, cutting in the tipped area to cut the suture to the given length. Thereafter, the upper gripper assembly 331 opens, and the assembly 331 returns to the bottom position, and simultaneously therewith the lower gripper assembly 332 moves up to the home position, and the cycle is then repeated.

After removal of the swaged needle and attached suture length from the apparatus, it is subjected to a sterilization operation, during which the suture length incurs some shrinkage. Accordingly, the cut lengths of suture must be cut to lengths slightly longer than their desired(or label) final lengths to compensate for such shrinkage.

The following table gives, for silk suture, in the left column the commercial(or label) suture length, in the middle column the low servo position of the low gripper assembly below the face of the swage die mounting surface, and in the right column the cut length of suture prior to shrinkage. VICRYL shrinkage during sterilization is approximately 3% of the table values for silk.

| 18" | servo - 16.51 | allowed for 18.350" |
|-----|---------------|---------------------|
| 27" | servo - 25.51 | allowed for 27.380" |
| 30" | servo - 28.51 | allowed for 30.380" |
| 36" | servo - 34.51 | allowed for 36.380" |

As described above, after heating of a predetermined length of suture at the tipping assembly, the suture must cool to allow setting and hardening of the suture material prior to cutting of the suture at the hardened length and insertion of the cut stiffened end into a needle. This cooling of the suture is provided in this embodiment by allowing a discrete number of machine cutting cycles to occur between tipping of the suture and cutting of the suture. This is provided by allowing a predetermined long length of suture travel between the tipping assembly and the cutter assembly. Hence, the suture tipping assembly 330 is positioned near the top of the servo tower, and after heating thereat, the suture travels to the bottom of the machine, around the large idler roller 335, and then back upwardly to the cutter assembly 334. The large diameter of the idler roller 335, relative to the other idler rollers 326, 328, is provided because the small length of suture which has been heated at the tipping assembly 330, has begun to harden and set by the time the heated section reaches the large idler roller. The large diameter thereof facilitates the suture to travel therearound without picking up a permanent curved set from the large idler roller, as it is desirable for the suture to be straight, without any curve, when it is subsequently cut and inserted into a needle. The idler rollers 326 and 328 typically have a 0.5 inch diameter, whereas the large diameter roller 335 has a diameter preferably greater than 6.0 inches, approximately 7.0 inches in one embodiment.

The operation of the machine depends upon a discrete whole number of machine cutting operations to be performed between the tipping and cutting operations. Accordingly, for each different length of cut suture, the tipping assembly 330 must be positioned at a different predetermined position within the machine for the tipped section of suture to be precisely and correctly positioned at the cutter assembly 334 after a given number of machine cycles.

The following table gives in its columns, proceeding from left to right, the label suture length, the actual cut suture length, the number of machine cycles or increments provided between tipping and cutting, the total travel length of the suture between tipping and cutting, the tipping assembly vertical position above the table top, and the tipping assembly scale pointer position above the table top (explained in greater detail hereinbelow).

| SUTURE LENGTH | | | | ABOVE TABLE TOP | |
|---|---|---|---|---|---|
| LABEL | ACTUAL | INCREMENTS | TOTAL | TIPPER C | POINTER |
| 18 IN. | 19 IN. | 6 | 114 IN. | 27.64 IN. | 25.89 IN. |
| 27 IN. | 29 IN. | 4 | 112 IN. | 25.64 IN. | 23.89 IN. |
| 30 IN. | 31 IN. | 4 | 124 IN. | 37.64 IN. | 35.89 IN. |
| 36 IN. | 36.25 IN. | 3 | 108.75 IN. | 22.39 IN. | 20.64 IN. |

Figure 16A:
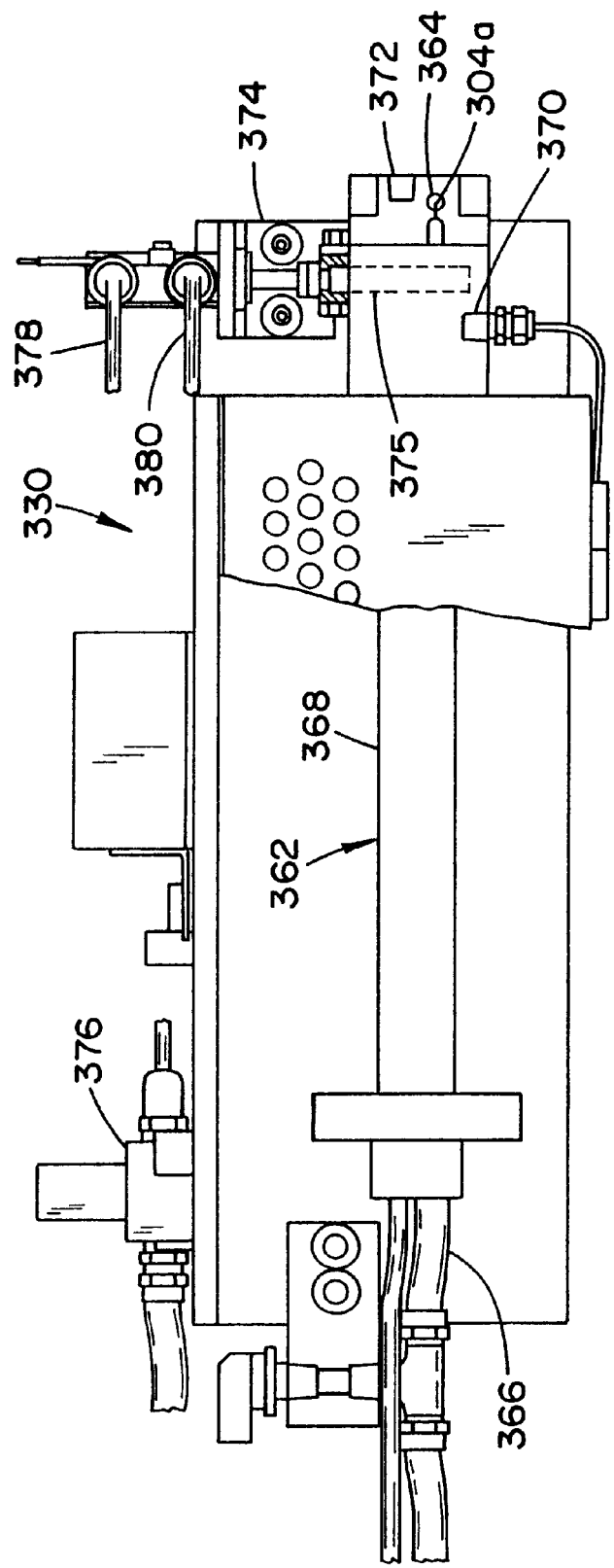
FIG. 16(a) is top plan view of the suture tipping assembly used in the suture drawing and cutting apparatus of the present invention illustrated in FIG. 15.
Figure 16B:
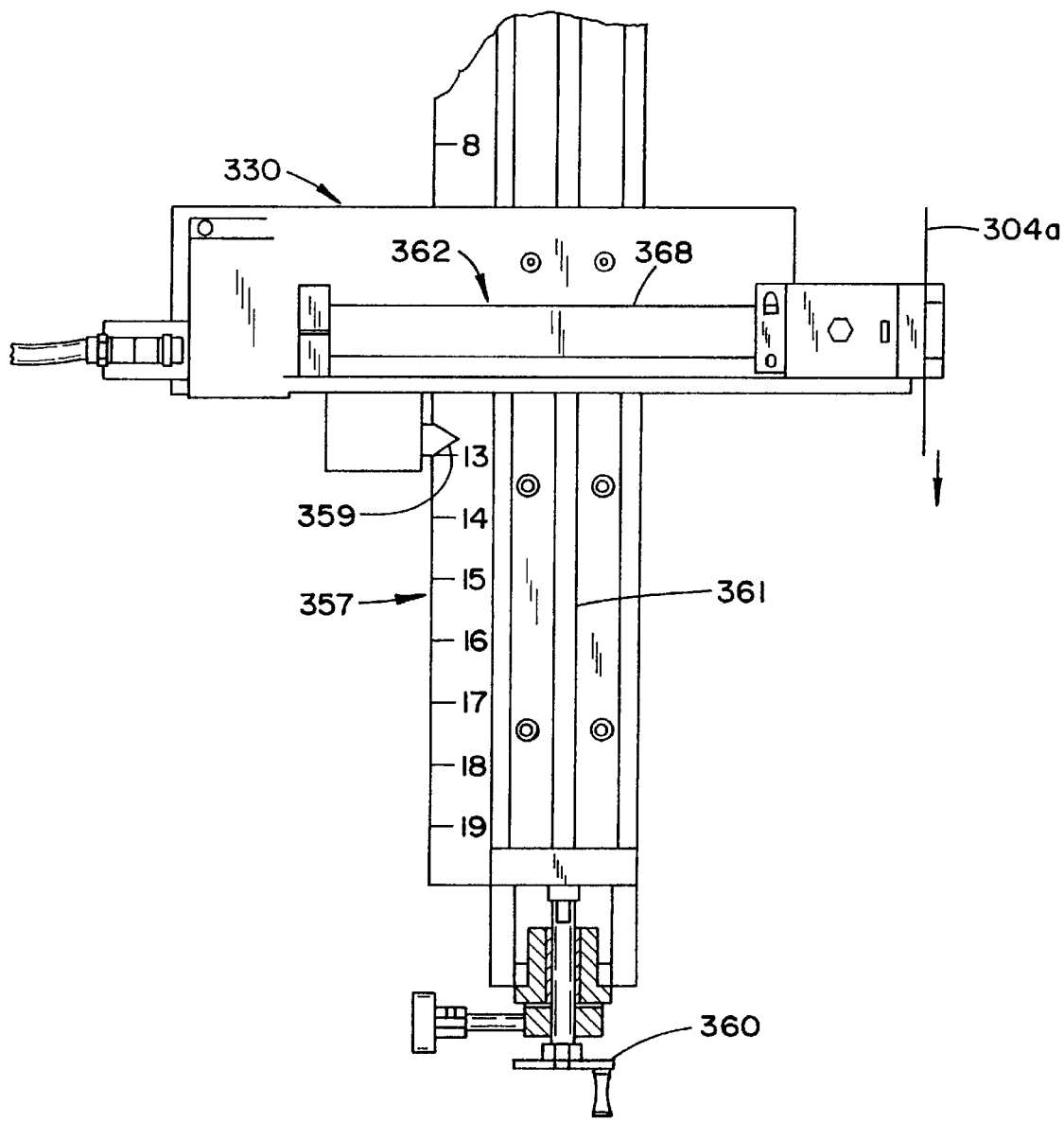
FIG. 16(b) is front elevation view of the a suture tipping assembly illustrated in FIG. 16(a) and used in the suture drawing and cutting apparatus of the present invention.

FIG. 16(b) illustrates an enlarged front elevational view of the suture tipping assembly at which a small length of the suture is heated to stiffen the suture material after subsequent cooling thereof, in preparation for cutting a given length of the suture and inserting the lead cut end of the suture into the end of a needle for swaging thereto. FIG. 16(b) illustrates the movement of the tipping assembly 330 along a vertical scale 357 provided adjacent to the tipping assembly 330. The vertical position of the tipping assembly in the machine is adjustable by a handcrank 360 and precision lead screw 361, similar to the positioning mechanism for the cutter assembly as described hereinabove. As the handcrank is rotated, the vertical position of the tipping assembly 330 in the machine is changed, and is precisely positioned by reading a pointer 359 attached to the tipping assembly on the scale 357. A chart is provided for the machine which gives, for each desired length of suture, the appropriate position for pointer 359 of the tipper assembly 330 on the vertical scale 357, and a similar position for the cutter mechanism 334 on the vertical scale 356.

In this embodiment, the position of the cutting mechanism along the drawing axis is continuously adjustable to provide an infinite number of possible different lengths of cut suture. For each different cutting position of the cutting mechanism, the tipping mechanism is adjustably positioned at a different predetermined position in the apparatus to provide for the tipped section of suture to be precisely positioned at the cutter mechanism for a discrete number of machine cycles.

In an alternative embodiment which does not have this infinite adjustment feature, several standard lengths of suture are accommodated by several standard positions which are fixed in the machine by pins which secure the cutter mechanism to the machine frame by pin receiving holes in the machine at the standard positions. For example, the cutter mechanism might be moved to a position for cutting 18" sutures and be secured to the frame by the placement pins being inserted into the pin receiving holes in the machine for 18" sutures. The cutter mechanism might also be moved to positions for cutting 27", 30", or 36" sutures by moving the placement pins to the pin receiving holes in the machine provided for those length sutures. Each different position can have a separate proximity switch provided therefor, which indicates the cutting mechanism position to the controller, which then downloads the appropriate servo gripper bottom position. The appropriate tipping mechanism position is known for each different cutter mechanism position.

FIGS. 9(a) and 9(b) illustrate a heater 362 in the tipping assembly 330 and the vertical movement of the suture 304(a) down (front view, FIG. 16(b)) and through (top view, FIG. 16(a)) a suture tipping aperture 364, FIG. 16(a), positioned on the right side of the tipping assembly. FIG. 16(a) illustrates further details of the flow of heated air through the tipping assembly and its control to selectively heat and tip the suture. As described previously, the tipping assembly 330 is mounted near the top of the machine so that it takes a discrete number of machine cycles for the suture to reach the cut position. This gives the tipped area time to cool down before the cutting and insertion operations. The tipping assembly operates by flowing air supplied at a regulated pressure through an inlet air duct 366 at a regulated flow rate, in one embodiment 195 CFH (Cubic Feet per Hour), over a heater coil mounted within an outer heater casing 368. Air is supplied to a flowmeter at a regulated pressure required to maintain 195 CFH of air flowing over the heater coil. A thermocouple 370 is positioned in the air flow at the discharge end of the heater casing 368, to monitor and control the air temperature through a controller in a programmable logic controller (PLC). The tipping assembly 330 is operated at various temperatures between 200° F. and 550° F. depending upon the particular suture material to be run. The particular temperature is a down loaded parameter from an operating program at each suture batch changeover. The tipping assembly guides the suture and provides a 2.000" long heating aperture 364 for the tipping length.

The constant flow of heated air at the outlet of 368 flows either 1) through the heating aperture 364 in which the suture 304 is intermittently stopped and positioned during a tipping operation, or 2) alternatively the heated air is dumped into the surrounding atmosphere through a diverter channel 372, illustrated in FIG. 16(*b*). The flow of hot air is controlled by an air cylinder 374, under control of a solenoid 376, which controls the flow of actuating air through air tubes 378, 380. The air cylinder 374 controls the position of a retractable slide element having a flow aperture therein which is selectively positioned in front of either 1) a channel into the heating aperture 364 or 2) the diverter channel 372, depending upon the position of the slider element which is controlled by an air cylinder.

As an example, the following control parameters have been established for heat tipping of Braided VICRYL sutures sizes 1, 0, 2/0, 3/0 and 4/0. The suture tension refers to the tension force in grams which the tension roller 314 and torque motor 316 apply to the suture as it is being drawn through the machine by the grippers.

| Suture Size | Tipping Temp. +/−25 deg. | Tipping Time +/−25 Ms | Suture Tension +/−25 Grams |
| --- | --- | --- | --- |
| 4/0 | 375 F. | 380 | 275 |
| 3/0 | 395 F. | 380 | 275 |
| 2/0 | 410 F. | 380 | 275 |
| 0 | 425 F. | 380 | 275 |
| 1 | 435 F. | 380 | 275 |

As a further example, the following control parameters have been established for suture tension and heat tipping of silk sutures sizes 2/0, 3/0 and 4/0. In the following table the left column lists commercial needle types, the next column needle sizes, the next column suture sizes, the next column suture tension in grams applied by the tension roller 314, the next column tipping dwell time, the next column tipping heated air flow in standard cubic feet per minute, and the right column suture tipping temperature.

| SILK SUTURE AND TIPPING PARAMETERS | | | | | | |
| --- | --- | --- | --- | --- | --- | --- |
| Needle type | Wire Size (0.000") | Suture Size | Suture Tension (grams) | Tipping Dwell (seconds) | Tipping Air Flow (SCFM) | Tipping Temperature (°F.) |
| Tolerance | N/A | N/A | (±10 grams) | (±0.020) | (±5) | (±15) |
| CT-1 | 39 | 2-0 | 275 | 0.380 | 190 | 300 |
| CT-2 | 39 | 2-0 | 275 | 0.380 | 190 | 300 |
| SH | 26 | 2-0 | 275 | 0.380 | 190 | 300 |
| SH | 24 | 3-0 | 275 | 0.380 | 190 | 300 |
| SH | 22 | 4-0 | 275 | 0.380 | 190 | 300 |
| SH-1 | 22 | 3-0 | 275 | 0.380 | 190 | 300 |
| SH-1 | 18 | 4-0 | 275 | 0.380 | 190 | 300 |

The previous tables are for braided VICRYL suture and silk suture, and similar tables could be developed for other suture materials such as Ethibond® (braided polyester) and monofilament and braided nylon.

The suture drawing, tipping and cutting is more completely described in U.S. Ser. No. 08/804,478, U.S. Ser. No. 08/803,573, and U.S. Ser. No. 08/804,477, all of which are entitled "Suture Cutting System," the disclosures of which are incorporated herein by reference thereto.

The Swage Dial Drive Assembly

Figure 13A:
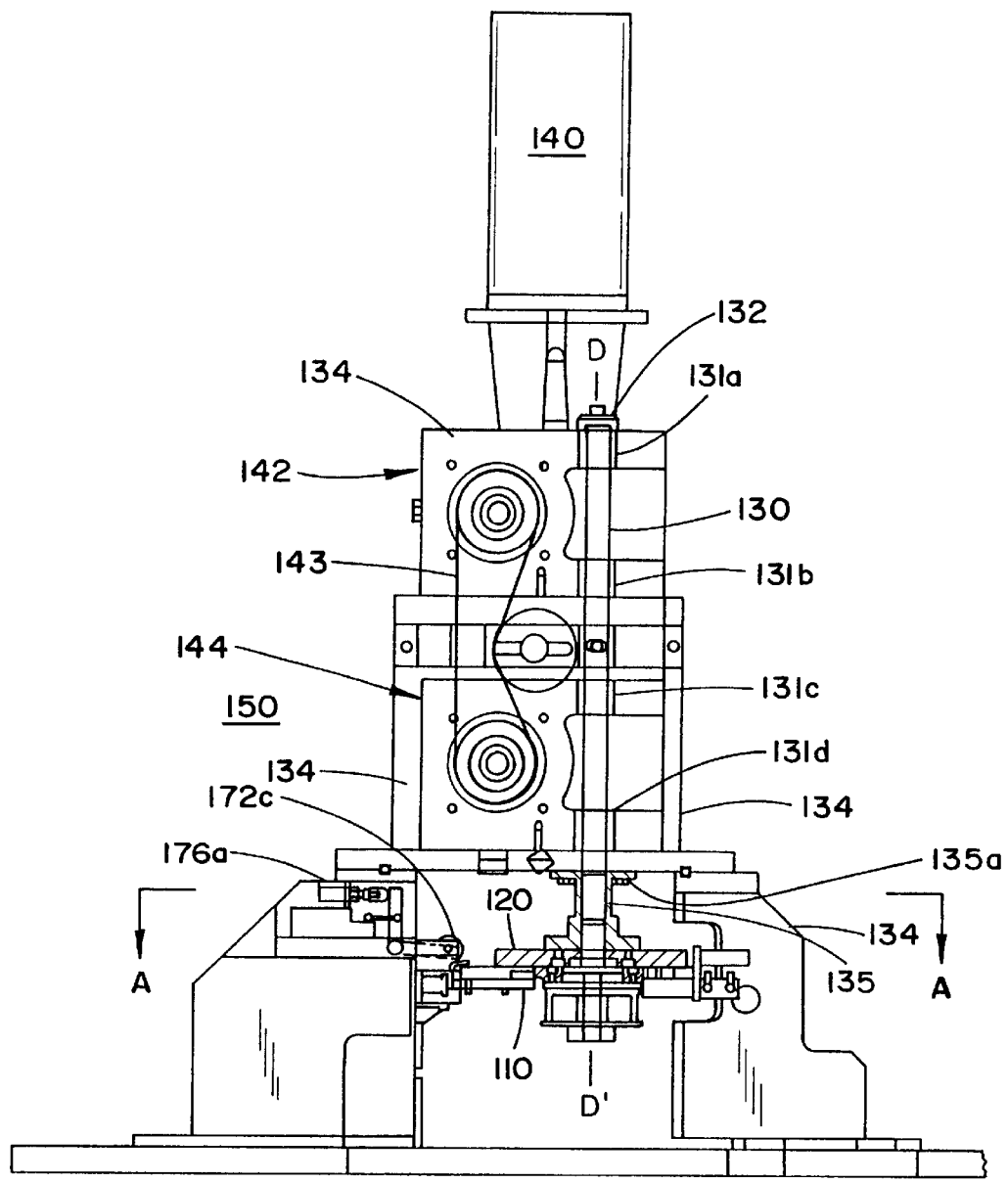
FIG. 13(a) is an elevation view of a portion the apparatus illustrating the drive for the cam dial and swage dial of the present invention.
Figure 13B:
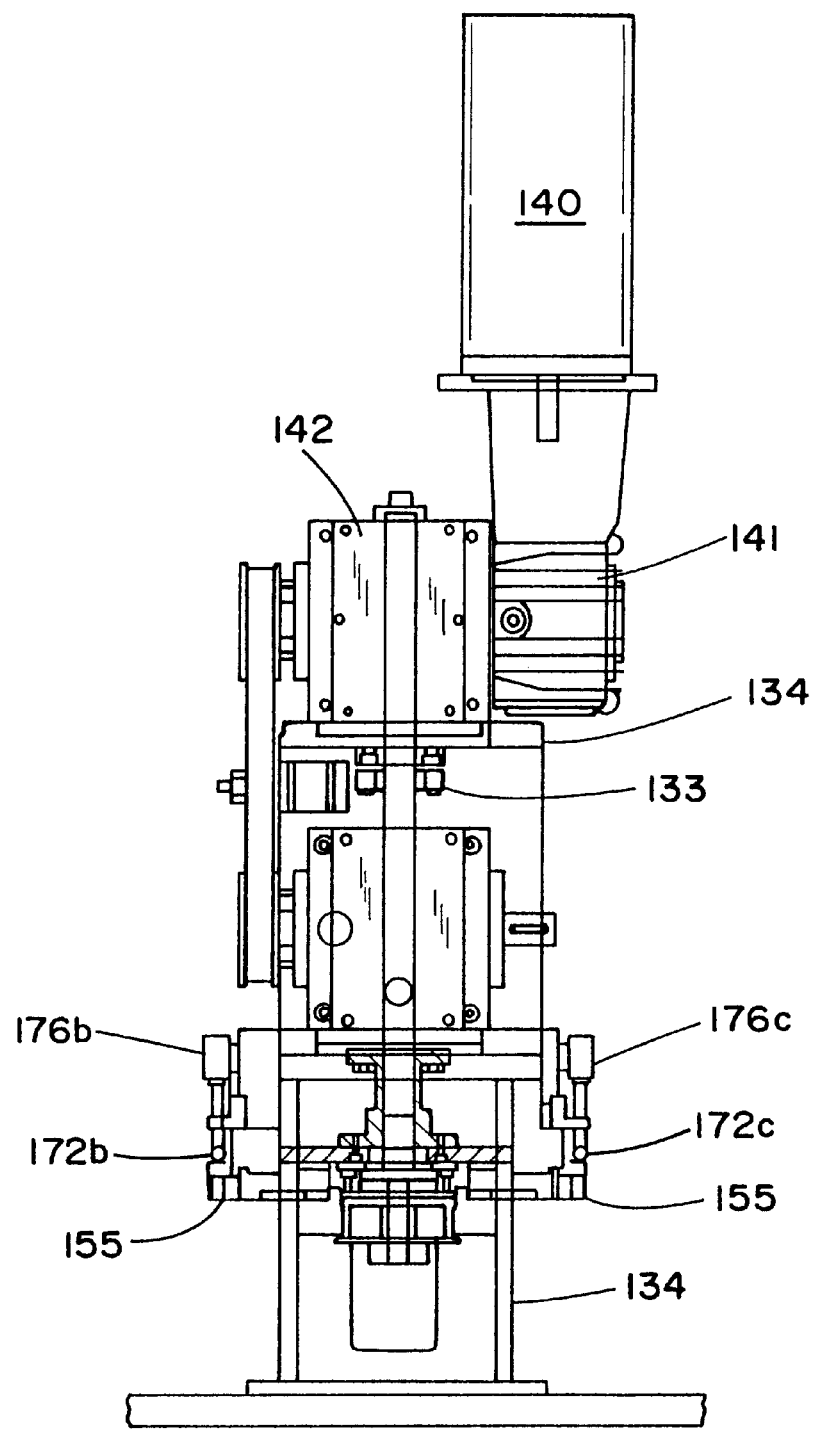
FIG. 13(b) is a side view of the drive for the swage dial illustrated in the elevation view of FIG. 13(a).

The drive assembly for the swage dial 150 is illustrated in FIGS. 13(*a*), 13(*b*) and 8. As illustrated in FIG. 13(*a*), the swage dial assembly 150 includes a swage dial 110 and a cam dial assembly 120 both of which are independently driven by the drive means of the present invention. A drive motor 140 drives both of these dials through a first indexing drive transmission 142 and a second indexing drive transmission 144 through a 90° reduction transmission 141 and are coupled together with a timing belt 143. The indexing drive assemblies 142,144 are "CAMCO" Indexer Drivers Model 350RGD 4H24-360 with a 10 to 1 reduction in transmission 141 and an oscillation motion for the cam dial assembly 120. As will be hereinafter explained with respect to FIGS. 10–11, the first indexing CAMCO drive includes 180° of drive and 180° of dwell for every revolution of the transmission drive 141 which results in a 90° drive dwell cycle for the first indexing drive 142. The first indexing drive 142 drives shaft 130 about a single drive axis D–D' illustrated in FIGS. 13(*a*) (*b*) and 14. It is journalled for rotation in bearings 131*a,b,c*, and *d* and is secured in place by drive cap 132 and a compression drive collar 133 which is connected to the output of the first indexing drive 142. A modular frame assembly 134 supports each of the drive elements about the central drive axis D–D'.

The second indexing drive 144 also includes 180° of drive, a second 60° of drive, a 30° dwell, a 60° drive and a 30° dwell for each revolution of the input drive from belt means 143, and the indexing drive 144 is phased with the drive and dwell cycles of the first drive 142. As will be hereinafter described with respect to FIGS. 10 and 11, during each dwell period of the swage dial 110, the cam dial assembly 120 is held in a dwell position and then rotated to enable radial reciprocation of the universal grippers with respect to the swage dial 110.

Figure 14:
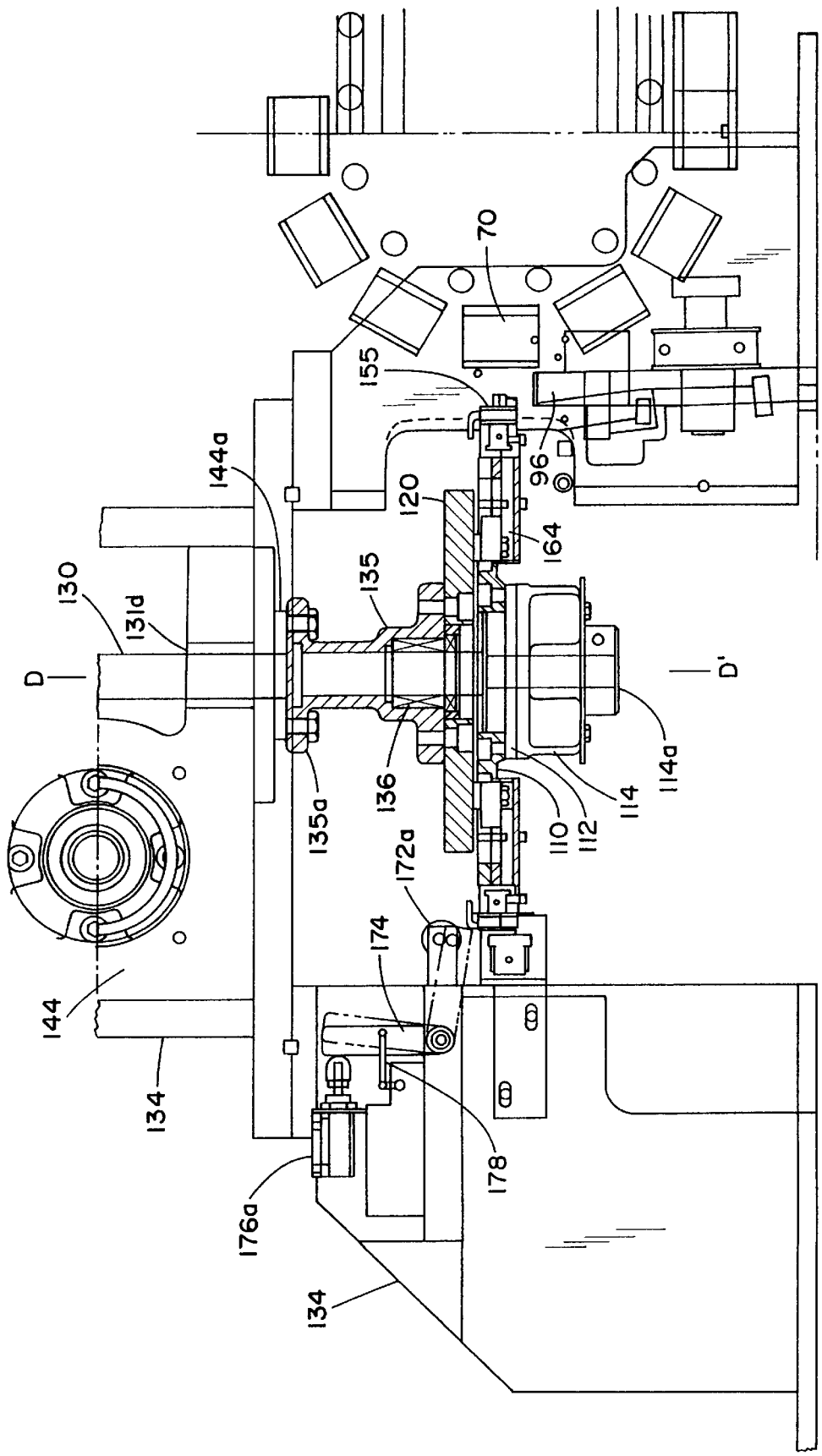
FIG. 14 is a detailed and partially cross section view of the drive for the swage dial taken along section lines "A"—"A" in FIG. 13(a) which illustrates a universal gripper ready to reciprocate outwardly to receive an oriented surgical needle from a precision conveyor.

The cam dial assembly 120 is mounted on an annular drive collar 135 which connects the output of the second indexing drive 144 to the cam dial plate 120 as more fully illustrated in FIG. 14. The annular drive 135 is journalled for rotation on drive shaft 130 by means of needle bearings 136 to provide a single drive axis D–D' for rotation of the swage dial assembly 110, 120. The annular drive collar provides suspension support and rotational drive for the cam dial assembly 120. The use of this annular collar also separates the cam dial and swage dial from the drive apparatus and enables operator workspace for alignment of the apparatus and for part changes when necessary. The annular drive collar 135 is bolted to the output drive flange of the indexing drive 144 as shone at 135(a).

The swage dial 110 is mounted for rotation on a ball detent clutch 114 which is fixably attached to shaft 130 and enables breakaway rotation between clutch drive plates 112 and 114 in the event of a catastrophic jam. The clutch 114 and shaft 130 also provide suspension support and rotational drive for the swage dial 110.

The annular cam drive 135 is bolted to the output of the second indexing drive 144 as illustrated at 135a and thus provides for both suspension support and rotation of the cam dial assembly 120. Likewise, the breakaway clutch 114 provides physical support and rotational drive for the swage dial 110 by virtue of its fixed mounting on shaft 130 at 114a.

The Swage Dial

Figure 18A:
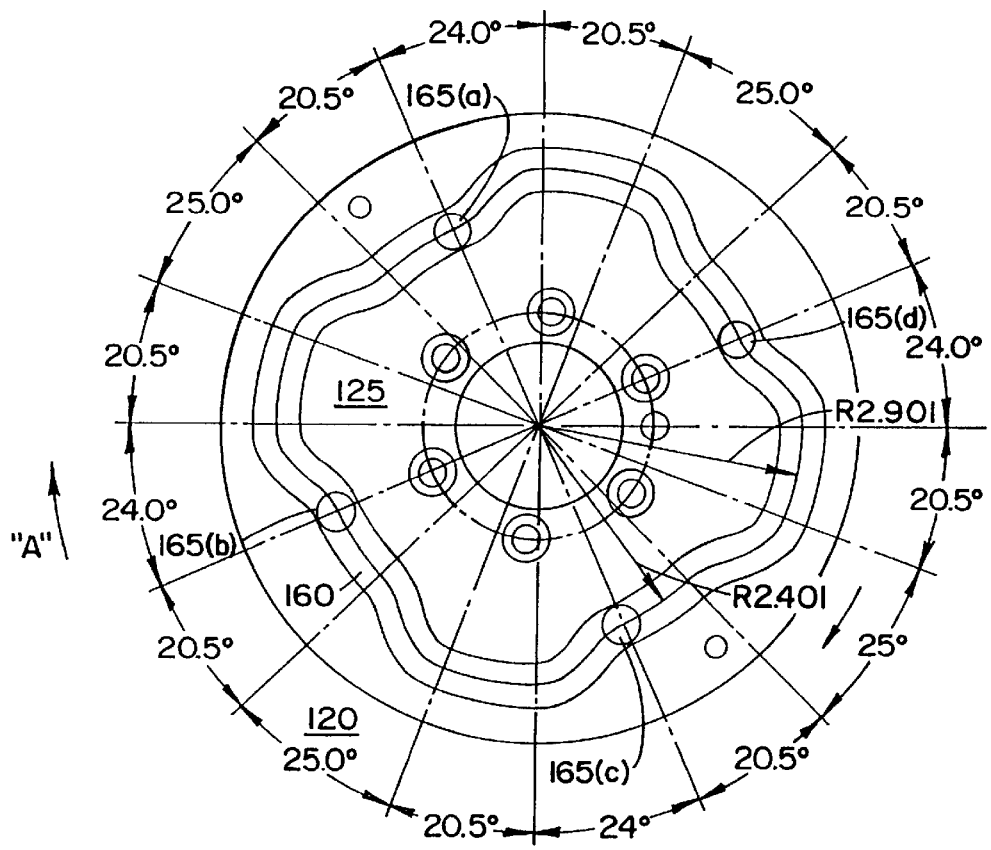

The process for extending each universal gripper 155 for needle processing at each of the stations 100, 200, 400, and 500 will now be explained. As shown in FIGS. 10(a), 10(b) and 10(c), each universal gripper 155 is connected to a reciprocating carriage 151 and a cam slide 164. Cam followers 165(a), (b), (c) and (d) are mounted to a cam slide 164 at one end thereof with the universal gripper at the other end. Cam slide 164 is slidable within stationary guides 166,167 and is adapted for reciprocal movement when the cam follower 165 is actuated. In the preferred embodiment shown in FIG. 18(a), cam followers 165(a)–(d) are rollers that fit within the cam track of a rotatable cam dial assembly 120. Cam dial assembly 120 is shown in FIG. 18(a) as comprising a cam dial plate 125 having a continuous cam tracks 160 which receives cam followers 165(a)–(d) attached to universal grippers 155a,b,c, and 155d, respectively. Each cam follower 165 is positioned within the cam track at each station for movement therein.

Figure 17A:
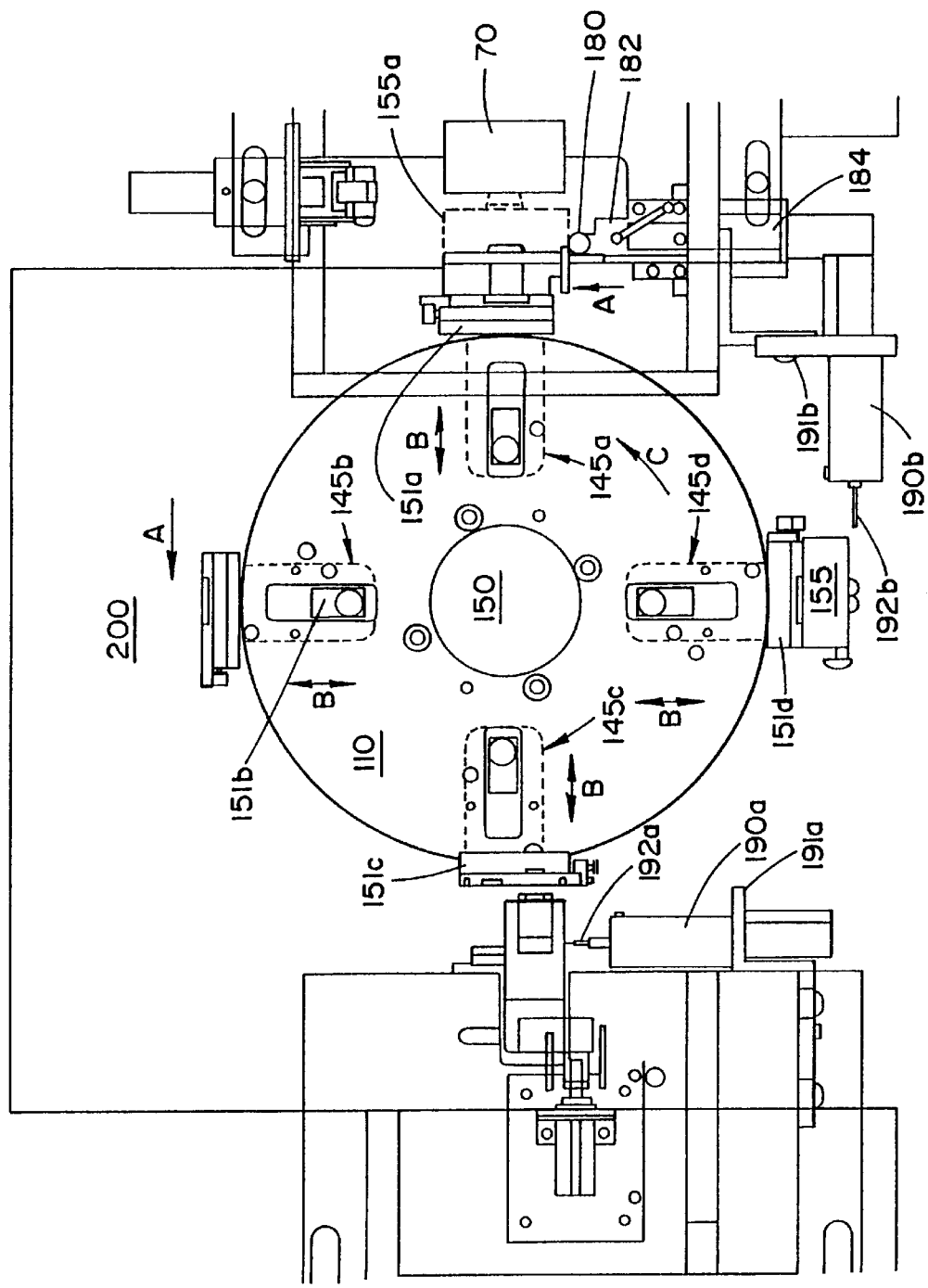
FIG. 17(a) is a top view of the swage dial assembly 150 comprising a swage dial plate 110 having four universal gripper stations 145a,b,c,d mounted thereon.
Figure 17B:
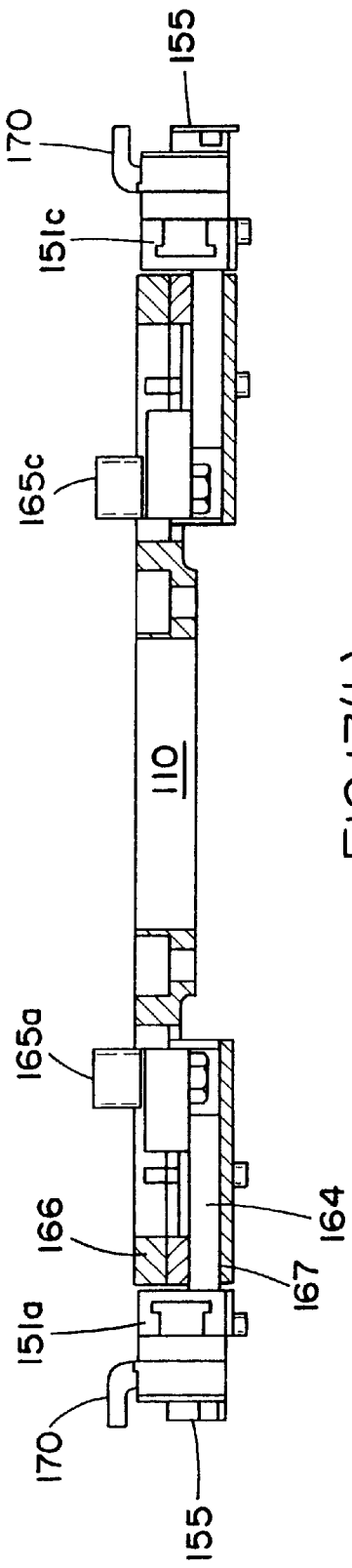
FIG. 17(b) is cross-sectional view of the four station swage dial assembly 150 showing two universal grippers 155 in a retracted position.
Figure 17C:
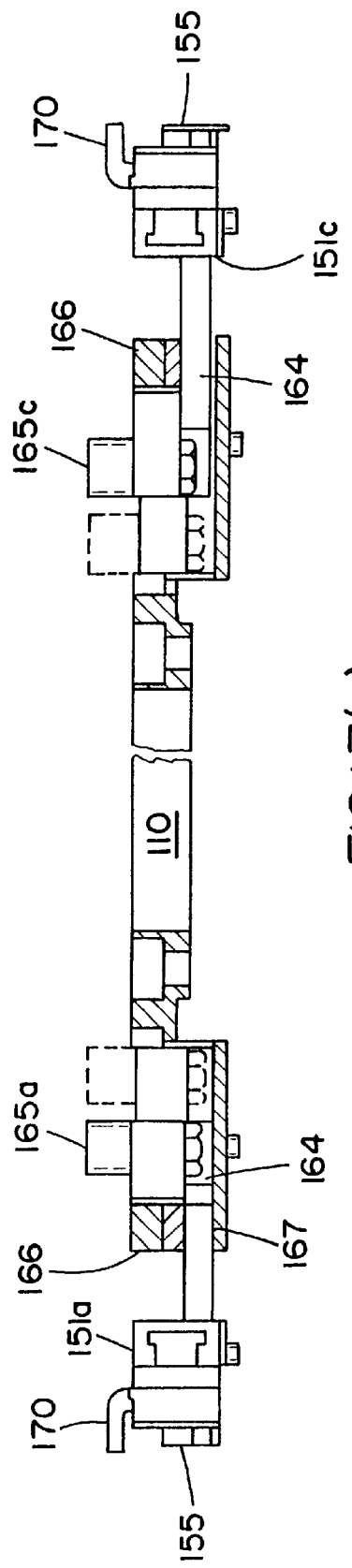
FIG. 17(c) is cross-sectional view of the four station swage dial assembly 150 showing two universal grippers 155 in an extended position.
Figure 18B:
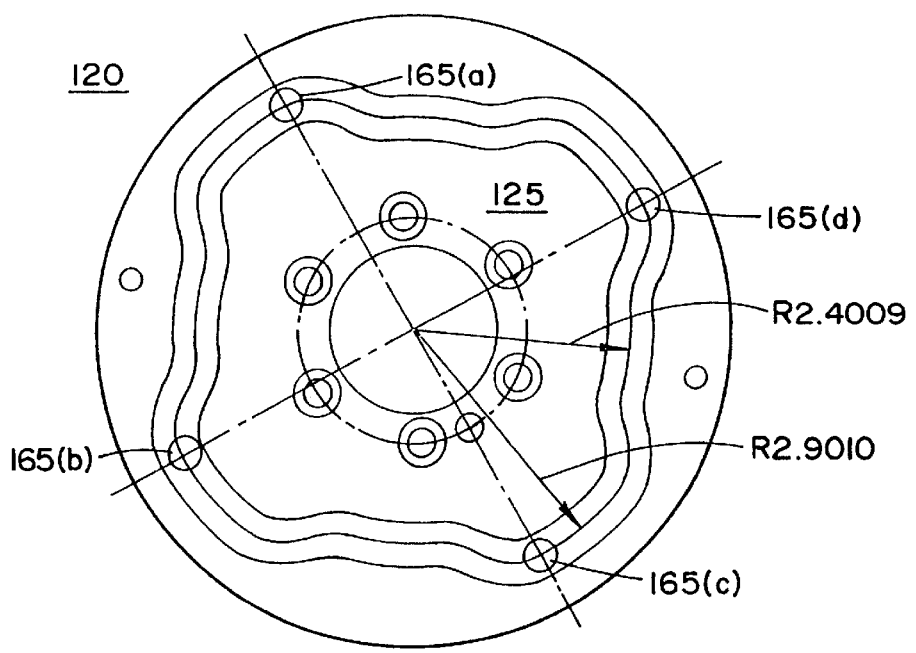

As illustrated in FIG. 18(a), cam dial 125 is positioned above swage dial 110 and mounted coaxial therewith. The cam dial 125 is rotatable about a central axis and controlled by a separate rotary indexing transmission as described previously so that it may rotate separately from the swage dial plate 110. The cam dial is driven in multiple drive and dwell cycles as previously explained, and the degrees of each phase are diagrammatically illustrated in FIG. 18(a). FIG. 18(a) also shows cam followers 165a–d in a first retracted position within the cam track 160. When the dials are in this position, each of the reciprocating carriages and consequently universal grippers 155 are in their retracted position as shown in FIG. 17(a) and 10(b) discussed above. To extend the universal grippers 155 in place at their respective stations, the cam dial plate 125 is rotated in the clockwise direction with respect to the swage dial plate 110, as indicated by the arrow A in FIG. 18(a), for approximately 25–45 degrees, forcing cam followers 165a–d in its cam track 160 to move toward the periphery of the dial as shown in FIG. 18(b). Consequently, each of the cam slides 164, reciprocating carriages 151a, and the universal grippers 155 move to the extended position as shown in FIG. 17(c). To move back to its retracted position, the cam dial plate 125 is rotated in the counter clockwise direction with respect to the swage dial plate 110 for approximately 20 to 30 degrees, forcing cam followers 165a–d in the cam track 160 to move to their retracted position (FIG. 18(a)). Consequently, the cam slide 164, reciprocating carriage 151a, and the universal gripper 155 move back to the retracted position as shown in FIG. 17(b) and discussed above.

It should be understood that when cam dial plate 125 rotates with respect to swage dial 110, each universal gripper 155 is either extended or retracted by the cam track. Thus, the system is designed so that all processes performed at each station occur simultaneously and for approximately the same duration of time when the universal grippers are in their extended position, for e.g., for needle pick-up, for needle swaging, or, for needle pull-testing.

When the universal gripper 155 is retracted, the needle engaged thereby may then be indexed to a different station for further processing. To index the needle to another station, both swage dial plate 110 and cam dial plate 125 are rotated together for approximately 90 degrees to position the universal gripper at the next station. For example, when the cam dial plate 125 and the swage dial plate 110 are simultaneously rotated 90 degrees counterclockwise in FIG. 17, the gripper 155 that had received the needle at station is now indexed to station 200 for swaging a suture thereto. Similarly, after swaging, the cam dial plate 125 and the swage dial plate 110 are simultaneously rotated counterclockwise so that the armed needle at station 200 is indexed to the pull-testing station 400 for pull-testing thereof. The operations performed concurrently at each station about the swage dial increases throughput to provide an output of pull-tested armed surgical needles at a rate of approximately 40 to 60 per minute in the preferred embodiment.

Universal Gripper

As illustrated in FIG. 1, the rotatable swage dial assembly 150 cooperates with four stations where simultaneous needle operations are performed. In the detailed illustration of FIG. 17(a), the swage dial assembly 150 includes a swage plate 110 having four universal gripper stations 145a, 145b, 145c, 145d spaced equally thereon.

The swage plate 110 is rotatably mounted at a central hub 112 on a ball detent safety clutch 114 (illustrated in FIG. 14) and operable to rotate under the control of a control system computer 46. In the preferred embodiment, a separate reciprocating carriage 151 is provided at each universal gripper station of the swage dial assembly 150. For instance, as shown in FIG. 17(a), universal gripper station 145a includes reciprocating carriage 151a, while station 145b includes reciprocating carriage 151b, station 145c includes reciprocating carriage 151c, and station 145d includes reciprocating carriage 151d. Mounted to each reciprocating carriage 151a, b,c,d for retractable movement therewith, is one universal gripper 155, two of which are shown connected to gripper mounts 150(a) and (d) in FIG. 17(a).

As previously mentioned, each reciprocating carriage 151a,b,c,d and universal gripper 155 connected thereto is movable from a retracted position to an extended position. When the gripper 155 is in the retracted position shown in FIG. 17(b), the needle 39 may be conveyed to a different station as the swage dial rotates; when the gripper 155 is in the extended position as shown in FIG. 17(c), the needle is in one of the active stations, such as the automatic swaging station.

The universal gripper of the present invention receives the needle from the precision conveyor and moveable hard stop mechanism, and transports the needle through the swage operation in which a suture is automatically inserted into the barrel end of the needle, and the metal of the needle swaged about the suture. As can be appreciated, when the opening in the barrel is only 0.0106 and the suture diameter is 0.0088, a high degree of precision handling is required, particularly so when the insertion and swage operation need to be completed in approximately 0.5 seconds in order to maintain a 30 to 60 needle per minute cycle rate. The universal gripper also transports the needle through the pull test station in which the suture bond is tested and to the packaging area, where the armed suture (needle and suture assembly) is bundled with other armed sutures for future packaging.

In FIGS. 14(a) (b) and (c), both the slide portion 164 and the gripper portion of the universal gripper 155 are illustrated, with a pair of needle gripping jaws 146 and 148, each having a portion of a needle receiving indent 157 formed therein. Each of the jaws have a reciprocal slide portion 146(a), 148(a) formed as an integral part, which slides reciprocate in a channel 162 formed in housing member 174, The jaws 146 and 148 are biased to each other and to a closed position by a spring member 160. The jaws are opened by a pair of moveable pivot linkages 166, 168 which are mounted to and actuated by plunger 170, so that when plunger 170 is depressed, the linkages 166, 168 are moved outwardly, drawing the jaws 146 and 148 with them. The plunger 170 is actuated by a cam driven by an air motor at each automatic station to open and close the jaws about a needle 39.

In the apparatus, a plurality of universal grippers are employed, preferably 4, each of which grips a single needle at positioning, at swaging, at testing and at off-load, as previously described. As the universal gripper is moved into position, the jaws 146,147 are opened and the gripper is reciprocated towards the needle so that open jaws are presented on each side of the needle. The jaws of the precision conveyor boat 70 are then opened, and during transfer, the needle rests on the moveable hard stop 96. The jaws 146,148 of the universal gripper are then closed to grip the needle and the moveable hard stop 96 is reciprocated out of engagement with the needle, and away from the jaws of the precision conveyor to allow the precision conveyor to advance the next needle into the needle transfer position.

The step of loading of the individual precisely oriented surgical needle 39 from the precision conveyor boat 70 and the moveable hard stop 96 onto the universal gripper 155 at the precision loading station 100 involves a compound movement on the part of the universal gripper. Since the needle is gripped in detents formed in the jaws of the conveyor boat 70, and since one of the jaws of the precision conveyor boat 70 is fixed, it is necessary for the universal gripper to transcend a compound movement when removing the needle from the conveyor boat jaws. If a straight reciprocal movement is attempted, the needle is stripped from the jaws of the universal conveyor by the detent in the fixed jaw of the conveyor boat 70. This compound movement is found at both the precision position station 100 and the swage station 200, which also uses fixed and moveable jaws. The use of a fixed jaw substantially improves the accuracy of the alignment of the needle with the suture at the swage station.

In the frontal view of the universal gripper as shown in FIGS. 15(a) and (b), jaws 146 and 148 of the universal gripper 155 extend perpendicularly from the gripper to engage the barrel end 44 of the arcuate needle 39.

FIGS. 15(a), (b) also illustrates two roller cam surfaces 172, 180 which act on the universal gripper. A cam surface 172 is found at each of the four stations, (Precise positioning, swage, test and off-load) and is used to open jaws 146 and 148 of the universal gripper at each station. FIGS. 7 and 8 also illustrate three pneumatic drives 176 (a), (b) and(c) which actuate rollers 172 (a), (b) and (c) to open and close the jaws of the universal gripper 155 as will be hereinafter explained in greater detail.

FIG. 14 illustrates a typical positioning for cam 172 above the needle pull test station, wherein cam roller 172(a) is mounted on a bell crank 174, which is actuated by an air cylinder 176(a). The cam 172(a) is normally biased to a non-engaged position by spring 178.

Each of the universal grippers 155 is mounted for linear movement with respect to the cam slide 164 by means of an off-set slide assembly, the details of which will be explained as with respect to FIGS. 14(a), (b) and (c). As indicated therein, the housing 174 of the universal gripper is mounted on a mounting block 175 and slide 177, and slide 177 is spring biased to a home position during reciprocation within slide carriage 151 by spring member 179. This second reciprocal movement is transverse to the reciprocal movement imparted by cam slide 164.

Figure 22A:
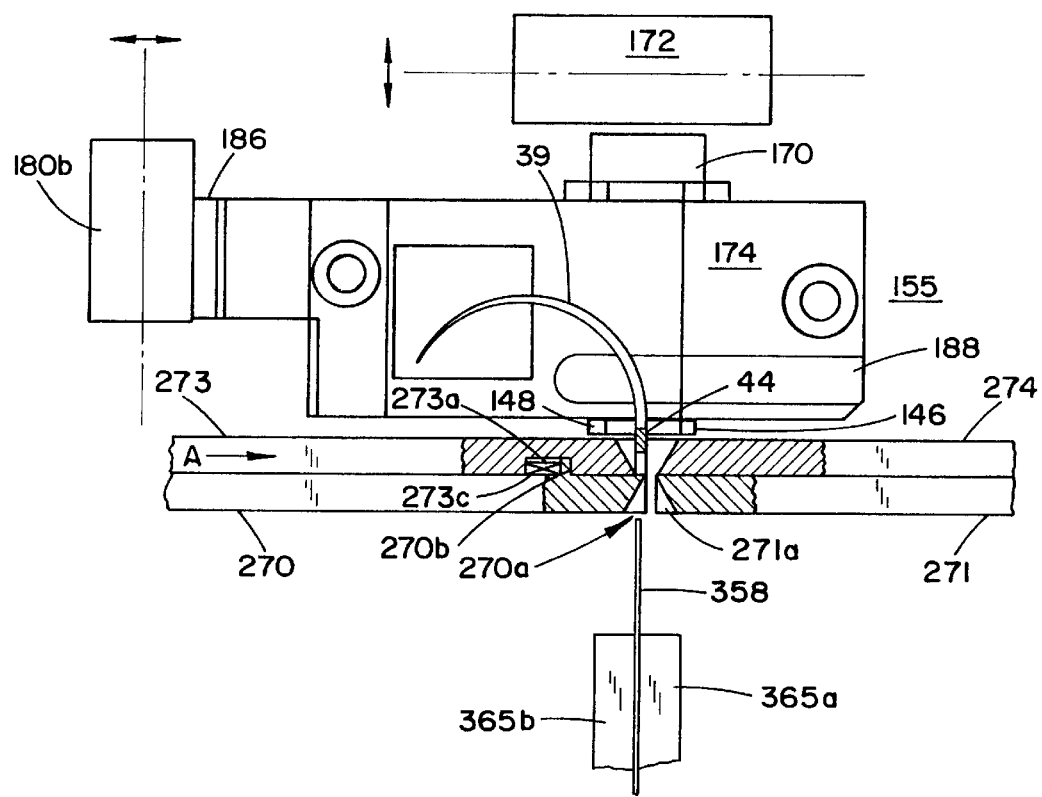
FIG. 22(a) is front face view of the universal gripper showing a surgical needle about to be placed in the swage dies of the present invention.
Figure 22B:
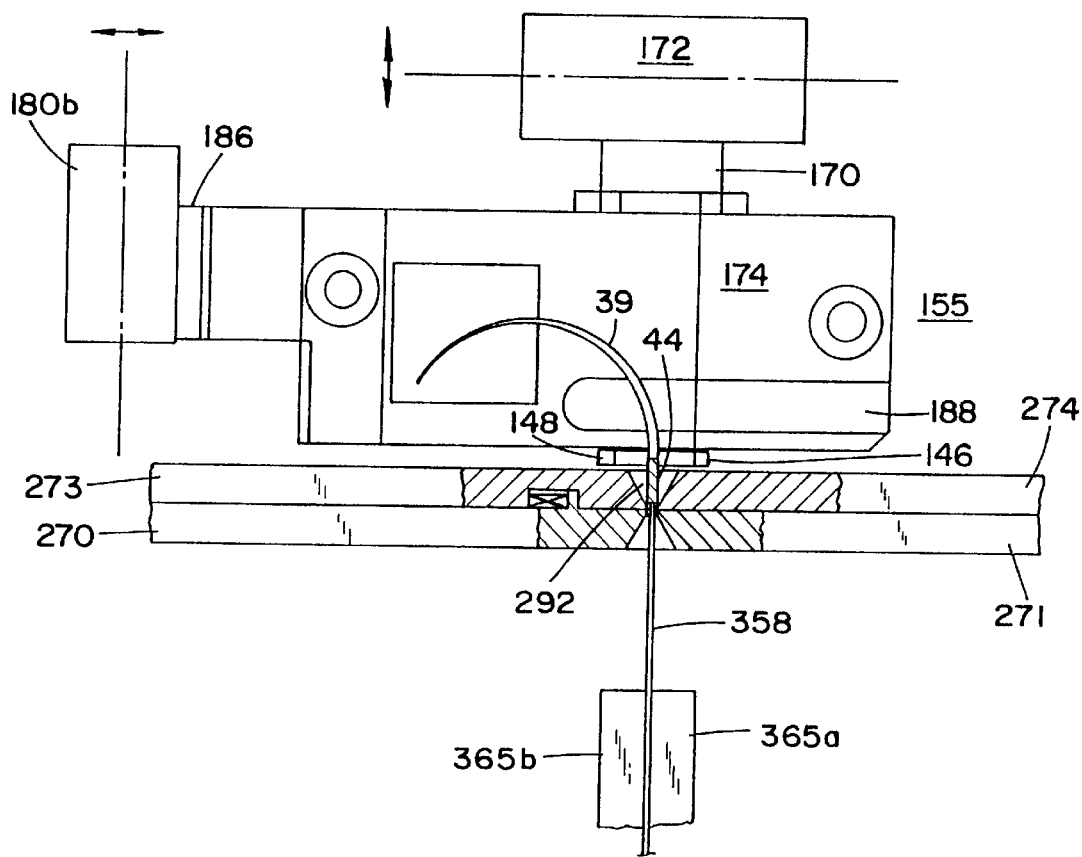
FIG. 22(b) is front face view of the universal gripper and a surgical needle with the universal gripper in a relaxed engagement, with the needle gripped by the swage dies of the present invention.

Referring to FIGS. 22(a), (b), roller cam 180 is used to provide the compound off-set movement of the universal gripper as it is reciprocated outwardly by the swage dial cam plate 125. FIG. 17(a) illustrates a typical positioning for the off-set drive used to drive cam roller 180 at the precise positioning station 100. Roller cam 180 is mounted on a linear slide 182, which is driven by an air motor 184, mounted on the swage dial frame. FIG. 17(a) also illustrates the relative motions of the universal gripper 155, with arrow A indicating the off-set movement, arrow B indicating the reciprocal movement which results in the radial reciprocation of the universal gripper 155 to 155a in FIG. 17(a), and arrow C indicating the rotary motion of the swage dial 110.

To accomplish the transfer of the needle to a universal gripper 155, the universal gripper 155 is extended and translated horizontally so that the face of the universal gripper is adjacent to the needle precision conveyor boat 70 as shown in FIG. 14 and 10(a). In this position, the jaws 146 and 148 penetrate the plane of the needle 39 on either side thereof. A load solenoid or similar device depresses a pusher arm of the precision conveyor boat 70 to release the needle from the engagement jaws 77,79 of the precision conveyor boat 70 so that it rests on the movable hard stop assembly between jaws 146 and 148 of the universal gripper 155. Simultaneously therewith, as controlled by the control system computer, jaws 146 and 148 are actuated from the non-engaging position to an engaging position to thereby engage the needle 39 in an oriented position as shown in FIG. 22(a). The universal gripper 155 is then off-set horizontally and retracted radially and the swage dial assembly 150 is rotated to the swaging station 200 to accomplish automatic swaging of the suture to the needle 39.

Needle Swaging Station

The swaging operation taking place at the swaging station will now be described with reference to FIG. 19, FIGS. 15(a)–(b) and FIGS. 19(a)–(c). FIGS. 15(a)–15(b) illustrate the universal needle gripper 155 and swaging and suture alignment dies shown in two stages of the suture insertion and needle swaging sequence. This sequence, and the interaction of the dies in relation to each other, the needle, and the insertion of the suture, accomplish the insert and swage function with minimal parts changes for each group of needle diameters and simple motions.

After conveying the needle to swaging assembly 200 shown in FIGS. 12 and 15(a), the universal gripper 155 is radially extended from the swage dial, and off-set to the side in the manner described above to position the suture receiving end 44 of needle 39 between the funnel shaped die opening formed at the ends of two swage dies 273,274 as shown in FIG. 22(a). As will be explained, swage die 274 is relatively fixed in position and swage die 273 is movable laterally toward the fixed swage die 274, as indicated by the arrow "A", to accomplish swaging of the suture receiving end of a needle placed therebetween. A funnel shaped die opening having an exit diameter slightly larger than the diameter of the suture receiving end 44 of the needle is formed when the two swage dies 273,274 are positioned adjacent each other as shown in FIGS. 15(b).

In the preferred embodiment shown in FIGS. 19(a) and 19(b), the ends of each of the swage dies 273,274 are provided with rectangular die cavities 283,284 respectively, to permanently swage the suture to needle 39. Note that as illustrated in FIGS. 19(a), (b), The swage dies are for a small 18 mil needle, and FIG. 26(a) has been magnified 2× and FIG. 26(b) magnified 100× for purposes of illustration. Different sets of swage dies may be provided, depending upon the size (diameters) of the needles and sutures to be swaged, and in the practice of the present invention, dies for needles ranging from 18 mil (0.018) to 50 mil (0.050). The die cavities illustrated in FIGS. 19(a), (b) are rectangular in shape with a 90 degree angle, and used to impart a permanent swage bond between needle and suture. Similar dies may be used with round die faces to impart a controlled release swage bond between the needle and suture.

To precisely position the suture receiving end 44 of needle 39 between the swage die opening formed at the ends of two swaging dies 273,274, the movable swage die 273 is temporarily moved apart. In the illustration of the swaging assembly 200 shown in FIGS. 19 and 15(a), swage die 273 is moved apart from the fixed swage die 274 by actuating air cylinder 295 to provide a force upon cylinder rod 293 to enable swage die operating lever 205 to pivot about pin 206 and pull a retraction arm 297 which engages stud 298 affixed to moveable swage die 273 a predetermined distance away from the fixed swage die 274. In the preferred embodiment, lever 205 is biased by spring 209 so that the movable swage die 273 will return toward the fixed swage die by the spring restoring force when the pressure provided by the air cylinder 295 is terminated.

FIG. 22(a) shows die 274 in its fixed position, and moveable die 273 in its spaced apart position prior to receiving the surgical needle 39 presented by universal gripper 155. Suture alignment die 270 containing suture guide funnel half 270(a) is positioned under swage die 273, and free to slide laterally within limits. Suture alignment die 270 has a tang 270(b) that protrudes into cavity 273a formed within swage die 273. Compression spring 273c bears against the back wall of cavity 273a and tang 270(b) such that funnel die 270(a) slides forward until it is constrained by the inner wall of cavity 273(a). In this position, it is forward of the center axis defined by the suture receiving end of the needle, and serves as a shelf that helps assure suture receiving end 44 of needle 39 is in position for swaging. In this stage of the cycle, the parts are not positioned for suture insertion, and suture clamps 365(a), (b) gripping suture 304 and stiffened end 358, are in dwell. Suture alignment die 271, containing funnel half 271(a), is fastened to swage die 274 by suitable fastening means.

Figure 19:
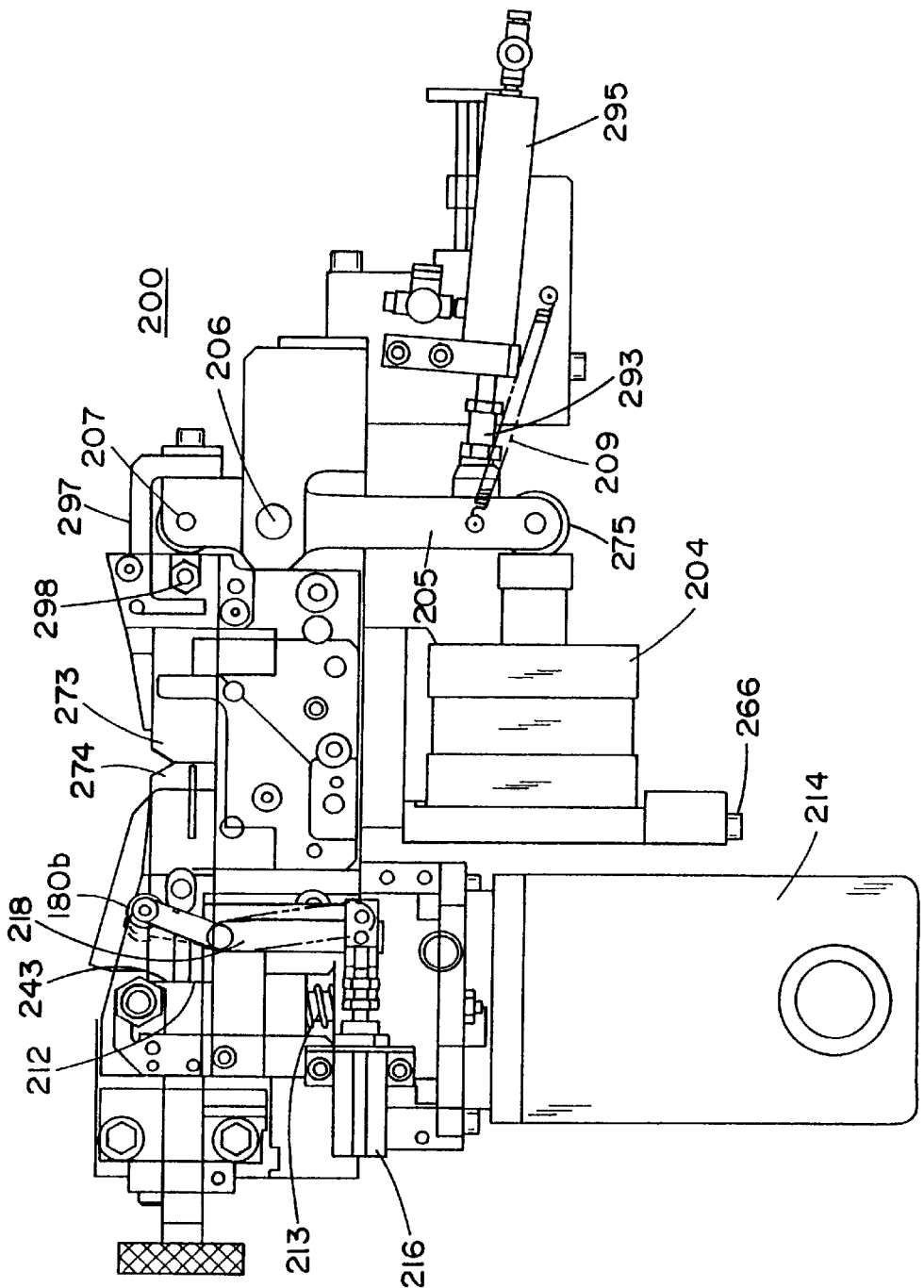
FIG. 19 is a top plan view of the swage assembly and off-set assembly of the present invention used for swaging the needles for suture attachment.

While the swage dies are apart, the universal gripper 155 is extended to position the suture receiving end 44 of needle 39 within the swage opening as shown in FIG. 22(a). Referring to FIG. 19, the universal gripper is off-set during entry and egress by cam roller 180(b), which is driven by air cylinder 216 through bell crank 218. This off-set is necessary to allow the needle to box step into the swage die opening 284 in the fixed swage die as it is placed in position by the universal gripper 155. After positioning the suture receiving opening 44 of needle 39 at the swage die opening 284, the moveable swage die 273 is moved toward needle 39 with the resilient spring force present in spring 209 that is sufficient to enable the dies 273,274 to grip and locate the suture receiving end 44 precisely against fixed swage die 274 without deforming the cavity of the suture receiving opening 44 formed therein. Concurrently, the jaws 146,148 of universal gripper 155 are opened by downward external force on plunger 170, by cam roller 172 as described above, thereby releasing the needle so that its position is determined by the grip of swaging dies 273 and 274. The motion of dies 273 and 270 causes the face of suture alignment die 270 to come in contact with the corresponding face of suture alignment die 271. The resilient force causing this motion is forceful enough to compress spring 273c, and move funnel die 270(a) to the left, such that tang 270(b) is no longer in contact with cavity wall 273(a). Dimensioning of dies 270 and 271 is such that this motion results in the formation of two funnel halves 270(a) and 271(a) defining a smooth conical shape that is coaxial with the suture receiving end 44 of needle 39.

FIG. 22(b) illustrates suture grippers 365(a), (b) moved vertically to the insertion position, which causes stiffened suture end 358 to enter the funnel defined at 270(a), 271(a), and be guided into the suture receiving cavity 44 of needle 39 axially aligned therewith. Note that the exit diameter of the conically shaped funnel guide formed of funnel halves 270(a) and 271(a) is preferably equal to or greater than the diameter of the suture tipped end 358 and smaller than the diameter of the suture receiving end 44 of the needle 39, so that the tipped end 358 of the suture strand may be easily inserted therein. An enlarged detail of the suture alignment dies 270,271 and the placement of the funnel portions 270(a) and 271(a) is illustrated in FIG. 26(c). Once the strand is inserted into the suture receiving end 44 of the needle (step 27) as discussed above, the automatic swaging of the suture receiving cavity occurs.

In the preferred embodiment of the swaging assembly 200 shown in FIG. 19, a pneumatic air cylinder 204 provides air pressure to actuate cam 275 that bears on lever 205 to pivot about pivot point 206 and drive cam 207 against the end of the moveable swage die 273 to thrust movable swage die 273 toward the fixed swage die to accomplish the swaging of the suture receiving end of the needle placed therebetween. Air pressure is supplied to the swage cylinder 204 via ports 266 under the control of the control system computer 46.

After the swage die 273 has been driven to a fixed stop by the swage cylinder, the suture receiving end 44 of needle 39 has been deformed to the desired shape defined by the swage die contours, as illustrated in FIG. 26(b). As deformation takes place, the moveable swage die 273 comes to a stop as a swage stop post which is press fit into the moveable swage die 273 strikes a reference wall cross milled into the frame of the swage assembly. When the swage stroke is performed, the swage cylinder drives the die and post assembly to the left (in FIG. 19) until it is positively stopped by the lower portion of post striking the wall of the cross milled groove in the assembly frame (located under swage die 273 in FIG. 19). This stalls air cylinder 204, so that the stroke of the moveable right hand die assembly shown is always the same for repeated cycles of the machine. In an alternative embodiment, both swage dies 273,274 may be movable towards each other to accomplish swaging.

In the preferred embodiment, the degree of swage compression imparted on the needle, and resulting strength of grip by the needle on the suture, is adjusted by precise positioning of the fixed die 274.

As shown in FIG. 19, servomotor 214 rotates a swage adjust screw 213. by driving a belt and reduction pulley on the end of swage adjust screw 213. The pitch of the swage adjust screw 213 is selected to move a sliding wedge 212 a small distance. The swage die 274 has a complementary ramp angle 243 at the opposite end which bears on the wedge 212 to retract or advance the position of the swage die 274 a precise distance proportional to the movement of the sliding wedge. Thus, the rotation of the swage adjust screw 213 and motion of the sliding wedge 212, results in transverse movement of the swage die 274 to thereby finely adjust its fixed position. For example, when a larger suture is to be swaged to a needle, the position of the fixed die 274 may be moved further away from the suture drawing axis so as to provide the desired amount of deformation when the swaging pressure is applied to the needle by the movable swage die 273. In the preferred embodiment shown in FIG. 19, the control system computer 46 will send the appropriate signals to automatically direct the servomotor 214 to adjust the position of the swage adjust screw 213, and hence, the position of the fixed die 274, in accordance with the pull-out test values of the needle-suture bond as measured by automatic pull-test system as explained in further detail below.

Specifically, appropriate control signals may be generated to direct the servomotor 214 to adjust the rotational position of the swage adjust screw 213 in accordance with stored statistical results of the pull-testing occurring at the pull-test station. Automatic pull-testing of the armed needle is desirable to ensure that the upstream swaging dies are optimally positioned to avoid over-swaging the needle-suture bond and hence, preventing the likelihood of clip-off, and, to avoid under-swaging the needle-suture bond to prevent the chance of pull-out.

Referring to FIG. 22(a), after the needle has been swaged to the suture, the universal gripper 155 closes jaws 146,148 on needle barrel end 44 as the drive roller 172 is reciprocated out of engagement with plunger 170. Simultaneously therewith, the moveable swage plate 273 is retracted to enable movement of needle 39 by the universal gripper 155. Before the swage dial 110 is rotated, the offset drive cam roller 180(b) is again advanced to bear against cam plate 186 and provide egress of the needle 39 from the swage die cavity in fixed swage plate 274. Once the universal gripper 155 and needle 39 have cleared the fixed swage plate, the cam dial assembly 120 is rotated advancing cam rollers 165 inwardly to retract the universal grippers 155 in a radial direction and enable rotation of the swage dial 110. Swage dial 110 then rotates the needle and suture assembly to a pull test station for testing.

Automatic Pull Test Station

Figure 27:
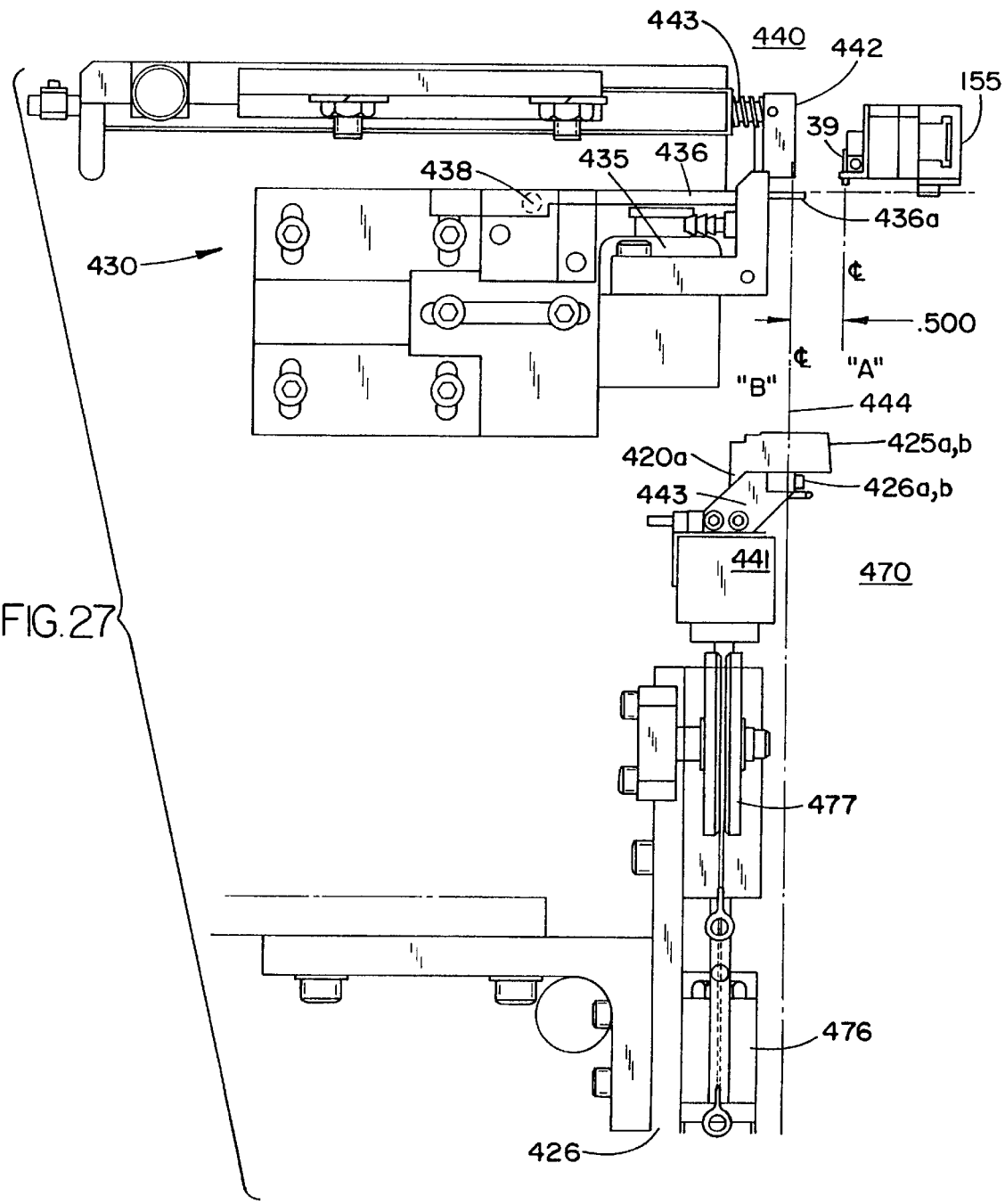
FIG. 27 is a diagrammatic side elevation view of the pull test apparatus of the present invention illustrating a load-cell assembly, the gripper assembly and a pull test assembly, and their relationship to the universal gripper.

The automatic pull-test station 400 that provides automatic pull-testing of a surgical needle and suture assembly is shown generally in FIGS. 27 through 30. As illustrated in FIG. 27 the automatic pull-test assembly 400 generally comprises a load cell mounting assembly 430 for mounting a load cell 435 which responds to loading of a V-plate needle arm 436 which receives the armed needle 39 from the universal gripper 155. A needle release cam roller 172(a) is provided for relaxing the armed needle from the grip of the universal gripper 155. A pull-test fence assembly 440 is provided to prevent the armed needle 39 from tipping over or becoming misaligned when the armed needle is relaxed.

The suture gripping assembly 470 includes two pairs of retractable grippers 425a,b and 426a,b for gripping the suture during the pull-tests. Grippers 425a,b are operatively connected to the weighted slide block assembly 472 for performing non-destructive pull-tests as will be described with respect to FIGS. 28 and 30. Two separate pneumatic cylinders are used to drive grippers 426a,b for destructive pull-tests.

A detailed description of each of these assemblies and their interaction will be explained in detail hereinbelow.

As shown in FIG. 27, a surgical needle 39 with attached suture is retained by a universal gripper 155 and, in the manner described above, is indexed to the automatic pull test station 400 by the rotary swage dial 150 to the position illustrated in FIG. 27. To position the armed needle 39 in the load cell 435, the universal gripper is extended from the swage dial 150 from center load "A" to center load "B" so that the end portion 44 of needle 39 is positioned above a corresponding receiving V-plate arm 436(a) of the load cell assembly 430 as shown in FIG. 27.

Figure 29A:
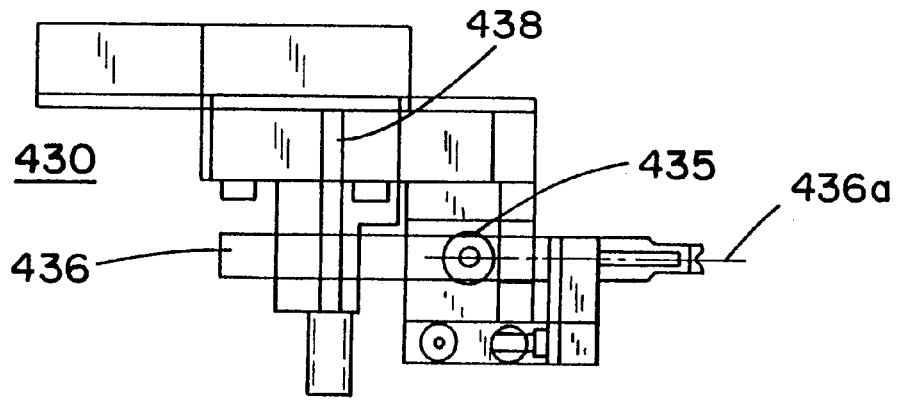
FIG. 29(a) is a plan view of the load cell assembly of the present invention, illustrating the v-plate needle arm.

FIG. 29(a) illustrates a top view of the load cell assembly 430 with load cell 435 mounted thereon. In the preferred embodiment, load cell 435 is loaded by a pivotally mounted V-plate needle arm 436 having a thin needle supporting blade 436(a) for supporting the suture receiving end portion 44 of various size surgical needles with the suture material 304(b) depending therefrom. Different V-plate arms may be provided for different needle suture combinations which accommodate larger and smaller sutures having diameters of approximately 0.009 to 0.017+/−0.001 inches. Depending upon the batch of surgical needles currently being pull tested, the appropriate needle V-plate supporting arm 436 will be positioned to receive the needle from the universal gripper.

Non-destructive pull testing of the armed surgical needle 39 is accomplished as follows:

After positioning the universal gripper 155 in the extended position as heretofore described, grippers 425a,b of suture gripping assembly 470 are closed from an open position to grip the suture strand slightly below the needle V-plate supporting arm 436 of load cell assembly 430 as shown in FIG. 20. A single pneumatic actuator 472 (illustrated in FIG. 28(a)) is provided for opening and closing gripper arms 425a,b and the cylinder is controlled by a control system program resident in control system computer 46 as explained in further detail in copending patent application U.S. Ser. No. 08/804,476 (attorney docket No. 10193) assigned to the same assignee of the present invention, the disclosure of which is incorporated herein by reference thereto.

Figure 28A:
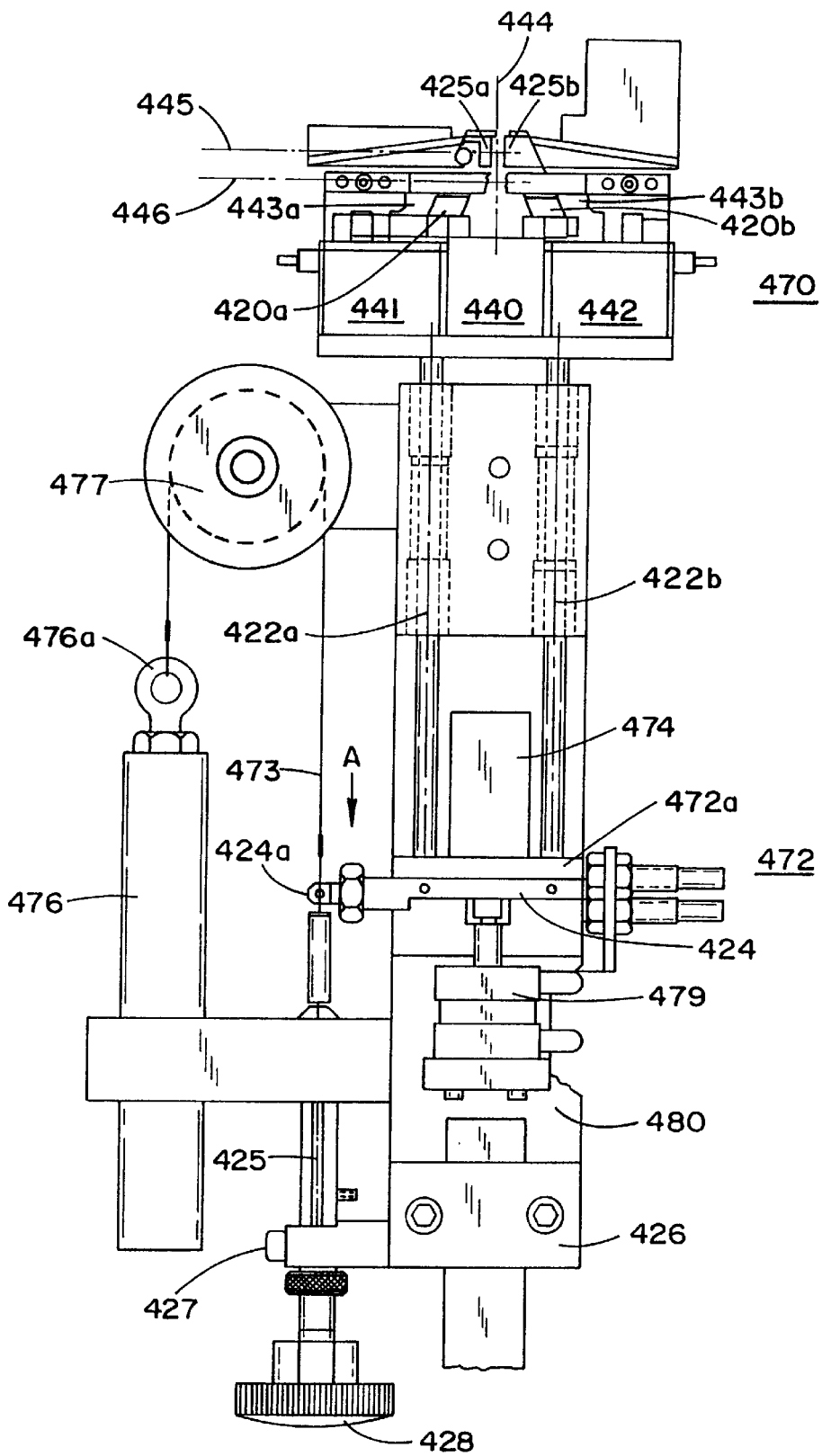
FIG. 28(a) is a front elevation view of at the pull test assembly illustrating the gripper assembly and the slide block assembly.
Figure 28B:
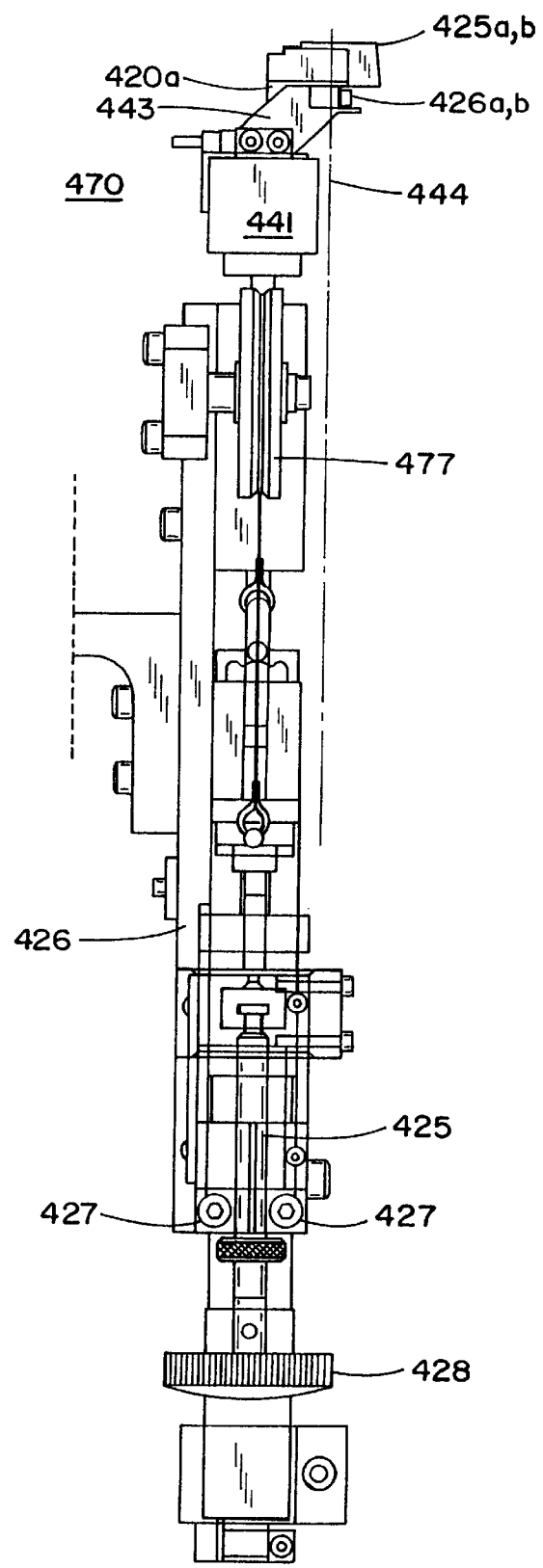
FIG. 28(b) is a side elevation view of the pull test assembly of FIG. 28(a) illustrating the gripper assembly and the slide block assembly.

FIGS. 28(a) and 28(b) illustrate the slide block assembly 472 that is composed of slide rods 422a,b and a lower slide block 472a which reciprocates vertically on the slide rods 422a,b. Slide block 472a includes a load balancing plate 424 upon which air cylinders 474, 479, apply respective upward and downward forces depending upon the type of pull-test that is to be performed. As shown in FIG. 27, air cylinder 479 is shown in an extended position providing an upward force that supports the load balance plate 424 and consequently maintains slide block 472a of slide assembly 472 at a fixed vertical position.

Slide block 472a is counterweighted to a net zero weight by appropriately sized counterweight 476 that is attached to the load balance plate at 424(a) and acts through cable 473, around pulley 477, and to attachment point 476a. This counterweight 476 acts to balance the net load on slide block 472a to a neutral position. An adjustable net downward force of 2 to 30 oz. is provided by an adjustable spring tension device 425, which is more clearly illustrated in FIG. 30. One end of spring tension device 425 is mounted to fixed position on the frame 426 by a mounting bolts 427. The other end of spring tension device 425 is attached to the load balancing plate 424 at 424a and exerts an adjustable downward loading between the load balance plate 424 and the fixed frame member 426. This adjustable download tension is normally offset by air motor 479 which drives the lower slide block 424 upward to a home position.

The amount of spring tension applied during a non-destructive pull-test can be varied from 2 to 30 oz. by rotation of knob 428 and the effective pull test loading is indicated by pointer 429 on scale 430.

To accomplish the non-destructive pull test, air cylinder 479, mounted on sub frame 480 and controlled by system computer 46, is relaxed from its extended position (FIG. 28(*a*)) supporting the load balance plate 424. This removes the upward force on load balancing plate 424 as shown in FIG. 28(*a*), to thereby impose the selected spring tension net weight of 2 to 30 ounces downwardly on slide block 472*a* and through slide rods 422 *a,b* to the gripper assembly 470 and the gripper jaws 425*a,b* to pull downwardly on the suture attached to swage needle 39, in the direction of arrow "A". The accuracy of this system is enhanced because slide block 472 is suspended on slide rods 422*a,b* which are mounted in low friction ball bushings, pressed into frame member 471, thereby imposing minimal mechanical drag on the system.

Note in FIG. 27, that the fixed slide block frame 426 is positioned parallel to the axis 444 of the suture depending from the needle 39, and is located a distance away from the axis corresponding to the length of the offset arms 420*a,b* of gripper jaws 425*a,b*.

Simultaneous with or momentarily before the slide assembly 472 is released, the needle release cam roller 172(*a*) is actuated to enable universal gripper 155 to disengage its grip on the armed needle 39. Releasing the armed needle from the grip of the gripper 155 is necessary to ensure that it is firmly positioned on the V-plate needle supporting blade at 436(*a*). Moreover, to provide an accurate pull-test, the needle must be released so that there is no existing upward force that would cause false results.

As shown in FIGS. 14 and 27, the needle release cam roller assembly comprises needle release solenoid 176(*a*) that is actuated to rotate pivotal lever arm 174. Pivotal lever arm 174 pivots about pin 174(*a*) to depress plunger 170 of the universal gripper 155 as previously described with respect to FIGS. 22(*a*), (*b*). As was described with respect to FIGS. 21(*a*)–(*c*), depressing plunger 170 opens jaws 146, 148 to release the needle 39 engaged therein.

Referring to FIG. 27, to prevent the needle 39 from becoming misaligned or from tipping over after the universal gripper 155 releases its grip on the needle, a needle fence assembly 440 is provided. As shown in FIG. 27, the needle fence assembly 440 includes vertical fence plate 442 which can be adjusted to lie a needle's diameter away from the face of gripper 155, and thereby retains the needle in an upright position for the test. Adjusting the lateral positioning of the vertical fence plate 442 is accomplished by rotating lead screws 443 (shown in FIG. 27) to advance or retract the fence for an appropriate distance. In the preferred embodiment, the configuration of the face of the vertical needle fence plate 442 (not shown) may be changed to accommodate the configurations of different size needles.

The controlled release of the minimum pull-test is of short duration, preferably ranging in milliseconds. If the test is successful, i.e., the suture meets the minimum pull-test requirements, the needle is re-gripped by the universal gripper 155 by deactuating the needle release solenoid 176(*a*) which retracts the cam roller 172(*a*) and releases the downward force on plunger 170. The suture gripper jaws 425*a,b* are then retracted to their open position to release their grip on the suture as controlled by the control system. Subsequently, the universal gripper 155 is retracted and the rotary swage dial 150 and rotated to convey the armed needle downstream for bundling.

If the suture fails the minimum pull-test, i.e., if the suture is dislodged from the surgical needle 39 as a result of the non-destructive test, the control system computer 46 is flagged so that the disarmed needle 39 will be ejected at the pull-test station. The dislodged suture strand will be drawn into a vacuum assembly (not shown) and the needle 39 will be ejected by a needle stripper assembly 190 shown generally in FIG. 17(*a*) and in detail in FIG. 24. As shown in FIG. 17(*a*), needle stripper solenoid 190(*a*) will be actuated by a control signal output from the control system computer 46 to extend needle stripper pin 192(*a*) to a space 188 (illustrated in FIG. 21(*b*) between the needle 39 and the face of the universal gripper 155. Thus, when the needle is in its relaxed state on the universal gripper 155 and the minimum pull-test fails, the needle stripper pin 192(*a*) is extended to remove the needle from the universal gripper 155. The needle will fall and be collected by appropriate collection means (not shown) located at the pull-test station.

After the pull test, whether successful or unsuccessful, the apparatus prepares for the next armed needle to be pull-tested. Slide block assembly 472 and retracted gripper jaws 325*a,b* are pushed back up with respect to the fixed slide mount frame 426 to the home position by an appropriate upward force supplied by the air cylinder 479 as controlled by the control system computer 46. At this time, another data signal may be sent for storage in a database maintained by the control system computer that indicates that the pull-test performed on the particular needle 39 was either successful or unsuccessful, together with a data signal which represents the loading on load cell 435. A signal flag may also be sent which indicates that a needle suture assembly is being conveyed downstream for bundling thereof.

Figure 29B:
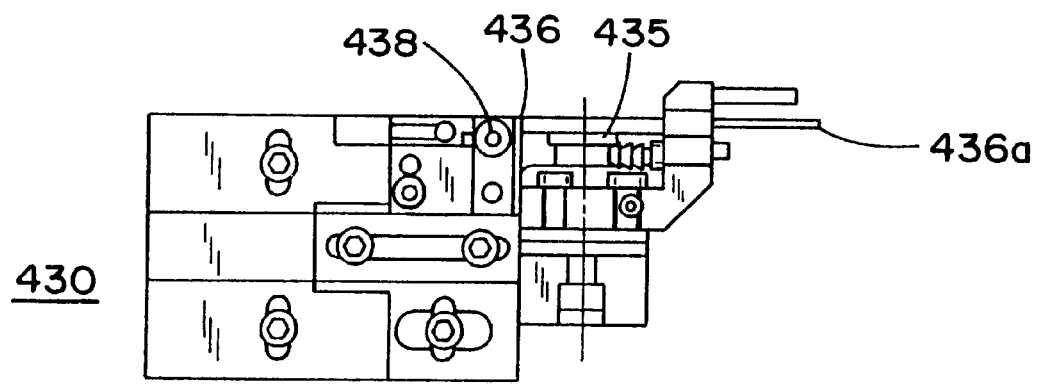
Figure 30:
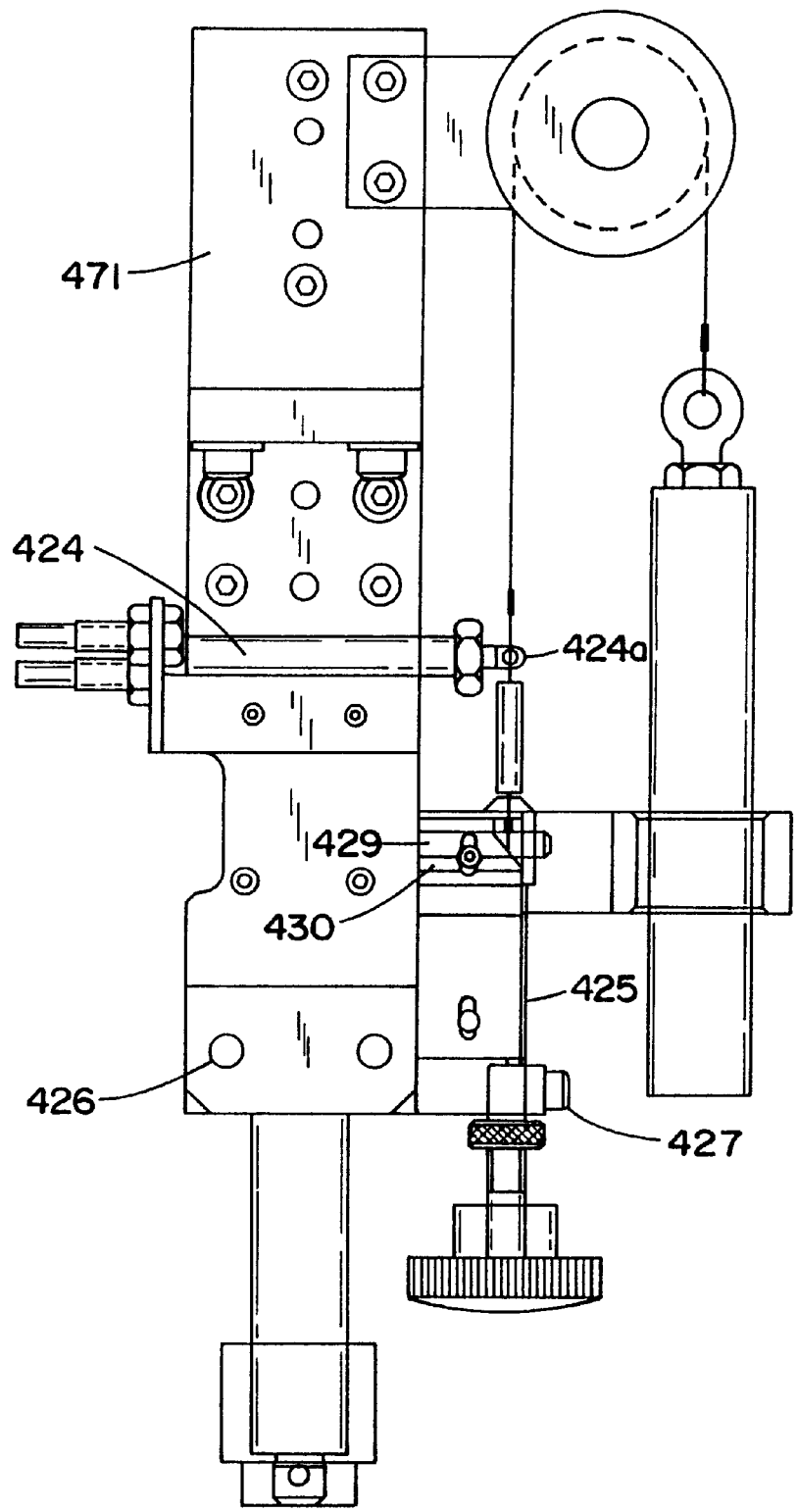
FIG. 30 is a rear elevation view of the pull test assembly illustrated in FIGS. 21(a) and 21(b)illustrating the spring tension assembly used for non-destructive pull tests.

In the preferred embodiment of the invention, the load cell 435, illustrated in FIGS. 27 and 29(*a*) 29(*b*) is a piezoelectric transducer that measures the force applied by the slide block assembly to the needle-suture assembly 39. The force is received by the needle v-plate arm at 436(*a*), and transmitted to load cell 435 mounted underneath the v-plate arm 436 by virtue of the pivotal mounting of the v-plate needle arm on bolt 438. This single point mount enables an easy parts change for needle v-plate arm when different needle or suture sizes call for a different opening at 436(*a*). The transducer load cell 435 may be interfaced with the control system computer 46 by conventional means, and, in the preferred embodiment, is a 25 lb. transducer manufactured by Techniques Co. (Model No. MDB-25PH). The forces applied to the suture 39 and measured by the load cell transducer 435 during the destructive pull-testing may be stored for statistical purposes or for real-time monitoring during a swage die setup routine that may take place when a new batch of surgical needles are to be swaged. For instance, if the non-destructive pull-tests fail and the force measured by the transducer 435 is determined to be at the low end of a predetermined range, then the control system computer 46 will acknowledge this and send appropriate signals to the upstream swaging assembly described previously causing the fixed swaging die 374 to be advanced an incremental amount toward the moveable swage die 373, resulting in subsequent swages being stronger. Likewise, if the non-destructive pull-test passes, i.e., the forces measured by the transducer are determined to be between a minimum and maximum load, then no die adjustment need be made.

As previously mentioned, the automatic pull-test assembly 400 is used to perform a minimum pull-test upon every armed surgical needle indexed thereto prior to automatic packaging thereof. A destructive pull-testing of the armed surgical needle is performed at a parts change set up and at every nth needle indexed thereafter. The purpose of performing a destructive pull-test is to set the swage dies located at the upstream swaging station for correct maximum swage pull-out value. This is by necessity a destructive test, and the test frequency, which is programmable, is set high enough to maintain control of the operation, but low enough to avoid excessive product waste. In the preferred embodiment, this frequency may be set at every 50th needle, but could be every 75th or 100th needle.

Another purpose of the destructive pull test is to aid in installing a new swage die set during a changeover procedure, which is a procedure that is used to prepare the needle swaging apparatus (swage dies) for processing a new batch of needles when they are of a different size from a previously processed batch. Contrary to the non-destructive pull-test described above, the pull-test apparatus is programmed for 100% destructive test of a swaged needle, while the swaging assembly is operating and feeding the armed needles to the pull-test station. The die adjustment system at the upstream swaging assembly will receive a signal from the computer 46 transducer load cell 335, at each machine cycle, and quickly perform a correct adjustment of the swage dies.

Destructive test pull-out values are recorded in the system computer 46 and are used to compute statistical process control information which is fed back to the machine operator through display screens.

Destructive pull testing of the armed surgical needle 39 is accomplished similarly as described herein above with respect to the minimum pull test, but with a second pair of gripper jaws 426a,b and destructive test air cylinder 474. However, the fundamental difference between the tests is a fixed mechanical stroke that is always strong enough to pull the suture out of the needle. This destructive stroke replaces the variable 2 to 30 ounce force of the minimum pull test routine.

As shown in FIG. 28(a), a second air cylinder 474 located opposite air cylinder 479 is programmed to provide a fixed stroke against load balancing plate 424 from the home position shown in FIG. 28(a). This results in a downward vertical displacement of lower slide block assembly 472 from the position shown in FIG. 28(a). This also results in a downward force upon slide rods 472(a) and (b), which moves the gripper assembly 470 downwardly, including gripper jaws 426a,b and the suture gripped therein, in the direction of the arrow "A" as shown in FIG. 28(a). The air pressure supplied to cylinder 474 is set high enough to always pull the suture out of needle 39. This stroke is limited by the bottom portion of slide assembly 472 striking the top of stationary frame 426. The destructive pull test jaws 426a,b are serrated on their gripping surface, as is shown in FIG. 28(a) to ensure a positive non-slip grip on the suture during the destruct cycle. Further, the destruct gripper jaws 426a,b are driven by a pair of air cylinders 441,442 through angled offset arms 443,444.

The axis of reciprocation for each of the sets of jaws is illustrated in FIG. 28(a), with the axis for the non-destruct gripper at 445, and the axis of reciprocation for the destructive gripper jaws illustrated in FIG. 28(a) at 446.

The force necessary to accomplish the destructive pull-test is measured by the piezoelectric load cell transducer 435 as discussed above, and data representing this force is sent to the control computer 46. If it is determined by the process control algorithm (described below) that the destructive pull-test forces as measured by the transducer load cell are lower than a predetermined range of pull-test values, the control system computer 46 will send out appropriate control signals to increase the swaging die stroke applied when swaging the suture to the needle at the upstream swaging station. If it is determined that the destructive pull-test forces as measured by the transducer load cell are higher than the predetermined range, the control system computer 46 will send out appropriate control signals to the upstream swaging assembly to move a fixed swage die a small incremental distance away from the moveable swage jaw, thereby decreasing the swaging pressure applied when swaging the suture to the needle.

Since the destructive pull-test necessarily results in the suture becoming dislodged from the needle 39, the needle 39 is again removed from the grip of the universal gripper 155 by the needle stripper pin 192(a) as described above. Subsequently, the gripper jaws 426a,b are retracted to their open positions and air cylinder 479 provides the upward force to restore the gripping assembly 470 and slide block assembly 472 back to their normal position in preparation for the next pull-test.

Off Load Dial Assembly For Needles and Sutures

Figure 23:
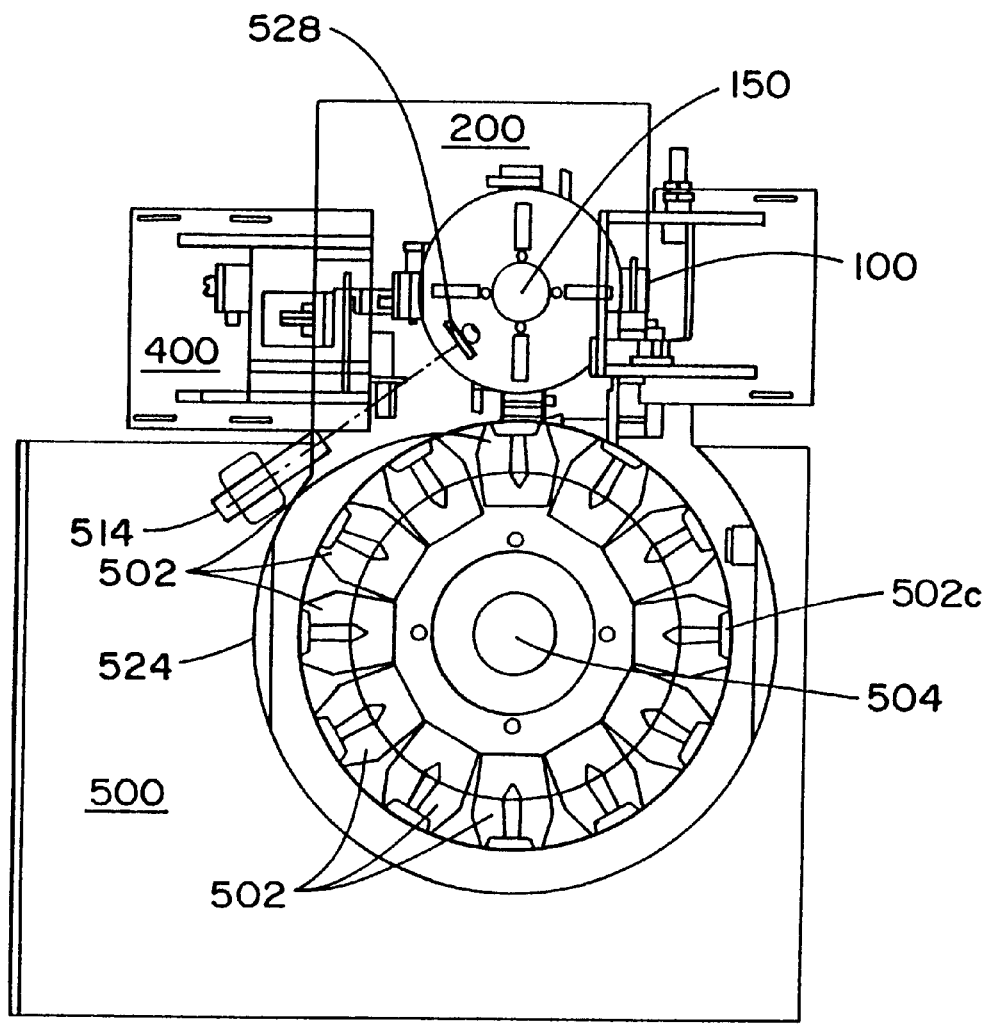
FIG. 23 is a top plan view of the needle bundling station of the present invention illustrating a plurality of compartments, each of which receives a predetermined number of needle and suture assemblies.

The off load station 500 is more particularly illustrated and described with respect to FIGS. 23 and 25–25(b) in which a plurality of needle buckets 502 are circumferentially arranged on a rotatable turntable 504 to be indexed under the collection point 506 defined by an intercept axis of a needle stripper 190 and the face of the universal gripper 155. As the needles are stripped from the universal gripper, they fall into a needle collection bucket which collects the needle inside the bucket, and most of the suture outside the bucket.

One needle stripper assembly 190 is illustrated in FIG. 24, which stripper includes a reciprocating stripping pin 192, which is spring biased inwardly by spring 193, and reciprocated outwardly by pneumatic motor 194 to engage the needle to be stripped. The stripping assemblies are secured in position by means of a bracket 191 which is bolted to the frame of the apparatus.

The present invention includes a pair of needle strippers 190a,190b, the locations of which are illustrated in FIG. 17(a) adjacent the circumference of the swage dial plate 110. Needle stripper assemblies 190(a), (b) are mounted to the frame of the stand alone swage machine by means of brackets 191a,191b to provide a longitudinal axis of reciprocation for the needle stripping pins 192a,b that is tangential to the circumference described by the face of the universal grippers 155. When the needle stripper pins 192 are retracted, as illustrated in FIG. 24, the universal gripper passes the needle stripping station without engagement. However, when the needle stripping pins are reciprocated outwardly, they intercept the path of needle 39 and are positioned to reciprocate into a space 188 (illustrated in FIGS. 21(b) and 15) defined between the face of the universal gripper 155 and the needle 39. Simultaneously therewith, the plunger 170 on the universal gripper is depressed by one of the off load cams 172 to open the jaws 146,148 of the universal gripper and enable the needle to be stripped from the universal gripper.

One needle stripper is used at the pull test station to remove needles that have failed the suture pull test, and a second is used at the off load station to insure a positive removal of the needle and suture assembly from the universal gripper at the off load station.

The needle stripper assembly 190(a) illustrated in FIG. 17(a) is used to remove needles that have failed the pull test at the pull test station 400. The needle stripper assembly 190(b) is used to remove the needle and suture assembly from the universal gripper for bundling in the off load station 500.

The needle bucket of the present invention is illustrated in FIGS. 25–25(b), wherein FIG. 25 is a side view illustrating the a side view of the bucket and the radial reciprocation of the needle bucket, with FIG. 25(a) illustrating a front view of the bucket and FIG. 25(b) illustrating a top view of the bucket.

As illustrated in FIG. 25, dotted line axis A illustrates the circumferential path of the needle in a horizontal plane, while carried by the universal gripper, while axis B and C illustrate the the radial reciprocation of the universal gripper 155 mounted on the swage dial. The needle stripping pin 192b engages the needle at the intersection of axis A and C at intersect 506 causing the needle to drop into the needle bucket 502. The needle falls into the bucket with the suture draped over a comb-like face 520 which holds the suture and assists in preventing entanglement of the sutures when they are removed from the needle bucket. Most of the suture remains outside the bucket, and is captured within a suture shroud 524, illustrated in FIG. 23. The suture shroud 524 guides the unsupported end of the suture and prevents entanglement with the moving parts of the apparatus below the circumferential path described by the universal gripper. In addition, a stream of deionized air may be provided at this station to assist in the orderly collection of the sutures following the swage assembly.

Each of the needle buckets includes a second comb-like surface 522 on one side of the bucket, and an upstanding extended wall portion 526 on the far side of the collection bucket to assist in capturing any late dropping needles.

Each of the needle buckets 502 is spring mounted for radial reciprocation on turntable 504 by means of a spring loaded reciprocating mount 508 which nominally biases the needle bucket 502 inwardly. When the needle bucket has arrived at the off load position, the bucket 502 is reciprocated outwardly as illustrated in FIG. 25 by a pneumatic motor 510 to the position 502b illustrated in FIG. 25.

FIG. 23 also illustrates a detector 514 which is focused on a reflector plate 528 under the swage dial assembly 150 that is triggered by a passing suture to actuate the needle stripping assembly 190(b).

After a predetermined number of needle and suture assemblies have been collected in the needle bucket 502, the needle bucket 502 is reciprocated inwardly by relaxing air motor 510 and the turntable 504 is indexed to position the next available needle bucket 502 under the off load station. While 12 off-load buckets 502 have been illustrated in FIG. 23(a), it is understood that a smaller number of buckets could be used if desired.

After a needle bucket 502 has been filled with a predetermined number of needle and suture assemblies, and rotated to the position illustrated at 502(c) in FIG. 23, the bundle of needle and suture assemblies may be removed for subsequent handling and packaging.

As is readily apparent to one skilled in the art, many variations on the above described embodiment are possible. The foregoing description is exemplary only and not to be construed as limiting the scope of the invention, which is defined in the claims, as follows.

What is claimed:

1. A needle threading and swaging apparatus for attaching a suture to a surgical needle having a suture receiving opening formed therein, said apparatus comprising:

(a) a needle singulating station for receiving a plurality of randomly arranged surgical needles, said station including a sliding surface for assisting an operator in singulating surgical needles for transfer to an indexing conveyor;

(b) a robotic apparatus for transferring said surgical needles from said indexing conveyor to a precise positioning apparatus, said robotic apparatus and said precise positioning apparatus orienting each surgical needle in a precise position for subsequent automatic handling at a first predetermined location;

(c) a universal gripper for receiving each precisely positioned surgical needle at said first predetermined location and indexing each of said surgical needles in a predetermined orientation from said first predetermined location through successive locations for sequential processing at subsequent predetermined locations;

(d) a suture cutting station located at a second predetermined location for automatically cutting an indefinite length of suture material to a definite length and automatically inserting said suture into said suture receiving opening formed in said surgical needle;

(e) a swage station for swaging said surgical needle to close said suture receiving opening about a free end of said suture to secure said suture thereto and form therefrom a needle and suture assembly;

(f) means for receiving said needle and suture assemblies from said universal gripper for subsequent packaging;

whereby unsorted needles and an indefinite length of suture material are formed into a plurality of needle and suture assemblies.

2. The needle threading and swaging apparatus according to claim 1 wherein said universal gripper means includes a compound movement from a first retracted position to a second extended position with respect to said indexing means.

3. The needle threading and swaging apparatus according to claim 2 wherein said universal gripper means includes first and second jaws for engaging said surgical needle, said jaws having a first engaging position for engaging said surgical needle in a precisely oriented position, and a second non-engaging position for releasing said surgical needle.

4. The needle threading and swaging apparatus according to claim 3, wherein said robotic apparatus further comprises:

(a) first means for obtaining an image of said needles deposited upon said first conveyor means, said means including digitizing means for converting said image into digital signals;

(b) computer control means for processing said digital signals to obtain positional and orientation data for a selected randomly positioned needle upon said indexing conveyor means; and (d) gripper means for removing said randomly positioned needle from said indexing conveyor and positioning it upon said precise positioning apparatus for further orientation and conveyance thereof, wherein said transfer means grasps each of said selected needles in accordance with its respective positional and orientation data when removing it from said indexing conveyor.

5. The needle threading and swaging apparatus according to claim 4 wherein said singulating station further includes a sliding surface with at least one insert drop for singulating said surgical needles for deposition upon said indexing conveyor means, each of said singulated needles being deposited upon said indexing conveyor means in a spaced apart relation.

6. The needle threading and swaging apparatus according to claim 4 wherein said computer control means further includes a means for processing said positional and orientation data to obtain therefrom instructions for enabling said gripper means to grasp said selected randomly deposited needle in accordance with its respective positional and orientation data.

7. The needle threading and swaging apparatus according to claim 4 wherein said means for obtaining an image of said randomly deposited needles includes one or more video cameras.

8. The needle threading and swaging apparatus according to claim 5 wherein said singulating station further includes at least one insert drop positioned above a transfer surface adjacent said indexing conveyor so that individual surgical needles can be automatically transferred from said transfer surface to said indexing conveyor.

9. The needle threading and swaging apparatus according to claim 4 wherein said gripper means includes an articulated robot arm for grasping each of said needles based upon said positional and orientation data received from said computer control means.

10. The needle threading and swaging apparatus according to claim 4 wherein said precise positioning apparatus includes a plurality of carrier means each for receiving a single surgical needle from said gripping means, each individual carrier means having a means for engaging a single surgical needle transferred thereto.

11. The needle threading and swaging apparatus according to claim 10 wherein each of said engaging means includes a first fixed jaw and a second movable jaw for engaging a needle positioned therebetween by said gripping means.

12. The needle threading and swaging apparatus according to claim 11 wherein each of said carrier means further includes spring means for biasing said second movable jaw into engagement with said first fixed jaw to retain said needle positioned therebetween.

13. The needle threading and swaging apparatus according to claim 11 wherein said carrier means further includes means for retracting said second movable jaw from engagement with said fixed jaw for removing said needle positioned therebetween.

14. The needle threading and swaging apparatus according to claim 13 wherein said means for retracting said second movable jaw from engagement with said fixed jaw is a push rod for pushing said second movable jaw in opposition to said bias of said spring means.

15. The needle threading and swaging apparatus according to claim 4 further including a second means for obtaining a second video image of a second individually singulated surgical needle, said second video image being processed by said computer control means for obtaining positional and orientation data of a second selected individually singulated surgical needle, said control means selecting a surgical needle to be positioned from said first or said second individually singulated needles, wherein said gripping means grasps said second singulated surgical needle based upon its respective positional and orientation data and transfers said needle to said precision conveyor means when said computer control means determines that said first singulated surgical needs cannot be transferred by said gripping means.

16. The needle threading and swaging apparatus according to claim 10 wherein said precision conveyor means further includes a first orienting plough for orienting each of said needles positioned on their respective carrier means in a uniform direction.

17. The needle threading and swaging apparatus according to claim 16 wherein said precision conveyor further includes a pre-positioning means for further orienting said needle within said first and second engagement jaws of said carrier means.

18. The needle threading and swaging apparatus according to claim 17 wherein said precision conveyor means further includes a moveable hard stop assembly for further orienting said needle to within 0.001 inch of said predetermined orientation upon said carrier means.

19. The needle threading and swaging apparatus according to claim 4 wherein said precision conveyor means positions said carrier means in a confrontingly opposed relation with said universal gripper means to enable said first and second jaws of said universal gripper means to receive said oriented needle from said carrier means.

20. The needle threading and swaging apparatus according to claim 19 wherein said universal gripper means is horizontally translated as it is reciprocated into a gripping position to enable said jaws to grip said surgical needle in said oriented position.

21. The needle threading and swaging apparatus according to claim 20 wherein said indexing means conveys said needle to said second location with said universal gripping means engaging said needle in said oriented position.

22. The needle threading and swaging apparatus according to claim 3, wherein said second means located at said second predetermined location comprises:

(a) a drawing frame, said frame having at least one longitudinal member and defining a drawing axis parallel thereto;

(b) means for feeding a flexible indefinite length suture strand to said drawing axis for drawing and cutting;

(c) first and second gripping means for gripping said indefinite length suture strand and drawing it along said drawing axis, said first gripping means mounted for reciprocal movement on said at least one longitudinal member;

(d) means for cutting said indefinite length suture strand; and (e) said second gripping means reciprocal to a start position along said drawing axis and below said cutting means, while said first drawing means is drawing said indefinite length suture strand to an insertion zone located a predetermined distance beyond said cutting means, whereby said indefinite length suture strand is inserted within said suture receiving opening of said needle and cut to a predetermined length by said cutting means after said second gripping means has gripped said indefinite length suture strand at said start position.

23. The needle threading and swaging apparatus according to claim 22 wherein said at least one longitudinal member further defines reciprocal guide means for said first and second gripping means.

24. The needle threading and swaging apparatus according to claim 23 further comprising first and second drive motors for enabling reciprocal movement of respective first and second gripping means.

25. The needle threading and swaging apparatus according to claim 24 further comprising a computer control means for said first and second drive motors to draw said indefinite length suture strand to said predetermined distance beyond said cutting means.

26. An apparatus as claimed in claim 25 further comprising a moveable carrier mounted for selective movement along said drawing axis, said movable carrier having a heating means for tipping said suture mounted thereon.

27. The needle threading and swaging apparatus according to claim 26 wherein said computer control means further comprises at least one sensor means for determining the position of said moveable carrier.

28. The needle threading and swaging apparatus according to claim 22 wherein said feeding means further comprises means for automatically tensioning said indefinite length suture according to a predefined suture type during at least the drawing and cutting thereof.

29. The needle threading and swaging apparatus according to claim 22 wherein each of said first and second gripping means further include retractable gripping elements having a first engaged position and a second retracted position, wherein one of said first and second gripping means traverses the drawing axis on a draw stroke with gripping elements engaged, and the other of said first and second gripping means reciprocates along the same axis with the gripping elements retracted to avoid mechanical interference therewith.

30. The needle threading and swaging apparatus according to claim 22 further including a first vacuum means for temporarily restraining the cut end of said suture strand after cutting thereof.

31. The needle threading and swaging apparatus according to claim 30 further including a second vacuum means for proximate positioning of said indefinite length suture strand prior to cutting.

32. The needle threading and swaging apparatus according to claim 26 wherein said carrier further comprises means for heat treating a portion of said indefinite length strand of suture material while under tension at said treatment zone to form a tipped portion of said indefinite length strand.

33. The needle threading and swaging apparatus according to claim 32 wherein said heat treating means is mounted on said movable carrier remote from said cutting means.

34. The needle threading and swaging apparatus according to claim 33 wherein said heat treating means is heating a portion of said strand at a position remote from said to allow for partial hardening of said suture prior to cutting thereof.

35. The needle threading and swaging apparatus according to claim 34 wherein said cutting means cuts said stiffened strand remote from said treatment zone to create a suture strand of definite length supported by said first gripping means and a suture strand of indefinite length supported by said second gripping means, with stiffened portions above each gripping means.

36. The needle threading and swaging apparatus according to claim 22 wherein said swage station includes first and second swaging die means, said first swaging die means having an end thereof defining a portion of a swage die opening, and said second swaging die means having an end thereof defining another portion of said swage die opening, wherein said second swaging die means is positioned next to said first swaging die means to form a swage die opening for receiving said needle.

37. The needle threading and swaging apparatus according to claim 36, wherein said first swaging die means is fixed in position and said second swaging die means is laterally movable toward and away from said first fixed swage die means.

38. The needle threading and swaging apparatus according to claim 36, wherein said swage die opening is axially aligned with said drawing axis at said second predetermined position, with said universal gripper means in said retracted position at said predetermined position prior to positioning said surgical needle within said swage die opening, and is extended and translated in a compound movement to position said suture receiving opening of said needle in said swage die opening prior to swaging.

39. The needle threading and swaging apparatus according to claim 38 wherein said swage station further includes a funnel guide means positioned at said insertion zone between a free end of said definite length suture strand and said suture receiving opening of said needle, said funnel die means including a tapered opening axially aligned with said swage die opening for directing said free end of said suture strand into said suture receiving opening of said needle positioned therein.

40. The needle threading and swaging apparatus according to claim 39 wherein said funnel guide means further includes a registration means for aligning it with at least one of said first and second swaging dies.

41. The needle threading and swaging apparatus according to claim 40 wherein said funnel guide means includes a first fixed suture alignment die having an end thereof defining a portion of said tapered opening, and a second movable suture alignment die having an end thereof defining another portion of said tapered opening, wherein said second movable suture alignment die is positioned next to said first fixed suture alignment die to form said tapered opening.

42. The needle threading and swaging apparatus according to claim 39 wherein said tapered opening has a suture exit diameter that is larger than the diameter of said suture strand and smaller than the diameter of said suture receiving opening defined in the needle.

43. The needle threading and swaging apparatus according to claim 42 wherein said first gripping means is advanced along said suture drawing axis to direct said free end of said suture strand through said funnel guide means and into said suture receiving opening of said needle positioned in said swage die opening.

44. The suture threading and swaging apparatus according to claim 38 wherein said swaging means includes means for moving said second swage die means laterally away from said first swage die means prior to positioning said needle within said swage die opening.

45. The needle and suture threading and swaging apparatus according to claim 44, wherein said moving means further moves said second swage die means toward said first swage die means to grip said needle placed therebetween.

46. The needle and suture threading and swaging apparatus according to claim 45 wherein said moving means includes spring biasing means to provide a force sufficient to move said second swage die toward said first swage die to grip the needle without deforming said suture receiving opening of said needle positioned at said swage die opening.

47. The needle and suture threading and swaging apparatus according to claim 46, wherein said moving means includes an air cylinder means for supplying adequate force to thrust said movable swage die means toward said first swage die means to accomplish swaging of said needle gripped therebetween.

48. The needle and suture threading and swaging apparatus according to claim 47, wherein said second swage die means is thrust towards said first die means for a swaging stroke of a predetermined distance to accomplish said swaging.

49. The needle and suture threading and swaging apparatus according to claim 48, wherein said moving means includes stop means for terminating the motion of said second swage die means during said swaging stroke.

50. The needle threading and swaging apparatus according to claim 49 wherein said jaws are opened to a non-engaging position for relaxing said surgical needle in said swage die opening after gripping but before swaging thereof.

51. The needle threading and swaging apparatus according to claim 50, wherein said swaging means further includes a fence for maintaining the position of said needle within said swage die opening during the swaging thereof.

52. The needle threading and swaging apparatus according to claim 46 wherein said swaging means further includes means for adjusting the position of said first swaging die means to change the amount of swage deformation occurring to said suture receiving opening during swaging thereof.

53. The needle threading and swaging apparatus according to claim 52 wherein said first fixed swaging die means includes a wedge follower located at one end thereof, said means for changing the position of said first fixed swaging die means including a wedge assembly positioned to move transverse to said wedge follower to laterally move said wedge follower and said first fixed swaging die means in accordance with transverse movement of said wedge assembly.

54. The needle threading and swaging apparatus according to claim 53 wherein said transverse movement of said wedge assembly is controllable by a servomotor means for rotating a swage adjust screw of a predetermined pitch, said rotation of said swage adjust screw being translated into linear motion of said wedge assembly.

55. The needle threading and swaging apparatus according to claim 54 wherein said computer control means determines and controls the optimum positioning of said first swaging die means to avoid over-swaging and underswaging said needle.

56. The needle threading and swaging apparatus according to claim 22 wherein said cutting means is a retractable cutter comprising:

(a) a cutting blade mounted for at least reciprocal movement transverse to said first axis defined by said indefinite length strand from a first retracted position to a second cutting position;

(b) first and second locator arms for accurately positioning said indefinite length strand of suture material for cutting thereof, and for supporting said strand as the cutting blade traverses said first axis as it reciprocates from said retracted position to said cutting position, whereby said cutting blade is angled with respect to its reciprocating motion to effect a slice ratio of at least 1:1 as said blade cuts said supported suture strand at said cutting position to obtain a clean, broom-free cut.

57. The needle threading and swaging apparatus according to claim 56 wherein said cutting means further comprises:

(a) a stationary guide means, said guide means positioned adjacent said indefinite length suture strand to be cut; and (b) an actuator means mounted on said stationary guide for providing at least reciprocal movement along a second axis transverse to said first axis;

wherein said cutting blade is responsive to said reciprocating actuator to move from said first retracted position to said second cutting position.

58. The needle threading and swaging apparatus according to claim 57 wherein said first and second locating arms have support blocks located on a first end thereof and a pivotally mounting at a second end thereof with respect to said stationary guide for moving said support block means from a first retracted position to a second strand supporting position in response to movement of said actuator.

59. The needle threading and swaging apparatus according to claim 58, wherein said support blocks include a V-shaped notch for supporting said suture strand on two sides during the cutting thereof.

60. The needle threading and swaging apparatus according to claim 59, wherein said first and second locating arms further include an over center link which isolates motion from said actuator means after said support blocks have engaged said strand.

61. The needle threading and swaging apparatus according to claim 60, wherein said over center links translate reciprocal movement of said actuator means into pivotal movement for said locating arms.

62. The needle threading and swaging apparatus according to claim 61, wherein said stationary guide is spaced from said indefinite length strand by the effective length of said pivotal locating arm.

63. The needle threading and swaging apparatus according to claim 57, wherein said first axis and said second axis are transverse to each other.

64. The needle threading and swaging apparatus according to claim 57 further including a blade holder mounted on said actuator for supporting said cutting blade during reciprocal motion thereof.

65. The needle threading and swaging apparatus according to claim 61, wherein each of said first and second over center linkages further comprises first and second links, with said first link fixedly mounted on said actuator and said second link connecting said first link and said pivotal locating arm.

66. The needle threading and swaging apparatus according to claim 57, wherein said cutting blade is angled with respect to said second axis to horizontally cut said strand with a slicing movement when said blade crosses said first axis.

67. The needle threading and swaging apparatus according to claim 66, wherein said cutting blade and said support blocks are both retracted behind said stationary guide when in their respective retracted positions.

68. The needle threading and swaging apparatus according to claim 50 wherein said one of said gripping jaws of said universal gripper means is actuated to said engaging position after swaging of said needle, to thereby engage said needle and suture assembly.

69. The needle threading and swaging apparatus according to claim 3 further including a suture test station at a third predetermined location for automatically testing the swage bond of said needle and suture assembly, said suture test station including a support means for supporting said needle and suture assembly.

70. The needle threading and swaging apparatus according to claim 69 wherein said indexing means conveys said needle and suture assembly to said third location with said universal gripping means engaging said needle in said oriented position.

71. The needle threading and swaging apparatus according to claim 70 wherein said universal gripper means is in said retracted position prior to positioning said needle and suture assembly upon said support means, and is extended to position said needle and suture assembly upon said blade means while enabling said suture strand to be threaded within said support means.

72. The needle threading and swaging apparatus according to claim 69 wherein said suture test station for automatically testing the strength of said swage bond of said needle and suture assembly further includes at least one suture gripping means for positively gripping said suture strand at a first position below said support means, said suture test station including a pneumatic drive for applying a positive downward force of predetermined value to said gripped suture strand to destructively test the strength of said swage bond.

73. The needle threading and swaging apparatus according to claim 69 wherein said suture test station for automatically testing the swage bond of said needle and suture assembly includes a pneumatic drive means for maintaining said gripping means at a first home position prior to applying said positive downward force to said gripped suture.

74. The needle threading and swaging apparatus according to claim 72 wherein the force applied by said pneumatic drive is computer controlled and said universal gripper means is computer controlled to release its engagement of said needle and suture assembly at the time of or before said suture gripping means grips said suture to enable said pneumatic drive to apply said destructive downward force to said suture strand to thereby test the strength of said swage bond.

75. The needle threading and swaging apparatus according to claim 73 wherein said suture gripping means and said pneumatic drive are positioned substantially parallel with a vertical axis defined by said suture strand.

76. The needle threading and swaging apparatus according to claim 75 wherein said pneumatic drive includes a first air cylinder means for applying upward pressure to a slide block which supports said suture gripping means to maintain said gripping means at a home position.

77. The needle threading and swaging apparatus according to claim 76 wherein said upward pressure applied to a first side of said slide block means is relaxed to enable said slide block means to exert a downward pressure in response to a predetermined spring tension applied to said slide block.

78. The needle threading and swaging apparatus according to claim 72 wherein said fourth means for testing the strength of said swage bond of said needle and suture assembly further includes a spring tension means for controlling the application of said downward force applied to said suture strand.

79. The needle threading and swaging apparatus according to claim 78 wherein said means for controlling the application of said downward force is a counterweight positioned to oppose a gravitational force generated by said slide block means and an adjustable spring tension device which adds to said gravitational force.

80. The needle threading and swaging apparatus according to claim 79 wherein said fourth means for automatically testing the strength of said swage bond further includes one or more needle v-plate supporting means for supporting armed surgical needles.

81. The needle threading and swaging apparatus according to claim 72 wherein said gripping means includes first and second pairs of retractable gripper arms.

82. The needle threading and swaging apparatus according to claim 74 wherein said fourth means for automatically testing the strength of said swage bond of said needle and suture assembly further includes means for measuring the value of said positive downward force applied to said suture strand by said slide block and said adjustable spring tension device.

83. The needle threading and swaging apparatus according to claim 82 wherein said measuring means includes a piezoelectric transducer for measuring the deflection of said needle v-plate supporting means when said positive downward force is applied to said gripped suture strand.

84. The needle threading and swaging apparatus according to claim 83 further including a computer control means connected with said transducer means for outputting a test fail signal if said suture becomes dislodged from said needle after application of said downward force.

85. The needle threading and swaging apparatus according to claim 84 wherein said computer control means enables the automatic adjustment of said swage station in accordance with measured values obtained from said measuring means.

86. The needle threading and swaging apparatus according to claim 85 wherein said fourth means for automatically testing said swage bond further includes means for removing said needle from said universal gripper means upon receipt of said test fail signal from said control means.

87. The needle threading and swaging apparatus according to claim 81 wherein said universal gripper means is retracted from an extended position after pull-testing said needle and suture assembly.

88. The needle threading and swaging apparatus according to claim 3 further including a fifth means located at a fourth predetermined location for automatically receiving said needle and suture assembly and for grouping a plurality of needle and suture assemblies as a bundle of needle suture assemblies.

89. The needle threading and swaging apparatus according to claim 88, wherein said indexing means conveys said needle and suture assembly to said fourth predetermined location for transferring said needle and suture assembly to said fifth means for receiving said needle suture assembly.

90. The needle threading and swaging apparatus according to claim 89 wherein said fifth means for receiving said needle and suture assembly includes a means for stripping said needle suture assembly from said universal gripper.

91. The needle threading and swaging apparatus according to claim 90 wherein said fifth means for receiving said needle and suture assembly includes a plurality of buckets for incrementally receiving a bundle of needle suture assemblies.

92. The needle threading and swaging apparatus according to claim 91 wherein said plurality of buckets are arranged to rotate below said means for stripping said needle suture assembly from said universal gripper.

93. The needle threading and swaging apparatus according to claim 92 wherein said indexing means conveys said universal gripper means in a confronting relation with said means for stripping, said universal gripper means depositing an individual oriented needle and suture assembly into a predetermined one of said buckets .

94. The needle threading and swaging apparatus according to claim 2 wherein said indexing means further includes a rotary dial means with a plurality of said universal gripper means and off-set means positioned radially thereon, said rotary dial means rotatable about a central axis for indexing said universal gripper means sequentially from said first, to said second, to said third, and to said fourth predetermined locations.

95. The needle threading and swaging apparatus according to claim 94 wherein said indexing means further includes cam dial means includes one or more cam tracks located about a periphery of said rotary dial means, each of said cam tracks defining a retracted portion thereof and an extended portion thereof.

96. The needle threading and swaging apparatus according to claim 95 wherein said universal gripper means includes a cam follower means positioned within a respective cam track of said cam dial means for extending and off setting said universal gripper means when said cam follower is positioned within said extended portion of said cam track and for retracting said universal gripper means when said cam follower is positioned within said retracted portion of said cam track, said off-set means and said cam follower providing a compound motion for said universal gripper.

97. The needle threading and swaging apparatus according to claim 96 wherein said rotary dial means is rotated in a first direction relative to said cam dial means to move said cam follower of said universal gripper means from said retracted portion to said extended portion, thereby moving said universal gripper means from said first retracted position to said second extended position.

98. The needle threading and swaging apparatus according to claim 97 wherein said rotary dial means is rotated in a second direction relative to said cam dial means to move said cam follower of said universal gripper means from said extended portion back to said first retracted portion, thereby moving said universal gripper means from said second extended position back to said first retracted position.

* * * * *